US010820855B2

(12) United States Patent
Cheatham, III et al.

(10) Patent No.: US 10,820,855 B2
(45) Date of Patent: Nov. 3, 2020

(54) SYSTEMS, METHODS, AND DEVICES TO INCENTIVIZE INHALER USE

(71) Applicant: Elwha LLC, Bellevue, WA (US)

(72) Inventors: Jesse R. Cheatham, III, Seattle, WA (US); Roderick A. Hyde, Redmond, WA (US); Robert C. Petroski, Seattle, WA (US); Lowell L. Wood, Jr., Bellevue, WA (US); Victoria Y. H. Wood, Livermore, CA (US)

(73) Assignee: Elwha LLC, Bellevue, WA (US)

( * ) Notice: Subject to any disclaimer, the term of this patent is extended or adjusted under 35 U.S.C. 154(b) by 1557 days.

(21) Appl. No.: 14/549,398

(22) Filed: Nov. 20, 2014

(65) Prior Publication Data
US 2016/0045683 A1    Feb. 18, 2016

Related U.S. Application Data

(63) Continuation of application No. 14/459,075, filed on Aug. 13, 2014.

(51) Int. Cl.
*A61M 15/00* (2006.01)
*A61B 5/00* (2006.01)
(Continued)

(52) U.S. Cl.
CPC ............ *A61B 5/4839* (2013.01); *A61K 9/007* (2013.01); *A61K 9/0073* (2013.01); *A61M 15/0003* (2014.02); *A61M 15/007* (2014.02); *A61M 15/008* (2014.02); *A61M 15/009* (2013.01); *A61M 15/0021* (2014.02); *A61M 15/0071* (2014.02); *A61B 5/0816* (2013.01); *A61M 15/002* (2014.02); *A61M 2016/0027* (2013.01); *A61M 2016/0039* (2013.01); *A61M 2205/13* (2013.01); *A61M 2205/3303* (2013.01); *A61M 2205/3306* (2013.01); *A61M 2205/3334* (2013.01); *A61M 2205/3375* (2013.01);
(Continued)

(58) Field of Classification Search
CPC ............ A61B 5/4839; A61M 15/0003; A61M 15/0021; A61M 15/007; A61M 15/0071; A61M 15/008; A61M 15/009; A61K 9/007; A61K 9/0073; A24F 47/002; A24F 47/004; A24F 47/006; A24F 47/008
See application file for complete search history.

(56) References Cited

U.S. PATENT DOCUMENTS 5,333,106 A    7/1994  Lanpher et al.
5,347,998 A    9/1994  Hodson et al.
(Continued)

FOREIGN PATENT DOCUMENTS

CN    1780655 A    5/2006
EP    1005916 A1   7/2000
(Continued)

OTHER PUBLICATIONS

PCT International Search Report; International App. No. PCT/US2015/044773; dated Nov. 13, 2015; pp. 1-4.
(Continued)

*Primary Examiner* — Samchuan C Yao
*Assistant Examiner* — Ned T Heffner

(57) ABSTRACT

The present disclosure relates to systems, methods, and devices that may be used to incentivize inhaler use.

32 Claims, 27 Drawing Sheets

(51) Int. Cl.
*A61K 9/00* (2006.01)
*A61B 5/08* (2006.01)
*A61M 16/00* (2006.01)

(52) U.S. Cl.
CPC .............. *A61M 2205/3553* (2013.01); *A61M 2205/3569* (2013.01); *A61M 2205/3584* (2013.01); *A61M 2205/3592* (2013.01); *A61M 2205/502* (2013.01); *A61M 2205/505* (2013.01); *A61M 2205/507* (2013.01); *A61M 2205/581* (2013.01); *A61M 2205/582* (2013.01); *A61M 2205/583* (2013.01); *A61M 2230/40* (2013.01)

(56) References Cited

U.S. PATENT DOCUMENTS

| | | | |
|---|---|---|---|
| 5,392,768 A | 2/1995 | Johansson et al. | |
| 5,404,871 A | 4/1995 | Goodman | |
| 5,419,315 A * | 5/1995 | Rubsamen | A61M 15/0065 128/200.14 |
| 5,497,764 A | 3/1996 | Ritson et al. | |
| 5,540,934 A | 7/1996 | Touitou | |
| 5,672,581 A | 9/1997 | Rubsamen et al. | |
| 6,142,146 A | 11/2000 | Abrams et al. | |
| 6,196,219 B1 | 3/2001 | Hess et al. | |
| 6,197,333 B1 | 3/2001 | Onyuksel et al. | |
| 6,221,385 B1 | 4/2001 | Camu et al. | |
| 6,269,810 B1 | 8/2001 | Brooker | |
| 6,316,024 B1 | 11/2001 | Allen et al. | |
| 6,335,267 B1 | 1/2002 | Iwamatsu et al. | |
| 6,354,516 B1 | 3/2002 | Patel et al. | |
| 6,534,018 B1 | 3/2003 | Baker et al. | |
| 6,543,443 B1 | 4/2003 | Klimowicz et al. | |
| 6,623,671 B2 | 9/2003 | Coe et al. | |
| 6,684,880 B2 | 2/2004 | Trueba | |
| 6,739,333 B1 | 5/2004 | Hoelz et al. | |
| 6,759,057 B1 | 7/2004 | Weiner et al. | |
| 6,770,291 B2 | 8/2004 | Smyth-Templeton et al. | |
| 6,855,296 B1 | 2/2005 | Baker et al. | |
| 6,890,555 B1 | 5/2005 | Desair et al. | |
| 7,958,887 B2 | 6/2011 | Kelliher et al. | |
| 8,414,915 B2 | 4/2013 | Cipolla et al. | |
| 8,539,945 B2 | 9/2013 | Solomon et al. | |
| 8,662,381 B2 | 3/2014 | Kaar et al. | |
| 8,689,785 B2 | 4/2014 | Wright et al. | |
| 2002/0168322 A1 | 11/2002 | Clark et al. | |
| 2003/0101991 A1* | 6/2003 | Trueba | A61M 15/0085 128/200.14 |
| 2003/0111088 A1 | 6/2003 | Fox | |
| 2004/0084044 A1 | 5/2004 | Childers et al. | |
| 2005/0066968 A1 | 3/2005 | Shofner et al. | |
| 2005/0081846 A1 | 4/2005 | Barney | |
| 2005/0133024 A1 | 6/2005 | Coifman | |
| 2005/0150488 A1 | 7/2005 | Dave | |
| 2005/0150489 A1 | 7/2005 | Dunfield et al. | |
| 2005/0166913 A1* | 8/2005 | Sexton | A61M 15/0065 128/200.14 |
| 2005/0196345 A1 | 9/2005 | Diederichs et al. | |
| 2005/0247312 A1 | 11/2005 | Davies | |
| 2005/0251289 A1 | 11/2005 | Bonney et al. | |
| 2005/0274378 A1 | 12/2005 | Bonney et al. | |
| 2007/0093786 A1 | 4/2007 | Goldsmith et al. | |
| 2007/0157931 A1 | 7/2007 | Parker | |
| 2007/0240712 A1 | 10/2007 | Fleming et al. | |
| 2008/0138397 A1 | 6/2008 | Schuster et al. | |
| 2008/0139910 A1 | 6/2008 | Mastrototaro | |
| 2008/0308101 A1 | 12/2008 | Spandorfer | |
| 2010/0121163 A1 | 5/2010 | Vestel | |
| 2011/0182831 A1 | 7/2011 | Gonda | |
| 2012/0136270 A1 | 5/2012 | Leuthardt et al. | |
| 2012/0183949 A1 | 7/2012 | Hyde et al. | |
| 2012/0282328 A1 | 11/2012 | Cipolla et al. | |
| 2012/0305011 A1 | 12/2012 | Gonda | |
| 2013/0104624 A1 | 5/2013 | Devine | |
| 2013/0112199 A1 | 5/2013 | Von Schuckmann et al. | |
| 2013/0186398 A1 | 7/2013 | Baillet et al. | |
| 2013/0206141 A1 | 8/2013 | Thoemmes et al. | |
| 2014/0007873 A1 | 1/2014 | Smutney et al. | |
| 2014/0007874 A1 | 1/2014 | Ellwanger et al. | |
| 2014/0014105 A1 | 1/2014 | Berenshteyn et al. | |
| 2014/0053838 A1 | 2/2014 | Berenshteyn et al. | |
| 2014/0053839 A1 | 2/2014 | Nakamura et al. | |
| 2014/0083421 A1 | 3/2014 | Smutney et al. | |
| 2014/0190496 A1 | 7/2014 | Wensley et al. | |
| 2014/0243749 A1 | 8/2014 | Edwards | |
| 2014/0251330 A1 | 9/2014 | Collins et al. | |
| 2014/0365142 A1 | 12/2014 | Baldwin | |
| 2015/0122257 A1 | 5/2015 | Winkler et al. | |
| 2015/0196060 A1 | 7/2015 | Wensley et al. | |
| 2015/0245661 A1 | 9/2015 | Milin | |
| 2017/0106153 A1 | 4/2017 | Davidson et al. | |

FOREIGN PATENT DOCUMENTS

| | | |
|---|---|---|
| JP | 2005533583 A | 11/2005 |
| JP | 2009532189 A | 9/2009 |
| WO | WO 2014/068504 A2 | 5/2014 |

OTHER PUBLICATIONS

European Patent Office, Extended European Search Report, Pursuant to Rule 62 EPC; App. No. EP 15831963.2; dated Mar. 27, 2018; pp. 1-7.

"Evaluating Transdermal Alcohol Measuring Devices: Final Report"; U.S. Department of Transportation; Nov. 2007, pp. i-87; National Highway Traffic Safety Administration (NHTSA).

"Guidelines for Spray Nozzle Selection"; Spraying Systems Co.; www.spray.com; 2014, p. 1-4.

"Merck Index"; Merck and Co., 2001, 13$^{th}$ edition; Whitehouse Station, NJ, USA.

"Physicians' Desk Reference"; Thomson PDR, 2004. 58th edition; Montvale, NJ, USA.

Bhalaria, M.K.; Naik, Sachin; Misra, A.N.; "Ethosomes: A novel delivery system for antifungal drugs in the treatment of topical fungal diseases"; Indian Journal of Experimental Biology; May 2009, p. 368-375, vol. 47; India.

Coates, Matthew S.; Chan, Ham-Kin; Fletcher, David F.; Raper, Judy A.; "Effect of Design on the Performance of a Dry Powder Inhaler Using Computational Fluid Dynamics"; Journal of Pharmaceutical Sciences, Jun. 2006, p. 1382-1392, vol. 95, No. 6; USA.

Copley, Mark; "Assessing dry powder inhalers"; Copley Science; Jan. 2010; p. 1-8; USA.

Dave, Vivek; Kumar, Dhirendra; Lewis, Shaila; Paliwal, Sarvesh; "Ethosome for Enhanced Transdermal Drug Delivery of Aceclofenac"; International Journal of Drug Delivery; 2010, p. 81-92; http://www.arjounrals.org/ijdd.html.

Newman, Stephen P., Phd; "Principles of Metered-Dose Inhaler Design"; Respiratory Care, Sep. 2005, p. 1177-1190, vol. 50 No. 9; USA.

Nielsen, K.G.; Skov, M.; Klug, B.; Ifversen, M.; Bisgaard, H.; "Flow-dependent effect of formoterol dry-powder inhaled from the Aerolizer®"; European Respiratory Journal; 1997, p. 2105-2109, vol. 10; United Kingdom.

Sheth, Ketan K., MD., MBA.; George, Maureen R., MSN., RN., CS.; Kelly, H. William, Pharmd; "Dry Powder Inhalers In the Treatment of Asthma: A continuing education monograph for physicians, nurses, pharmacists, physician assistants, and respiratory therapists."; Meniscus Limited; 2002; USA.

Terzano, C.; "Metered dose inhalers and spacer devices"; European Review for Medical and Pharmacological Sciences; 1999, p. 159-169, vol. 3; Department of Cardiovascular and Respiratory Sciences, "La Sapienza" University; Rome, Italy.

Troy, David B.; Beringer, Paul; "Remington: The Science and Practice of Pharmacy"; Lippincott, Williams & Wilkins; 2000, 20$^{th}$ edition; Baltimore, MD, USA.

Webster, Gregory D.; Gabler, Hampton C.; "Feasibility of Transdermal Ethanol Sensing For the Detection of Intoxicated Drivers";

(56) References Cited

OTHER PUBLICATIONS

Center for Injury Biomechanics; Oct. 2007, pp. 449-464; Virginia Polytechnic and State University; Blackburg, VA, USA.
Chinese State Intellectual Property Office, Notification of the First Office Action, App. No. 201580055212.2 (based on PCT App. No. PCT/US2015/044773); dated Jun. 28, 2019; pp. 1-6 (machine translation provided).
Chinese State Intellectual Property Office, Notification of the Second Office Action, App. No. 201580055212.2 (based on PCT App. No. PCT/US2015/044773); dated Mar. 19, 2020; pp. 1-7 (machine translation provided).

* cited by examiner

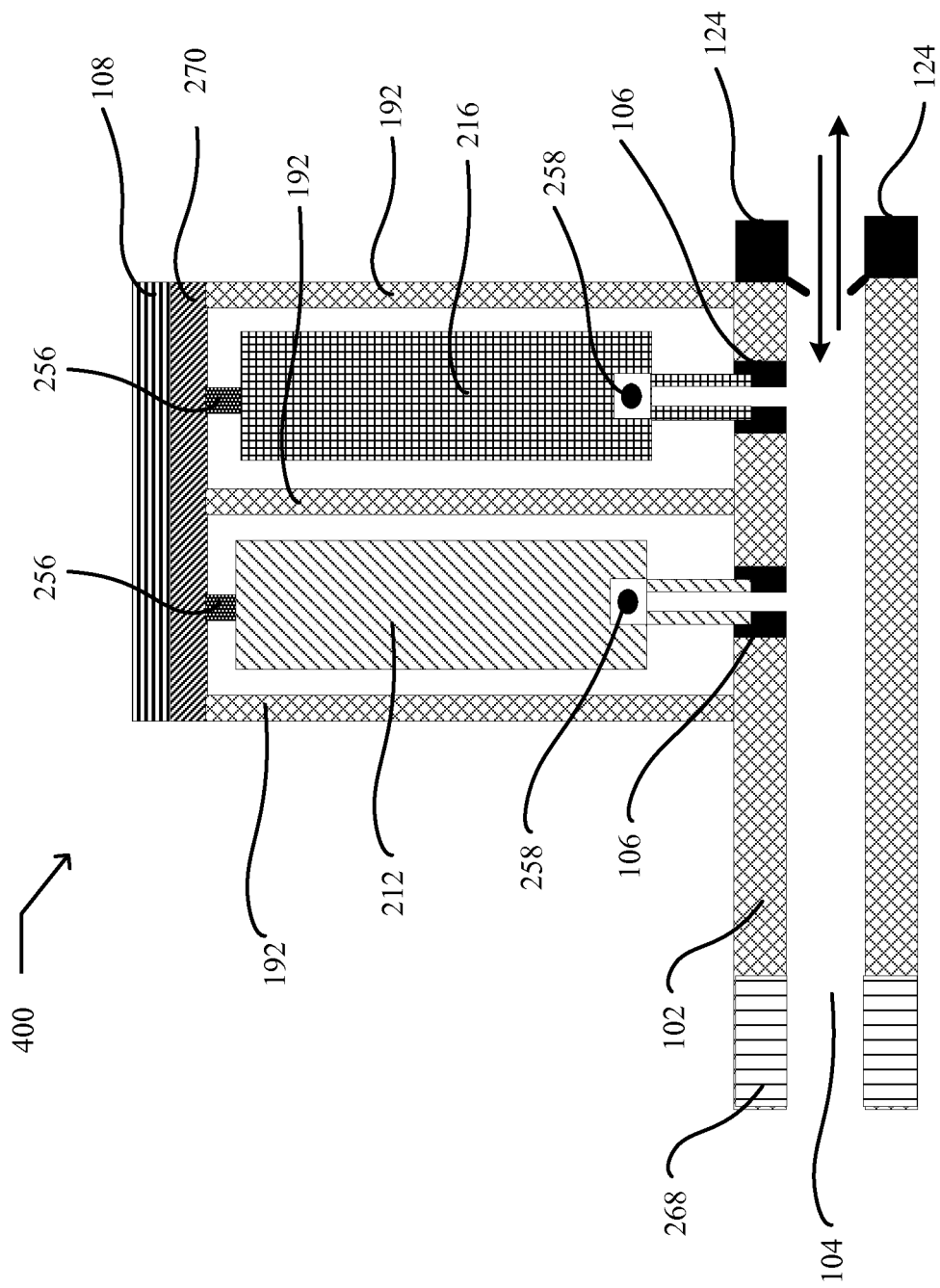

SYSTEMS, METHODS, AND DEVICES TO INCENTIVIZE INHALER USE

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)). In addition, the present application is related to the "Related Applications," if any, listed below.

PRIORITY APPLICATIONS

For purposes of the USPTO extra-statutory requirements, the present application constitutes a continuation of U.S. patent application Ser. No. 14/459,075, entitled SYSTEMS, METHODS, AND DEVICES TO INCENTIVIZE INHALER USE, naming Jesse R. Cheatham, III, Roderick A. Hyde, Robert C. Petroski, Lowell L. Wood, Jr., and Victoria Y. H. Wood as inventors, filed 13 Aug. 2014, which is currently co-pending or is an application of which a currently co-pending application is entitled to the benefit of the filing date.

RELATED APPLICATIONS

For purposes of the USPTO extra-statutory requirements, the present application is related to U.S. patent application Ser. No. 14/549,381, entitled SYSTEMS, METHODS, AND DEVICES TO INCENTIVIZE INHALER USE, naming Jesse R. Cheatham, III, Roderick A. Hyde, Robert C. Petroski, Lowell L. Wood, Jr., and Victoria Y. H. Wood as inventors, filed Nov. 20, 2014, which is currently co-pending.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In one aspect, an inhaler includes, but is not limited to, a housing having at least one flow channel disposed therein; at least one port disposed in the housing and operably coupled to the at least one flow channel and configured to provide fluid communication between at least two agent containing reservoirs and the at least one flow channel; one or more sensors operably coupled with the at least one flow channel; at least one actuator configured to independently facilitate at least partial release of at least one agent from each of at least two agent containing reservoirs when the at least two agent containing reservoirs are each operably coupled to the at least one port; and one or more control units configured to receive information from the one or more sensors, wherein the one or more control units control operation of the at least one actuator in response to the information received from the one or more sensors. In some embodiments, an inhaler may optionally include at least one reservoir. In some embodiments, an inhaler may optionally include one or more dose counters. In some embodiments, an inhaler may optionally include one or more performance indicators. In addition to the foregoing, other inhaler aspects are described in the claims, drawings, and text forming a part of the present disclosure.

In one aspect, a method includes, but is not limited to, assessing one or more parameters associated with use of an inhaler by a subject, administering at least one active agent to the subject in response to assessing the one or more parameters associated with use of the inhaler, and administering at least one incentive agent to the subject in coordination with administering the at least one active agent. In some embodiments, the method may optionally include displaying a comparison of an assessed value associated with one or more respiration parameters with one or more levels associated with the one or more respiration parameters. In some embodiments, the method may optionally include instructing the subject to achieve one or more values associated with one or more respiration parameters. In some embodiments, the method may optionally include accepting information associated with one or more parameters associated with the subject. In some embodiments, the method may optionally include administering at least one additional agent to the subject. In some embodiments, the method may optionally include assessing one or more parameters associated with administering the at least one active agent to the subject. In some embodiments, the method may optionally include assessing one or more parameters associated with administering the at least one incentive agent to the subject. In some embodiments, the method may optionally include predicting one or more locations in the pulmonary tract of the subject where the at least one active agent was delivered in response to the one or more parameters associated with administration of the at least one active agent to the subject. In some embodiments, the method may optionally include predicting one or more locations in the pulmonary tract of the subject where the at least one incentive agent was delivered in response to the one or more parameters associated with administration of the at least one incentive agent to the subject. In addition to the foregoing, other method aspects are described in the claims, drawings, and text forming a part of the present disclosure.

In one aspect, a system includes, but is not limited to, circuitry configured to assess one or more parameters associated with use of an inhaler by a subject, circuitry configured to administer at least one active agent to the subject in response to assessing the one or more parameters associated with use of the inhaler, and circuitry configured to administer at least one incentive agent to the subject in coordination with administering the at least one active agent. In some embodiments, the system may optionally include circuitry configured to display a comparison of an assessed value associated with one or more respiration parameters with one or more threshold levels associated with the one or more respiration parameters. In some embodiments, the system may optionally include circuitry configured to instruct the subject to achieve one or more values associated with one or more respiration parameters. In some embodiments, the system may optionally include circuitry configured to accept information associated with one or more parameters associated with the subject. In some embodiments, the system may optionally include circuitry configured to assess one or more parameters associated with administering the at least one active agent to the subject. In some embodiments, the system may optionally include circuitry configured to assess one or more parameters associated with administering the at least one incentive agent to the subject. In some embodiments, the system may optionally include circuitry configured to predict one or more locations in the pulmonary tract of the subject where the at least one active agent was delivered in response to one or more parameters associated with administration of the at least one active agent to the subject. In some embodiments, the system may optionally include circuitry configured to predict one or more locations in the pulmonary tract of the subject where the at least one incentive agent was delivered in response to one or more parameters associated with administration of the at least one incentive agent to the subject. In addition to the foregoing, other system aspects are described in the claims, drawings, and text forming a part of the present disclosure.

In one aspect, a system includes, but is not limited to, means for assessing one or more parameters associated with use of an inhaler by a subject, means for administering at least one formulation to the subject in response to assessing the one or more parameters associated with use of the inhaler, and means for administering at least one incentive agent to the subject in coordination with administering the at least one active agent. In some embodiments, the system may optionally include means for displaying a comparison of an assessed value associated with one or more respiration parameters with one or more levels associated with the one or more respiration parameters. In some embodiments, the system may optionally include means for instructing the subject to achieve one or more values associated with one or more respiration parameters. In some embodiments, the system may optionally include means for accepting information associated with one or more parameters associated with the subject. In some embodiments, the system may optionally include means for assessing one or more parameters associated with administering the at least one active agent to the subject. In some embodiments, the system may optionally include means for assessing one or more parameters associated with administering the at least one incentive agent to the subject. In some embodiments, the system may optionally include means for predicting one or more locations in the pulmonary tract of the subject where the at least one active agent was delivered in response to one or more parameters associated with administration of the at least one active agent to the subject. In some embodiments, the system may optionally include means for predicting one or more locations in the pulmonary tract of the subject where the at least one incentive agent was delivered in response to one or more parameters associated with administration of the at least one incentive agent to the subject. In addition to the foregoing, other system aspects are described in the claims, drawings, and text forming a part of the present disclosure.

In one aspect, a system includes, but is not limited to, a non-transitory signal-bearing medium bearing one or more instructions that, when executed by one or more processing components, direct performance of operations that include at least: assessing one or more parameters associated with use of an inhaler by a subject; administering at least one active agent to the subject in response to assessing the one or more parameters associated with use of the inhaler; and administering at least one incentive agent to the subject in coordination with administering the at least one active agent. In some embodiments, a system may optionally include one or more instructions that direct performance of an operation that includes at least displaying a comparison of an assessed value associated with one or more respiration parameters with one or more levels associated with the one or more respiration parameters. In some embodiments, a system may optionally include one or more instructions that direct performance of an operation that includes at least instructing the subject to achieve one or more values associated with one or more respiration parameters. In some embodiments, a system may optionally include one or more instructions that direct performance of an operation that includes at least accepting information associated with one or more parameters associated with the subject. In some embodiments, a system may optionally include one or more instructions that direct performance of an operation that includes at least assessing one or more parameters associated with administering the at least one active agent to the subject. In some embodiments, a system may optionally include one or more instructions that direct performance of an operation that includes at least assessing one or more parameters associated with administering the at least one incentive agent to the subject. In some embodiments, a system may optionally include one or more instructions that direct performance of an operation that includes at least predicting one or more locations in the pulmonary tract of the subject where the at least one active agent was delivered in response to the one or more parameters associated with administration of the at least one active agent to the subject. In some embodiments, a system may optionally include one or more instructions that direct performance of an operation that includes at least predicting one or more locations in the pulmonary tract of the subject where the at least one incentive agent was delivered in response to the one or more parameters associated with administration of the at least one incentive agent to the subject. In some embodiments, a system may optionally include a non-transitory signal-bearing medium that includes at least a computer-readable medium. In some embodiments, a system may optionally include a non-transitory signal-bearing medium that includes at least a recordable medium. In some embodiments, a system may optionally include a non-transitory signal-bearing medium that includes at least a communications medium. In addition to the foregoing, other system aspects are described in the claims, drawings, and text forming a part of the present disclosure.

In one or more various aspects, means include but are not limited to circuitry and/or programming for effecting the herein referenced functional aspects; the circuitry and/or programming can be virtually any combination of hardware, software, and/or firmware configured to effect the herein referenced functional aspects depending upon the design choices of the system designer. In addition to the foregoing, other system aspects means are described in the claims, drawings, and/or text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein referenced method aspects depending upon the design choices of the system designer. In addition to the foregoing, other system aspects are described in the claims, drawings, and/or text forming a part of the present application.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIG. 4 illustrates a cross-sectional partial side view of an example inhaler 400 in which embodiments may be implemented.

DETAILED DESCRIPTION

Figure 1:
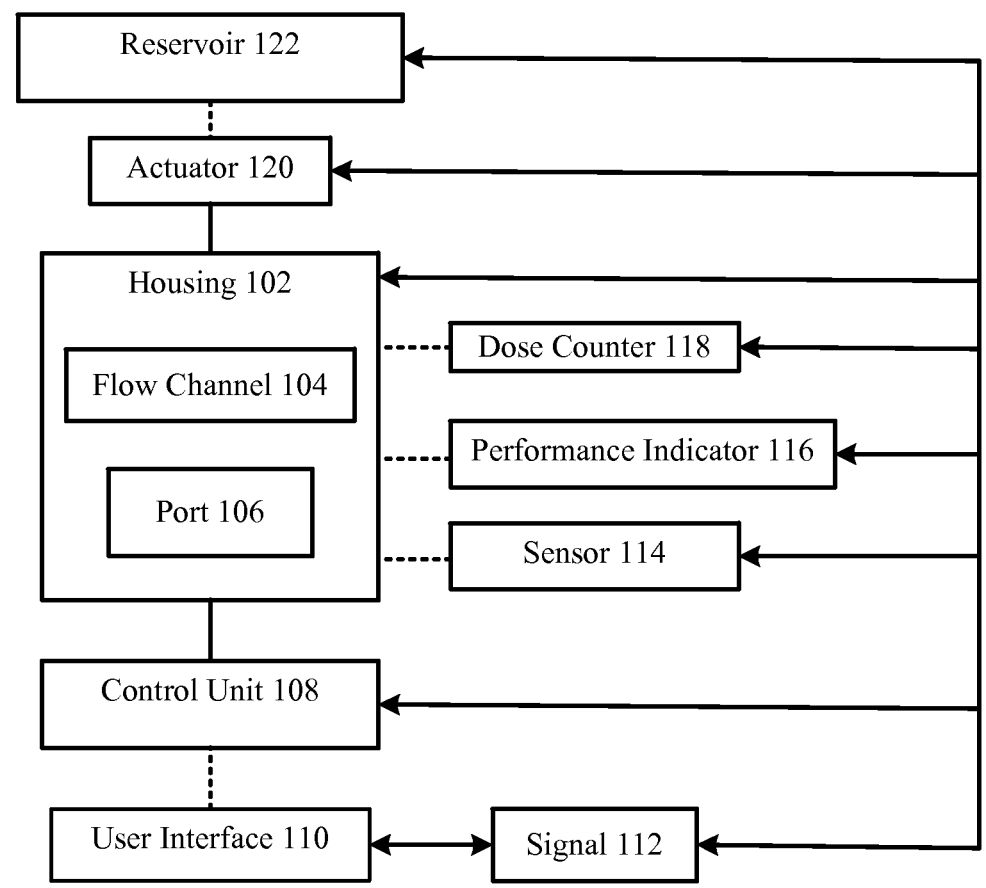
FIG. 1 illustrates an example system 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates an example system 100 in which numerous embodiments may be implemented. In some embodiments, system 100 may be implemented as an inhaler. In some embodiments, system 100 may include a housing 102 having at least one flow channel 104 disposed therein. In some embodiments, system 100 may include at least one port 106 disposed in the housing 102 and operably coupled to at least one flow channel 104 and configured to provide fluid communication between at least two reservoirs 122 and at least one flow channel 104. In some embodiments, system 100 may include one or more actuators 120. In some embodiments, system 100 may include one or more reservoirs 122. In some embodiments, system 100 may include one or more dose counters 118. In some embodiments, system 100 may include one or more performance indicators 116. In some embodiments, system 100 may include one or more control units 108. In some embodiments, system 100 may include one or more sensors 114. In some embodiments, system 100 may include one or more user interfaces 110. In some embodiments, system 100 may include one or more signals 112.

Figure 2:
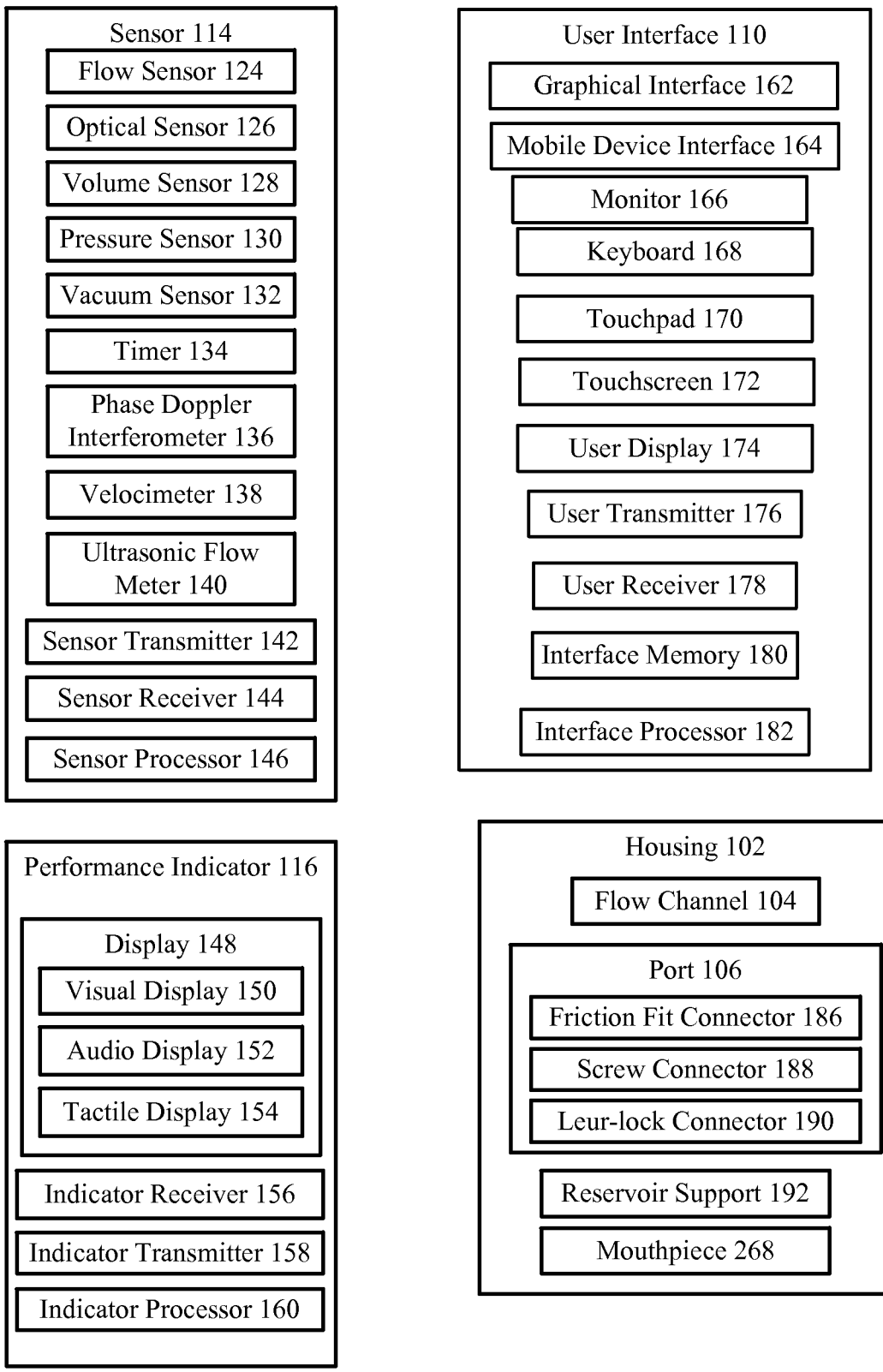
FIG. 2 illustrates example components of system 100 in which embodiments may be implemented.

FIG. 2 illustrates example embodiments of components that may be included in system 100. The illustrated components include a sensor 114, a performance indicator 116, a user interface 110, and a housing 102.

Figure 3:
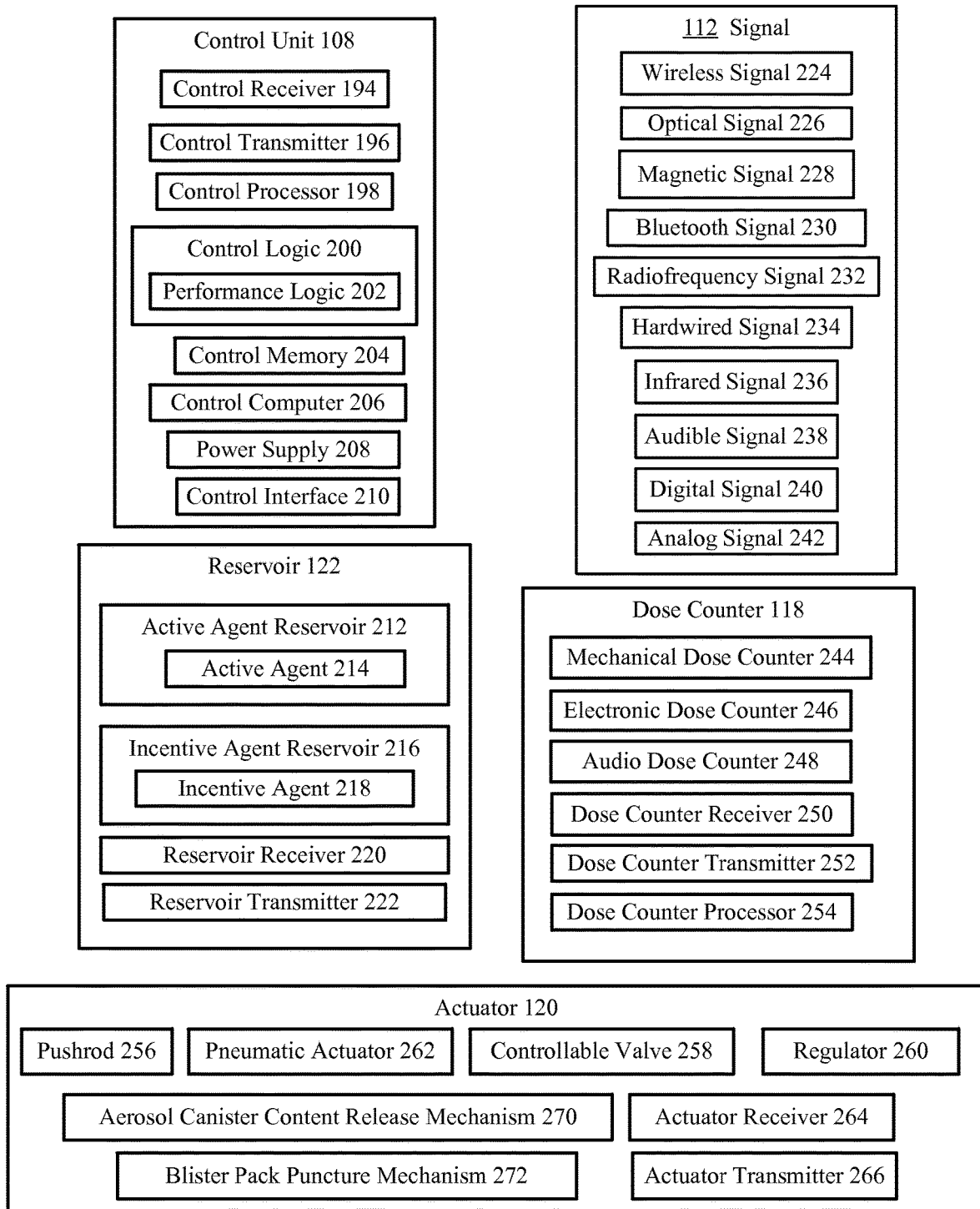
FIG. 3 illustrates example components of system 100 in which embodiments may be implemented.

FIG. 3 illustrates example embodiments of components that may be included in system 100. The illustrated components include a control unit 108, a signal 112, a dose counter 118, an actuator 120, and a reservoir 122.

Housing

With reference to FIGS. 1-3, in some embodiments, system 100 may include one or more housings 102. A housing 102 may be configured in numerous ways. In some embodiments, a housing may be configured for inclusion within an inhaler. In some embodiments, a housing 102 may include one or more flow channels 104 disposed therein. In some embodiments, a housing 102 may include a single flow channel 104 disposed therein. In some embodiments, a housing 102 may include a plurality of flow channels 104 disposed therein. For example, in some embodiments, a housing 102 may include a first flow channel 104 disposed therein that is configured to direct an active agent 214 to a subject using the inhaler, and a second flow channel 104 disposed therein that is configured to direct an incentive agent 218 to the subject.

In some embodiments, a housing 102 may include one or more ports 106 disposed therein. In some embodiments, a housing 102 may include at least one port 106 disposed within the housing 102 and operably coupled to at least one flow channel 104 and configured to provide fluid communication between at least two reservoirs 122 and at least one flow channel 104. Accordingly, in some embodiments, a port 106 may be configured to operably couple with one or more reservoirs 122 and direct contents released from the one or more reservoirs 122 into one or more flow channels 104 disposed within a housing 102. In some embodiments, a port 106 may be configured to facilitate delivery of one or more powdered active agents 214 from an active agent reservoir 212 into a flow channel 104. In some embodiments, a port 106 may be configured to facilitate delivery of one or more powdered incentive agents 218 from an incentive agent reservoir 216 into a flow channel 104. In some embodiments, a port 106 may be aligned with an actuator 120 that is configured to propel a powdered formulation into a flow channel 106. For example, in some embodiments, a port 106 may be configured to allow a pushrod actuator 256 to pass through the port 106 in order to propel a powdered formulation from a reservoir 122 into a flow channel 104. In some embodiments, a port 106 may be configured to facilitate delivery of one or more aerosolized formulations from a reservoir 122 into a flow channel 104. For example, in some embodiments, a port 106 may be configured to operably couple with an aerosol canister that includes a canister body and a valve stem that extends from the canister body and into a port 106 that is aligned with a flow channel 104. In some embodiments, a housing 102 may include at least one port 106 disposed in the housing 102 and operably coupled to at least one flow channel 104 and configured to receive one or more reservoirs 122. In some embodiments, a housing 102 may include two or more ports 106 disposed within the housing 102 that are each operably coupled to at least one flow channel 104 and are each configured to receive a reservoir 122. In some embodiments, a housing 102 may include one port 106 disposed in the housing 102 that is operably coupled to at least one flow channel 104 and configured to receive two or more reservoirs 122. A port 106 may include numerous types of connectors that allow one or more reservoirs 122 to be operably coupled to the port 106. Examples of such connectors include, but are not limited to, friction fit connectors 186, screw connectors 188, Leur-lock connectors 190, and the like. In some embodiments, a port 106 may include an actuator 120 that is operable to facilitate at least partial release of contents from one or more operably coupled reservoirs 122. For example, in some embodiments, a port 106 may include a controllable valve 258 that may be opened and closed to facilitate at least partial release of contents from an operably coupled reservoir 122. In some embodiments, such a controllable valve 258 may be operably coupled with a control unit 108 that is configured to control the operation of the controllable valve 258. In some embodiments, such a controllable valve 258 may be operably coupled with a sensor 114. In some embodiments, such a controllable valve 258 may be operably coupled with a sensor 114 that is configured to control the operation of the controllable valve 258. In some embodiments, such a controllable valve 258 may be operably coupled with a control unit 108 and a sensor 114 that are configured to control operation of the controllable valve 258. Accordingly, a port 106 may be configured in numerous ways.

In some embodiments, a housing 102 may include at least one reservoir support 192. For example, in some embodiments, a housing 102 may include at least one reservoir support 192 that is configured to support at least one aerosol canister that includes a canister body and a valve stem that extends from the canister body with the valve stem being receivable by a port 106. In some embodiments, a housing 102 may include at least one reservoir support 192 that is configured to support at least one reservoir 122 that includes a conveyor with at least one conveying drive configured to advance a blister strip that includes a plurality of blister packs that are filled with an active agent 214 or an incentive agent 218.

In some embodiments, a housing 102 may include at least one mouthpiece 268 that is operably coupled with one or more flow channels 104. In some embodiments, a mouthpiece 268 may be operably coupled with one or more sensors 114. A mouthpiece 268 may be operably coupled with numerous types of sensors 114. Examples of such sensors 114 include, but are not limited to, optical sensors 126, volume sensors 128, pressure sensors 130, vacuum sensors 132, timers 134, phase Doppler interferometers 136, velocimeters 138, ultrasonic flow meters 140, and the like. In some embodiments, a mouthpiece 268 may include a sensor 14 that is configured to assess the quality of physical contact between the mouth of a subject and the mouthpiece 268. For example, in some embodiments, a pressure sensor (e.g., strain gauge, stress gauge, deformation sensor, and the like) may be configured to assess the quality of physical contact between the mouth of a subject and the mouthpiece 268.

Reservoir

With continued reference to FIGS. 1-3, in some embodiments, system 100 may include one or more reservoirs 122. A reservoir 122 may be configured in numerous ways. In some embodiments, a reservoir 122 may include one or more reservoir receivers 220. In some embodiments, a reservoir 122 may include one or more reservoir transmitters 222. Accordingly, in some embodiments, a reservoir 122 may transmit one or more signals 112. In some embodiments, a reservoir 122 may receive one or more signals 112.

In some embodiments, a reservoir 122 may be operably coupled with a control unit 108. In some embodiments, a reservoir 122 may be operably coupled with a control unit 108 that controls operation of the reservoir 122. For example, in some embodiments, a control unit 108 may direct an active agent reservoir 212 that includes a conveyor with at least one conveying drive to advance a blister strip that includes a plurality of blister packs that are filled with a powdered active agent 214. In some embodiments, a reservoir 122 may be operably coupled with a sensor 114. In some embodiments, a reservoir 122 may be operably coupled with a sensor 114 that controls operation of the reservoir 122. For example, in some embodiments, a sensor 114 may detect a quantity of an active agent 214 released from an active agent reservoir 212 and then direct a conveying drive in an active agent reservoir 212 to advance a blister strip that includes a plurality of blister packs that are filled with a powdered active agent 214. In some embodiments, an active agent reservoir 122 may be operably coupled with a sensor 114 that detects a quantity of active agent 214 contained within the active agent reservoir 212. In some embodiments, an incentive agent reservoir 216 may be operably coupled with a sensor 114 that detects a quantity of an incentive agent 218 contained within the incentive agent reservoir 216. In some embodiments, an active agent reservoir 212 may be operably coupled with a sensor 114 that detects a quantity of an active agent 214 contained within the active agent reservoir 212 and a dose counter 118 that displays the amount of active agent 214 contained within the active agent reservoir 212. In some embodiments, an incentive agent reservoir 216 may be operably coupled with a sensor 114 that detects a quantity of an incentive agent 218 contained within the incentive agent reservoir 216 and a dose counter 118 that displays the amount of the incentive agent 218 contained within the incentive agent reservoir 216.

An active agent reservoir 212 may contain numerous types of active agents 214. Examples of such active agents 214 include, but are not limited to, steroids, anti-inflammatory drugs, bronchodilators, leukotriene modifiers, long-acting beta antagonists, 1,3-dimethylxanthine, short-acting beta agonists, [8-methyl-8-(1-methylethyl)-8-azoniabicyclo[3.2.1]oct-3-yl]3-hydroxy-2-phenyl-propanoate, antibodies, and the like (see e.g., *Remingtion: The Science and Practice of Pharmacy*, Lippincott, Williams & Wilkins, 20th edition, Baltimore, Md., USA (2000), *Physicians' Desk Reference*, Thomson PDR, 58th edition, Montvale, N.J. (2004); *Merck Index*, Merck and Co., 13th edition, Whitehouse Station, N.J. (2001); which are hereby incorporated by reference).

An incentive agent reservoir 216 may contain numerous types of incentive agents 218. Examples of such incentive agents 218 include, but are not limited to, flavoring agents, nicotine, ethanol, caffeine, and the like.

Active agents 214 and incentive agents 218 may be included in numerous types of formulations. In some embodiments, a formulation may be a liquid formulation. Accordingly, in some embodiments, a formulation may include a carrier fluid. In some embodiments, a formulation may be an aerosolized formulation. In some embodiments, a formulation may be a powdered formulation. In some embodiments, a formulation may be a powdered inhalation formulation. Accordingly, in some embodiments, a formulation may include a carrier powder. In some embodiments, a formulation may include one active agent 214. In some embodiments, a formulation may include more than one active agent 214. Accordingly, in some embodiments, a formulation may include numerous combinations of active agents 214. In some embodiments, a formulation may include one incentive agent 218. In some embodiments, a formulation may include more than one incentive agent 218. Accordingly, in some embodiments, a formulation may include numerous combinations of incentive agents 218.

In some embodiments, a reservoir 122 may be configured to contain a liquid formulation. For example, in some embodiments, an active agent reservoir 212 may be configured as an aerosol canister that includes a canister body and a valve stem that extends from the canister body. In some embodiments, contents may be at least partially released from an aerosol canister by depressing the valve stem relative to the canister body. In some embodiments, a reservoir 122 may be configured to contain a powdered formulation. For example, in some embodiments, an active agent reservoir 212 may include a conveyor with at least one conveying drive configured to advance a blister strip that includes a plurality of blister packs that are filled with a powdered active agent 214. In some embodiments, an incentive agent reservoir 216 may contain an incentive agent 218. In some embodiments, an incentive agent reservoir 216 may be configured to contain an incentive agent 218 that is in a liquid carrier. In some embodiments, an incentive agent reservoir 216 may be configured to contain an incentive agent 218 that is in powdered form.

Actuator

With continued reference to FIGS. 1-3, in some embodiments, system 100 may include one or more actuators 120. System 100 may include numerous types of actuators 120 and combinations of actuators 102. In some embodiments, an actuator 120 may be configured to facilitate at least partial release of contents from one or more reservoirs 122. For example, in some embodiments, an actuator 120 may be configured to facilitate at least partial release of one or more active agents 214 from one or more active agent reservoirs 212. In some embodiments, an actuator 120 may be configured to facilitate at least partial release of one or more incentive agents 218 from one or more incentive agent reservoirs 216. Examples of actuators 120 include, but are not limited to, controllable valves 258, pushrod actuators 258, regulators 260, pneumatic actuators 262, and the like. In some embodiments, an actuator 120 may be configured as an aerosol canister content release mechanism 270 that includes a pushrod actuator 256 that can depress an aerosol canister to open a controllable valve 258 and release contents of the aerosol canister. In some embodiments, an actuator 256 may be configured as a blister pack puncture mechanism 270 that includes a pushrod actuator 256 that can puncture a blister pack. In some embodiments, an actuator 120 may be configured as a blister pack puncture mechanism that includes a pushrod actuator 256 that can puncture a blister pack and propel a powdered inhalation formulation 214 from the blister pack into the at least one flow channel 104.

In some embodiments, an actuator 120 may include one or more actuator receivers 264. In some embodiments, an actuator 120 may include one or more actuator transmitters 266. Accordingly, in some embodiments, an actuator 120 may transmit one or more signals 112. In some embodiments, an actuator 120 may receive one or more signals 112. In some embodiments, an actuator 120 may be operably coupled to one or more sensors 114. Accordingly, in some embodiments, an actuator 120 may be controlled in response to one or more parameters that are detected by one or more sensors 114. For example, in some embodiments, a sensor 114 may detect a quantity of an active agent 214 flowing through a flow channel 104 and control the operation of one or more operably coupled actuators 120 in response to the amount of active agent 214 detected. In some embodiments, a sensor 114 may detect a quantity of an incentive agent 218 flowing through a flow channel 104 and control the operation of one or more operably coupled actuators 120 in response to the amount of incentive agent 218 detected. In some embodiments, a sensor 114 may detect when a subject using an inhaler is inhaling and activate one or more operably coupled actuators 120 to facilitate at least partial release from a reservoir 122 during the inhalation cycle. In some embodiments, a sensor 114 may detect when a subject using an inhaler is exhaling and deactivate one or more operably coupled actuators 120 to halt release from a reservoir 122 during the exhalation cycle. In some embodiments, a sensor 114 may detect when a subject using an inhaler is holding their breath and deactivate one or more operably coupled actuators 120 to halt release from a reservoir 122 during the breath holding cycle.

Dose Counter

As further shown in FIGS. 1-3, in some embodiments, system 100 may include one or more dose counters 118. Dose counters 118 may be configured in numerous ways. In some embodiments, a dose counter 118 may include one or more dose counter receivers 250. In some embodiments, a dose counter 118 may include one or more dose counter transmitters 252. Accordingly, in some embodiments, a dose counter 118 may transmit one or more signals 112. In some embodiments, a dose counter 118 may receive one or more signals 112.

In some embodiments, a dose counter 118 may be a mechanical dose counter 244. For example, in some embodiments, a mechanical dose 244 counter may include a ratchet mechanism that advances a numerical indicator every time that an inhaler is activated to dispense either or both of an active agent 214 and an incentive agent 218 (e.g., Wright et al., Dispending apparatus, U.S. Pat. No. 8,689,785 and Kaar et al., Dose counter for a metered-dose inhaler, U.S. Pat. No. 8,662,381; herein incorporated by reference). In some embodiments, a dose counter 118 may be an electronic dose counter 246 that includes an electronic display that displays the number of times that an inhaler is activated to dispense either or both of an active agent 214 and an incentive agent 218 (e.g., Solomon et al., Dose counter and recording method, U.S. Pat. No. 8,539,945; herein incorporated by reference). In some embodiments, a dose counter 118 may be an audio dose counter 248 that includes an audio display. In some embodiments, an audio display may be configured to indicate the number of times that an inhaler is activated to dispense either one or both of an active agent 214 and an incentive agent 218. For example, in some embodiments, an audio dose counter 248 may receive information associated with the number of times that an inhaler has been activated to release either one or both of an active agent 214 and an incentive agent 218 and provide an audio display in the form of a human voice to report the information.

In some embodiments, a dose counter 118 may be operably coupled with and receive information from one or more sensors 114. In some embodiments, a dose counter 118 may be operably coupled with and receive information from one or more control units 108. In some embodiments, a dose counter 118 may receive information associated with the quantity of an active agent 214 or an incentive agent 218 that is contained within an active agent reservoir 212 or an incentive agent reservoir 216 and then display the information. In some embodiments, a dose counter 118 may receive information associated with the quantity of an active agent 214 or an incentive agent 218 that is released through one or more flow channels 104 and then display the information.

Performance Indicator

With continued reference to FIGS. 1-3, in some embodiments, system 100 may include one or more performance indicators 116. Performance indicators 116 may be configured in numerous ways. In some embodiments, a performance indicator 116 may include one or more indicator receivers 156. In some embodiments, a performance indicator 116 may include one or more indicator transmitters 158. Accordingly, in some embodiments, a performance indicator 116 may transmit one or more signals 112. In some embodiments, a performance indicator 116 may receive one or more signals 112. In some embodiments, a performance indicator 116 may include one or more indicator processors 160. Accordingly, in some embodiments, a performance indicator 116 may process information.

In some embodiments, a performance indicator 116 may include a display 148. A performance indicator 116 may include numerous types of displays 148. Examples of such displays 148 include, but are not limited to, visual displays 150, audio displays 152, tactile displays 154, and the like. Examples of visual displays 150 include, but are not limited to, electronic visual displays 150 such as active displays and passive displays. In some embodiments, a visual display 150 may be contained within a mobile device such as a cellular telephone, a personal digital assistant, a notepad computer, and the like. Accordingly, in some embodiments, a control unit 108 may be configured to transmit performance information that is received by and displayed on a mobile device. In some embodiments, a sensor 114 may be configured to transmit performance information that is received by and displayed on a mobile device. In some embodiments, performance information may be displayed on a head mounted display 148 such as an optical head-mounted display 148. In some embodiments, a performance indicator 116 may include a tactile display 154 that is configured to vibrate. For example, in some embodiments, a performance indicator 116 may vibrate with an intensity that is related to respiration performance, such as inhalation performance, breath hold performance, and/or exhalation performance of a subject using an inhaler. In some embodiments, a performance indicator 116 may include an audio display 152 that is configured to emit one or more sounds. For example, in some embodiments, a performance indicator 116 may have a tone that is related to respiration performance, such as inhalation performance, breath hold performance, and/or exhalation performance of a subject using an inhaler. In some embodiments, a performance indicator 116 may be configured to output a human voice that indicates a level of respiration performance, such as inhalation performance, breath hold performance, and/or exhalation performance of a subject using an inhaler. In some embodiments, a performance indicator 116 may be configured to output a human voice that instructs a subject to reach a level of respiration performance, such as inhalation performance, breath hold performance, and/or exhalation performance of a subject using an inhaler. A performance indicator 116 may display information that is related to numerous types of performance. For example, in some embodiments, a performance indicator 116 may indicate one or more flow levels of an active agent 214 through a flow channel 104. In some embodiments, a performance indicator 116 may indicate one or more levels of a vacuum that are applied to a flow channel 104 by a subject using the inhaler. In some embodiments, a performance indicator 116 may indicate a volume of gas flowing through a flow channel 104 during an inhalation cycle of a subject using an inhaler. In some embodiments, a performance indicator 116 may indicate a volume of gas flowing through a flow channel 104 during an exhalation cycle of a subject using an inhaler. In some embodiments, a performance indicator 116 may indicate a period of time related to how long a subject using an inhaler holds their breath. In some embodiments, a performance indicator 116 may indicate a velocity with which gas flows through a flow channel 104. For example, in some embodiments, a performance indicator 116 may indicate the velocity of gas flowing through a flow channel 104 during an inhalation cycle by a subject using the inhaler. In some embodiments, a performance indicator 116 may indicate the velocity of gas flowing through a flow channel 104 during an exhalation cycle by a subject using the inhaler. Accordingly, a performance indicator 116 may be configured to display information that is related to numerous parameters.

In some embodiments, a performance indicator 116 may be operably coupled with one or more control units 108. In some embodiments, a performance indicator 116 may be operably coupled with one or more sensors 114. In some embodiments, a performance indicator 116 may be operably coupled with one or more control units 108 and one or more sensors 114. In some embodiments, a performance indicator 116 may be configured to display processed information that is received from a control unit 108. For example, in some embodiments, a performance indicator 116 may indicate a quantity of an active agent 214 that flows through a flow channel 104. In some embodiments, a performance indicator 116 may indicate a quantity of an active agent 214 to be released to reach a predetermined dosage level.

Sensor

As further shown in FIGS. 1-3, in some embodiments, system 100 may include one or more sensors 114. System 100 may include numerous types of sensors 114. Examples of sensors 114 include, but are not limited to, flow sensors 124 such as gas flow sensors 124 and liquid flow sensors 124, volume sensors 128, optical sensors 126, pressure sensors 130, vacuum sensors 132, timers 134, phase Doppler interferometers 136, velocimeters 138, ultrasonic flow meters 140, and the like.

In some embodiments, a sensor 114 may include one or more sensor receivers 144. In some embodiments, a sensor 114 may include one or more sensor transmitters 142. In some embodiments, a sensor 114 may receive one or more signals 112. In some embodiments, a sensor 114 may transmit one or more signals 112. In some embodiments, a sensor 114 may include one or more sensor processors 146. Accordingly, in some embodiments, a sensor 114 may process information.

In some embodiments, one or more sensors 114 may be operably coupled with one or more flow channels 104 that are disposed within a housing 102. In some embodiments, a sensor 114 may be configured to measure the velocity with which gas flows through a flow channel 104. In some embodiments, a sensor 114 may be configured to measure the velocity with which liquid flows through a flow channel 104. In some embodiments, a volume sensor 128 may be used to measure a volume of gas flowing through a flow channel 104. In some embodiments, a volume sensor 128 may be used to measure a volume of liquid flowing through a flow channel 104. In some embodiments, a sensor 114 may be configured to measure a quantity of an active agent 214 that flows through a flow channel 104. In some embodiments, a vacuum sensor 132 may be used to measure an amount of vacuum pressure applied to a flow channel 104. In some embodiments, a pressure sensor 130 may be used to measure an amount of gas pressure applied to a flow channel 104. In some embodiments, a timer 134 may be configured to measure an amount of time related to a respiration parameter. For example, in some embodiments, a timer 134 may be used to determine a time period during one or more of an inhalation cycle, an exhalation cycle, or a breath hold cycle occurring during use of an inhaler. In some embodiments, a pressure sensor 130 may be operably coupled to a mouthpiece 268 of an inhaler and configured to assess the quality of physical contact between the mouth of a subject and the mouthpiece. Accordingly, in some embodiments, such a pressure sensor 130 may be configured to measure stress and/or strain on the mouthpiece 268.

In some embodiments, a sensor 114 may be operably coupled with one or more control units 108. Accordingly, in some embodiments, a control unit 108 may be configured to control the operation of one or more operably coupled sensors 114. In some embodiments, a sensor 114 may be operably coupled with one or more actuators 120 that are configured to facilitate at least partial release of contents from one or more reservoirs 122. For example, in some embodiments, a sensor 114 may be operably coupled to an actuator 120 and configured to facilitate at least partial release of one or more active agents 214 from an active agent reservoir 212 in a manner that is dependent on the quantity of an active agent 214 detected flowing through a flow channel 104. In some embodiments, a sensor 114 may be coupled to a control unit 108 and to an actuator 120. Accordingly, in some embodiments, a control unit 108 may receive detected information from one or more sensors 114 and then control one or more actuators 120 in response to the information.

User Interface

With continued reference to FIGS. 1-3, in some embodiments, system 100 may include one or more user interfaces 110. System 100 may include numerous types of user interfaces 110. Examples of user interfaces 110 include, but are not limited to, graphical interfaces 162, monitors 166, touchscreens 172, touchpads 170, keyboards 168, mobile device interfaces 164, and the like. In some embodiments, a user interface may include one or more user transmitters 176. In some embodiments, a user interface may include one or more user receivers 178. In some embodiments, a user interface may include one or more interface processors 182. Accordingly, in some embodiments, a user interface 110 may transmit one or more signals 112, receive one or more signals 112, and process one or more signals 112.

In some embodiments, a user interface 110 may transmit one or more signals 112 that are received by one or more control units 108. In some embodiments, a user interface 110 may transmit one or more signals 112 that are received by one or more sensors 114. In some embodiments, a user interface 110 may transmit one or more signals 112 that are received by one or more performance indicators 116. In some embodiments, a user interface 110 may transmit one or more signals 112 that are received by one or more dose counters 118. In some embodiments, a user interface 110 may transmit one or more signals 112 that are received by one or more actuators 120.

In some embodiments, a user interface 110 may receive one or more signals 112 that are transmitted by one or more control units 108. In some embodiments, a user interface 110 may receive one or more signals 112 that are transmitted by one or more sensors 114. In some embodiments, a user interface 110 may receive one or more signals 112 that are transmitted by one or more performance indicators 116. In some embodiments, a user interface 110 may receive one or more signals 112 that are transmitted by one or more dose counters 118.

In some embodiments, a subject may enter information into a user interface 110 that transmits one or more signals 112 that include the information that are received by one or more control units 108. Examples of such information include, but are not limited to, information related to a subject's height, weight, age, allergies, respiration parameters, physical fitness level, information related to one or more maladies associated with the subject, information related to drugs used by the subject, and the like.

Signal

Numerous types of signals 112 may be used within system 100. Examples of such signals 112 include, but are not limited to, wireless signals 224, optical signals 226, magnetic signals 228, radiofrequency signals 232, hardwired signals 234, infrared signals 236, audible signals 238, analog signals 242, digital signals 240, Bluetooth signals 230, and the like. Accordingly, system 100 may include receivers, transmitters, and processors that are configured to receive, transmit, and process numerous types of signals 112. A signal 112 may include numerous types of information. For example, in some embodiments, a signal 112 may include information associated with one or more respiration parameters. In some embodiments, a signal 112 may include information associated with release of one or more active agents 214 from an active agent reservoir 212. In some embodiments, a signal 112 may include information associated with release of one or more incentive agents 218 from an incentive agent reservoir 216.

Control Unit

As further depicted in FIGS. 1-3, in some embodiments, system 100 may include one or more control units 108. In some embodiments, a control unit 108 may include one or more control computers 206. In some embodiments, a control unit 108 may include one or more control receivers 194. In some embodiments, a control unit 108 may include one or more control transmitters 196. In some embodiments, a control unit 108 may include one or more control processors 198. In some embodiments, a control unit 108 may include control memory 204. In some embodiments, a control unit 108 may include control logic 200. In some embodiments, a control unit 108 may include performance logic 202. In some embodiments, a control unit 108 may include one or more power supplies 208. In some embodiments, a control unit 108 may include one or more control interfaces 210.

In some embodiments, a control unit 108 may receive one or more signals 112 that are transmitted by one or more user interfaces 110. In some embodiments, a control unit 108 may receive one or more signals 112 that are transmitted by one or more sensors 114. In some embodiments, a control unit 108 may receive one or more signals 112 that are transmitted by one or more performance indicators 116. In some embodiments, a control unit 108 may receive one or more signals 112 that are transmitted by one or more dose counters 118. In some embodiments, a control unit 108 may receive one or more signals 112 that are transmitted by one or more actuators 120.

In some embodiments, a control unit 108 may transmit one or more signals 112 that are received by one or more user interfaces 110. In some embodiments, a control unit 108 may transmit one or more signals 112 that are received by one or more sensors 114. In some embodiments, a control unit 108 may transmit one or more signals 112 that are received by one or more actuators 120. In some embodiments, a control unit 108 may transmit one or more signals 112 that are received by one or more performance indicators 116. In some embodiments, a control unit 108 may transmit one or more signals 112 that are received by one or more dose counters 118.

In some embodiments, a control unit 108 may transmit one or more signals 112 that direct the operation of one or more actuators 120. For example, in some embodiments, a control unit 108 may transmit one or more signals 112 that direct an actuator 120 to at least partially release contents from one or more reservoirs 122. In some embodiments, a control unit 108 may transmit one or more signals 112 that direct an actuator 120 not to release contents from one or more reservoirs 122. For example, in some embodiments, a control unit 108 may receive information from one or more sensors 114 that is related to inhalation and exhalation through a flow channel 104 by a subject using an inhaler. The control unit 108 may then direct one or more actuators 120 to at least partially release contents from one or more reservoirs 122 during an inhalation cycle through an inhaler and then direct the one or more actuators 120 to not release contents from the one or more reservoirs 122 during an exhalation cycle through an inhaler. In some embodiments, a control unit 108 may direct the operation of more than one actuator 120. For example, in some embodiments, a control unit 108 may direct a first actuator 120 to at least partially release an active agent 214 from an active agent reservoir 212 and then direct a second actuator 120 to at least partially release an incentive agent 218 from an incentive agent reservoir 216. In some embodiments, a control unit 108 may direct a first actuator 120 to at least partially release an incentive agent 218 from an incentive agent reservoir 216 and then direct a second actuator 120 to at least partially release an active agent 214 from an active agent reservoir 212. In some embodiments, a control unit 108 may direct a first actuator 120 to at least partially release an incentive agent 218 from an incentive agent reservoir 216 and direct a second actuator 120 to at least partially release an active agent 214 from an active agent reservoir 212 at substantially the same time.

In some embodiments, a control unit 108 may transmit one or more signals 112 that are received by one or more performance indicators 116. For example, in some embodiments, a control unit 108 may receive one or more signals 112 from a sensor 114 that include information related to respiration performance by a subject using an inhaler. The control unit 108 may then transmit one or more signals 112 that are received by a performance indicator 116 that direct the performance indicator 116 to indicate the level of assessed respiration performance. In some embodiments, a control unit 108 may receive one or more signals 112 from one or more sensors 114 that include information related to a quantity of an active agent 214 that flowed through a flow channel 104. In some embodiments, the control unit 108 may then transmit one or more signals 112 that are received by one or more performance indicators 116 that direct the one or more performance indicators 116 to indicate the quantity of the active agent 214 that flowed through a flow channel 104. In some embodiments, a control unit 108 may transmit one or more signals 112 that are received by one or more performance indicators 116 that direct the one or more performance indicators 116 to indicate a quantity of an active agent 214 that needs to be release from an active agent reservoir 212 to reach a predetermined dosage.

In some embodiments, a control unit 108 may receive one or more signals 112 that are transmitted by one or more dose counters 118. For example, in some embodiments, a control unit 108 may receive one or more signals 112 that include information related to the number of doses of an active agent 214 or an incentive agent 218 that have been released from an active agent reservoir 212 or an incentive agent reservoir 216. In some embodiments, a control unit 108 may receive one or more signals 112 that were transmitted by a dose counter 118 that include information related to the number of doses of an active agent 214 that are contained in an active agent reservoir 212. In some embodiments, a control unit 108 may receive one or more signals 112 that were transmitted by a dose counter 118 that include information related to the number of doses of an incentive agent 218 that are contained in an incentive agent reservoir 216.

In some embodiments, a control unit 108 may compare one or more parameters to one or more threshold levels that are associated with the one or more parameters. For example, in some embodiments, a control unit 108 may receive one or more assessed values from one or more sensors 114 that are associated with a volume of flow through one or more flow channels 104 disposed within an inhaler. The control unit 108 may compare the one or more assessed values to one or more threshold values that are associated with a volume of flow through a flow channel 104 to determine if the one or more assessed values meet or exceed the one or more threshold values. In some embodiments, a control unit 108 may compare one or more assessed values that are related to one or more parameters to one or more ranges of levels associated with the one or more parameters. In some embodiments, a control unit 108 may compare one or more assessed values that are related to one or more parameters to one or more ranges of levels associated with the one or more parameters to determine in the one or more assessed values are within the one or more ranges of levels associated with the one or more parameters. For example, in some embodiments, a control unit 108 may receive one or more signals 112 transmitted by one or more sensors 114 that include one or more assessed values associated with a volume of flow through one or more flow channels 104 disposed within an inhaler. The control unit 108 may compare the one or more assessed values to one or more ranges of values that are associated with a volume of flow through a flow channel to determine if the one or more assessed values are within the one or more ranges of values. Exemplary ranges of flow through one or more flow channels 104 disposed within an inhaler include, but are not limited to, about 5 liters per minute and about 200 liters per minute, about 30 liters per minute and about 150 liters per minute, about 50 liters per minute and about 100 liters per minute, about 20 liters per minute and about 60 liters per minute, about 30 liters per minute and about 50 liters per minute, about 50 liters per minute and about 200 liters per minute, about 75 liters per minute and about 200 liters per minute, about 100 liters per minute and about 200 liters, about 125 liters per minute and about 200 liters per minute, about 150 liters per minute and about 200 liters per minute, about 175 liters per minute and about 200 liters per minute, about 50 liters per minute and about 150 liters per minute, about 60 liters per minute and about 150 liters per minute, and about 60 liters per minute and about 120 liters per minute.

Numerous threshold values may be assigned to a parameter. In some embodiments, a threshold value may be determined based in the age of a subject using an inhaler. For example, in some embodiments, a threshold value associated with the velocity of flow through a flow channel 104 during an inhalation cycle of a child using an inhaler may be selected to provide for adequate delivery of an active agent 214 to the child. In some embodiments, a threshold value associated with the velocity of flow through a flow channel 104 during an inhalation cycle of an adult using an inhaler may be selected to provide for adequate delivery of a formulation 214 to the adult. Accordingly, threshold values may be selected with regard to numerous parameters. Examples of such parameters include, but are not limited to, age of a subject, identity of an active agent 214 that is to be delivered, location within the pulmonary tract where an active agent 214 is to be delivered, quantity of an active agent 214 that is to be delivered, and the like. Accordingly, a control unit may compare numerous types of parameters to threshold levels that are associated with the one or more parameters. In some embodiments, a threshold value may be selected by a health care provider.

FIG. 4 illustrates a partial cross-sectional side view of system 400 that is configured as an embodiment of an inhaler. System 400 includes a housing 102 having a flow channel 104 disposed therein. Also illustrated are two ports 106 disposed in the housing 102 in fluid communication with the flow channel 104. An active agent reservoir 212 is illustrated as being operably coupled to one of the ports 106. An incentive agent reservoir 216 is illustrated as being operably coupled to the other port 106. The active agent reservoir 212 and the incentive agent reservoir 216 are illustrated as being held within a reservoir support 192. The active agent reservoir 212 and the incentive agent reservoir 216 are both configured as aerosol canisters that include a canister body and a valve stem that extends from the canister body into each of the ports 106. The active agent reservoir 212 includes a controllable valve 258. The incentive agent reservoir 216 also includes a controllable valve 258. Both of the controllable valves 258 are illustrated as being closed as indicated by a closed circle. Flow through the flow channel 104 is illustrated by the two arrows indicating directional flow through the flow channel 104. Flow from right to left toward the mouthpiece 268 is related to an inhalation cycle of a subject using the inhaler. Flow from left to right away from the mouthpiece 268 is related to an exhalation cycle of a subject using the inhaler. A flow sensor 124 is operably coupled to the flow channel 104 and configured to detect flow through the flow channel 104. An aerosol canister content release mechanism 270 is illustrated with a pushrod actuator 256 operably coupled with each of the active agent reservoir 212 and the incentive agent reservoir 216. The aerosol canister content release mechanism 270 is operably coupled with a control unit 108. The control unit 108 is configured to direct operation of the aerosol canister content release mechanism 270 to control each of the pushrod actuators 256 to facilitate at least partial release from each of the active agent reservoir 212 and the incentive agent reservoir 216. The control unit 108 is operably coupled with the flow sensor 124. Accordingly, in some embodiments, the control unit 108 may be configured to facilitate at least partial release from one or both of the active agent reservoir 212 and the incentive agent reservoir 216. In some embodiments, the control unit 108 may be configured to facilitate at least partial release from one or both of the active agent reservoir 212 and the incentive agent reservoir 216 during an inhalation cycle. In some embodiments, the control unit 108 may be configured to halt at least partial release from one or both of the active agent reservoir 212 and the incentive agent reservoir 216 during an exhalation cycle. In some embodiments, the control unit 108 may be configured to facilitate at least partial release from an active agent reservoir 212 and then facilitate at least partial release from an incentive agent reservoir 216. In some embodiments, the control unit 108 may be configured to facilitate at least partial release from an incentive agent reservoir 216 and then facilitate at least partial release from an active agent reservoir 212. In some embodiments, the control unit 108 may be configured to facilitate at least partial release from both the incentive agent reservoir 216 and from the active agent reservoir 212 at substantially the same time. In some embodiments, the flow sensor 124 may be configured to detect a quantity of an active agent 214 that is included in the exhalant of a subject using the inhaler. Accordingly, in some embodiments, such information may be transmitted to the control unit 108 that may use the information to calculate a quantity of the active agent 214 that needs to be administered to the subject to reach a predetermined dosage. The control unit 108 may then control operation of the aerosol canister content release mechanism 270 to administer an additional quantity of the active agent 214 to reach the predetermined dosage.

Figure 4A:
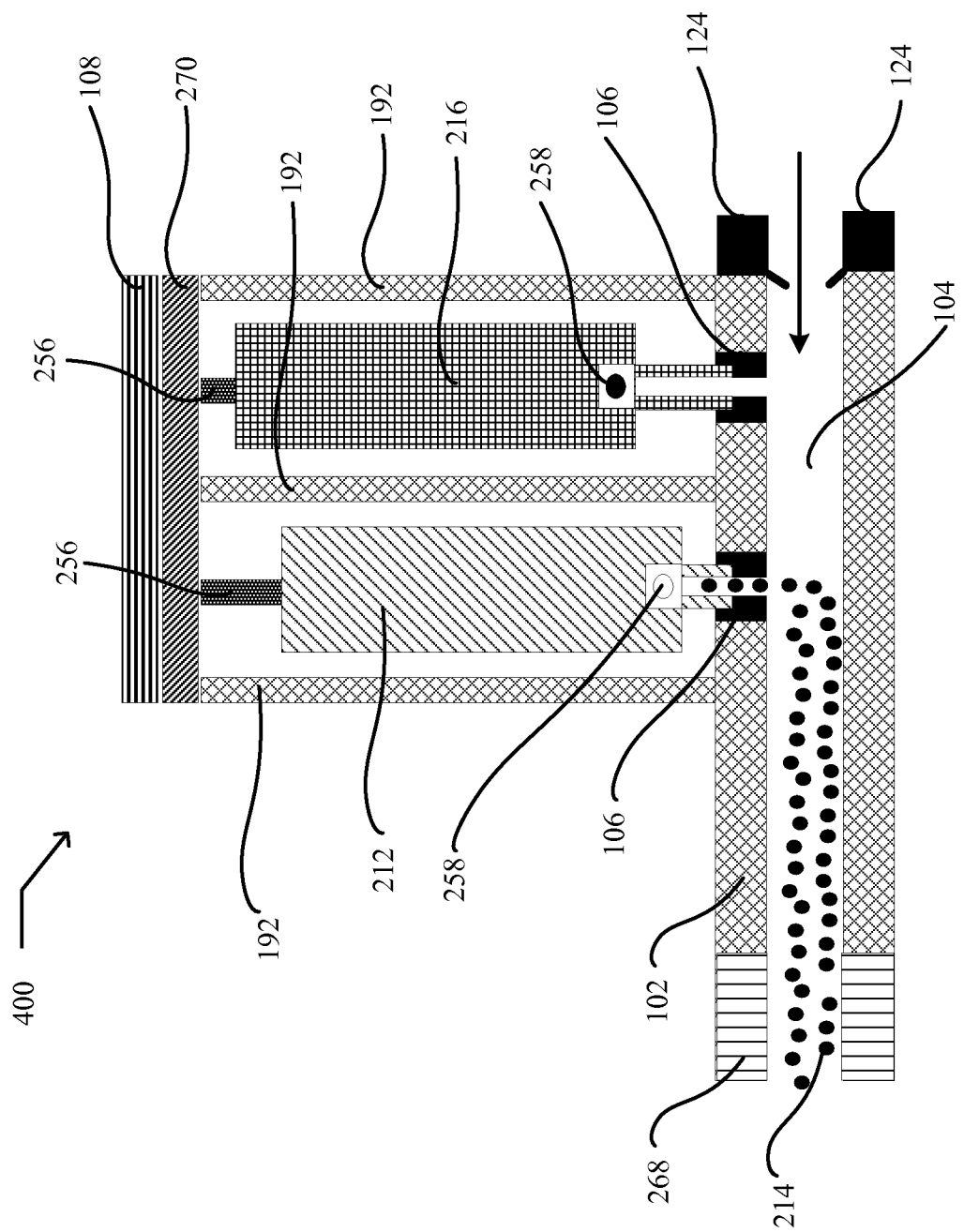
FIG. 4A illustrates a cross-sectional partial side view of an example inhaler 400 in which embodiments may be implemented.

FIG. 4A illustrates a partial cross-sectional side view of system 400 that is configured as an embodiment of an inhaler that is illustrated as being activated to at least partially release an active agent 214 from an active agent reservoir 212. System 400 is shown as an embodiment of an inhaler that includes a housing 102 having a flow channel 104 disposed therein. Also illustrated are two ports 106 disposed in the housing 102 in fluid communication with the flow channel 104. An active agent reservoir 212 is illustrated as being operably coupled to one of the ports 106. An incentive agent reservoir 216 is illustrated as being operably coupled to the other port 106. The active agent reservoir 212 and the incentive agent reservoir 216 are illustrated as being held within a reservoir support 192. The active agent reservoir 212 and the incentive agent reservoir 216 are both configured as aerosol canisters that include a canister body and a valve stem that extends from the canister body into each of the ports 106. The active agent reservoir 212 includes a controllable valve 258. The incentive agent reservoir 216 also includes a controllable valve 258. The controllable valve 258 that is operably coupled to the active agent reservoir 212 is illustrated as being open as indicated by an open circle. The controllable valve 258 that is operably coupled to the incentive agent reservoir 216 is illustrated as being closed as indicated by a closed circle. Flow through the flow channel 104 is illustrated by an arrow indicating right to left flow toward the mouthpiece 268 through the flow channel 104. Flow from right to left toward the mouthpiece 268 is related to an inhalation cycle of a subject using the inhaler. A flow sensor 124 is operably coupled to the flow channel 104 and configured to detect flow through the flow channel 104. An aerosol canister content release mechanism 270 is illustrated with a pushrod actuator 256 operably coupled with each of the active agent reservoir 212 and the incentive agent reservoir 216. The aerosol canister content release mechanism 270 is operably coupled with a control unit 108. The control unit 108 is configured to direct operation of the aerosol canister content release mechanism 270 to control each of the pushrod actuators 256 to facilitate at least partial release from each of the active agent reservoir 212 and the incentive agent reservoir 216. The control unit 108 is operably coupled with the flow sensor 124. The pushrod actuator 256 that is operably associated with the active agent reservoir 212 is illustrated as being in an activated state. In the activated state, the pushrod actuator 256 compresses the canister body of the active agent reservoir 212 that is configured as an aerosol canister toward the valve stem that extends from the canister body to facilitate at least partial release of active agent 214 from the active agent reservoir 212 through the port 106 and into the flow channel 104.

Figure 4B:
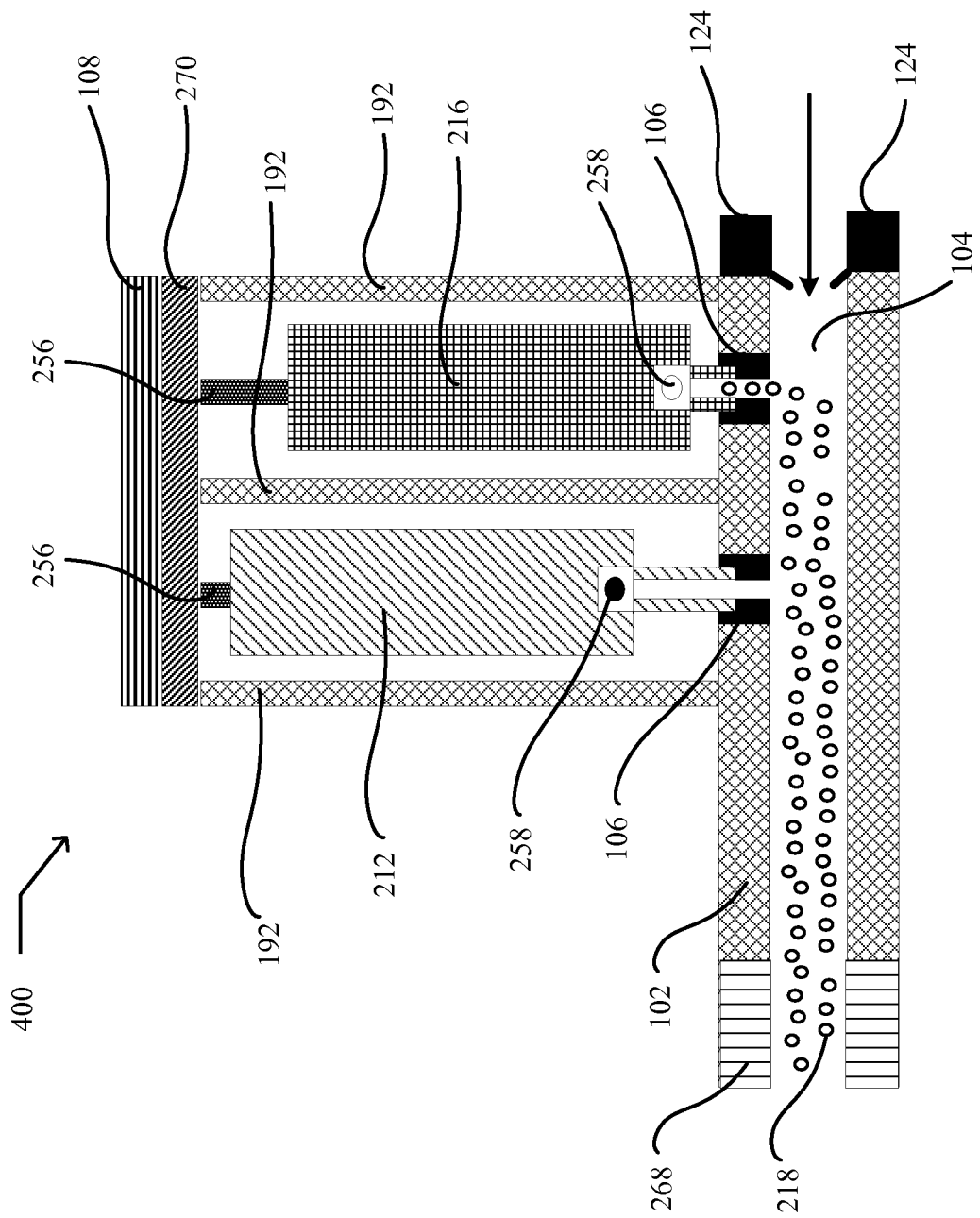
FIG. 4B illustrates a cross-sectional partial side view of an example inhaler 400 in which embodiments may be implemented.

FIG. 4B illustrates a partial cross-sectional side view of system 400 that is configured as an embodiment of an inhaler that is illustrated as being activated to at least partially release incentive agent 218 from an incentive agent reservoir 216. System 400 is illustrated as including a housing 102 having a flow channel 104 disposed therein. Also illustrated are two ports 106 disposed in the housing 102 in fluid communication with the flow channel 104. An active agent reservoir 212 is illustrated as being operably coupled to one of the ports 106. An incentive agent reservoir 216 is illustrated as being operably coupled to the other port 106. The active agent reservoir 212 and the incentive agent reservoir 216 are illustrated as being held within a reservoir support 192. The active agent reservoir 212 and the incentive agent reservoir 216 are both configured as aerosol canisters that include a canister body and a valve stem that extends from the canister body into each of the ports 106. The active agent reservoir 212 includes a controllable valve 258. The incentive agent reservoir 216 also includes a controllable valve 258. The controllable valve 258 that is operably coupled to the incentive agent reservoir 216 is illustrated as being open as indicated by an open circle. The controllable valve 258 that is operably coupled to the active agent reservoir 212 is illustrated as being closed as indicated by a closed circle. Flow through the flow channel 104 is illustrated by an arrow indicating right to left flow toward the mouthpiece 268 through the flow channel 104. Flow from right to left toward the mouthpiece 268 is related to an inhalation cycle of a subject using the inhaler. A flow sensor 124 is operably coupled to the flow channel 104 and configured to detect flow through the flow channel 104. An aerosol canister content release mechanism 270 is illustrated with a pushrod actuator 256 operably coupled with each of the active agent reservoir 212 and the incentive agent reservoir 216. The aerosol canister content release mechanism 270 is operably coupled with a control unit 108. The control unit 108 is configured to direct operation of the aerosol canister content release mechanism 270 to control each of the pushrod actuators 256 to facilitate at least partial release from each of the active agent reservoir 212 and the incentive agent reservoir 216. The control unit 108 is operably coupled with the flow sensor 124. The pushrod actuator 256 that is operably associated with the incentive agent reservoir 216 is illustrated as being in an activated state. In the activated state, the pushrod actuator 256 compresses the canister body of the incentive agent reservoir 216 that is configured as an aerosol canister toward the valve stem that extends from the canister body to facilitate at least partial release of incentive agent 218 from the incentive agent reservoir 216 through the port 106 and into the flow channel 104.

Figure 5:
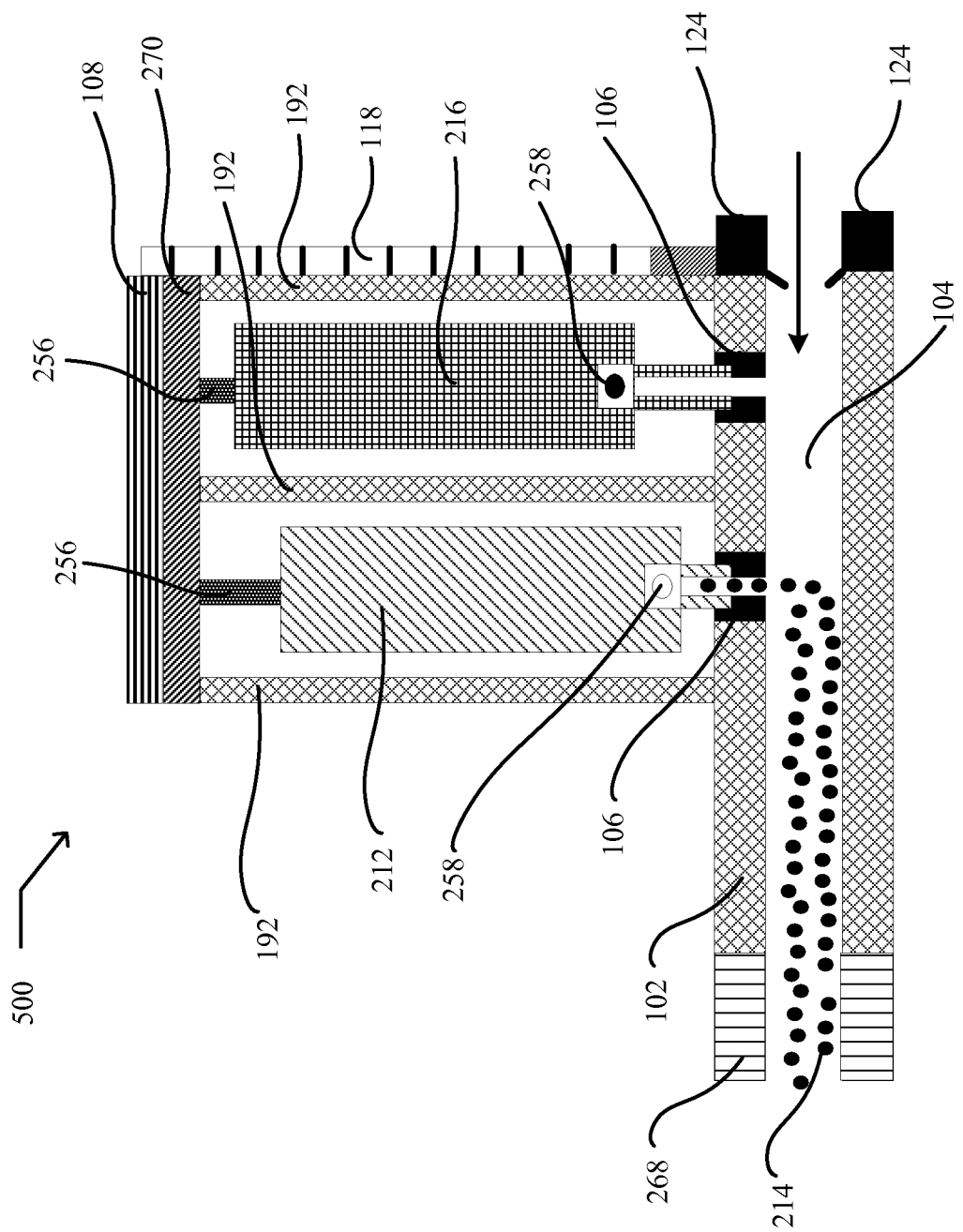
FIG. 5 illustrates a cross-sectional partial side view of an example inhaler 500 in which embodiments may be implemented.

FIG. 5 illustrates a partial cross-sectional side view of system 500 that is configured as an embodiment of an inhaler that is illustrated as being activated to at least partially release active agent 214 from an active agent reservoir 212. System 500 is shown as an embodiment of an inhaler that includes a housing 102 having a flow channel 104 disposed therein. Also illustrated are two ports 106 disposed in the housing 102 in fluid communication with the flow channel 104. An active agent reservoir 212 is illustrated as being operably coupled to one of the ports 106. An incentive agent reservoir 216 is illustrated as being operably coupled to the other port 106. The active agent reservoir 212 and the incentive agent reservoir 216 are illustrated as being held within a reservoir support 192. The active agent reservoir 212 and the incentive agent reservoir 216 are both configured as aerosol canisters that include a canister body and a valve stem that extends from the canister body into each of the ports 106. The active agent reservoir 212 includes a controllable valve 258. The incentive agent reservoir 216 also includes a controllable valve 258. The controllable valve 258 that is operably coupled to the active agent reservoir 212 is illustrated as being open as indicated by an open circle. The controllable valve 258 that is operably coupled to the incentive agent reservoir 216 is illustrated as being closed as indicated by a closed circle. Flow through the flow channel 104 is illustrated by an arrow indicating right to left flow toward the mouthpiece 268 through the flow channel 104. Flow from right to left toward the mouthpiece 268 is related to an inhalation cycle of a subject using the inhaler. A flow sensor 124 is operably coupled to the flow channel 104 and configured to detect flow through the flow channel 104. An aerosol canister content release mechanism 270 is illustrated with a pushrod actuator 256 operably coupled with each of the active agent reservoir 212 and the incentive agent reservoir 216. The aerosol canister content release mechanism 270 is operably coupled with a control unit 108. The control unit 108 is configured to direct operation of the aerosol canister content release mechanism 270 to control each of the pushrod actuators 256 to facilitate at least partial release from each of the active agent reservoir 212 and the incentive agent reservoir 216. The control unit 108 is operably coupled with the flow sensor 124. The pushrod actuator 256 that is operably associated with the formulation reservoir 212 is illustrated as being in an activated state. In the activated state, the pushrod actuator 256 compresses the canister body of the formulation reservoir 212 that is configured as an aerosol canister toward the valve stem that extends from the canister body to facilitate at least partial release of formulation 214 from the formulation reservoir 212 through the port 106 and into the flow channel 104. A dose counter 118 is illustrated. In some embodiments, a dose counter 118 may be operably coupled with a control unit 108. In some embodiments, a dose counter 118 may be operably coupled with a flow sensor 124. The dose counter 118 in this example may be configured to indicate the number of doses administered from the active agent reservoir 212.

Figure 6:
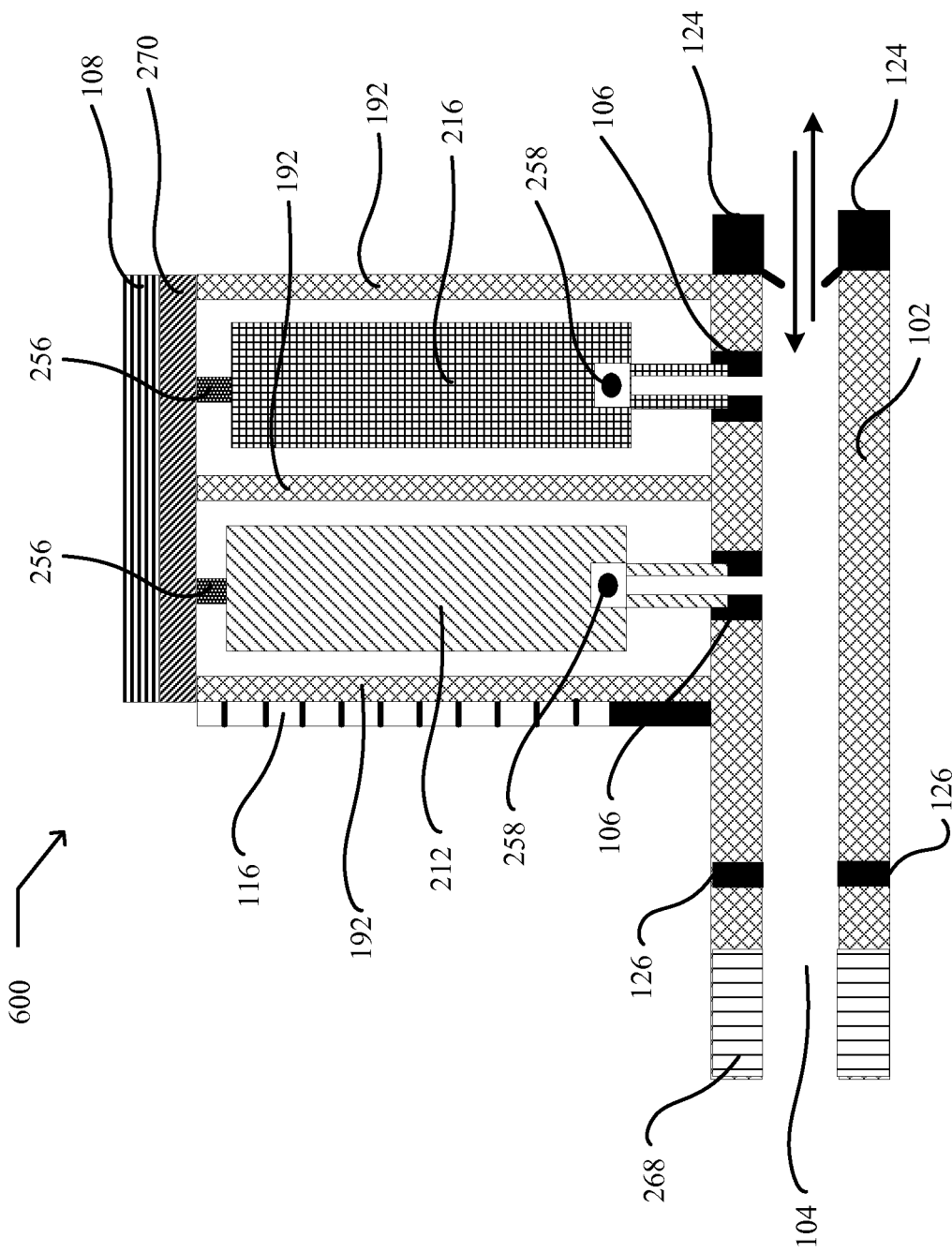
FIG. 6 illustrates a cross-sectional partial side view of an example inhaler 600 in which embodiments may be implemented.

FIG. 6 illustrates a partial cross-sectional side view of system 600. System 600 is shown as an embodiment of an inhaler that includes a housing 102 having a flow channel 104 disposed therein. Also illustrated are two ports 106 disposed in the housing 102 and in fluid communication with the flow channel 104. An active agent reservoir 212 is illustrated as being operably coupled to one of the ports 106. An incentive agent reservoir 216 is illustrated as being operably coupled to the other port 106. The active agent reservoir 212 and the incentive agent reservoir 216 are illustrated as being held within a reservoir support 192. The active agent reservoir 212 and the incentive agent reservoir 216 are both configured as aerosol canisters that include a canister body and a valve stem that extends from the canister body into each of the ports 106. The active agent reservoir 212 includes a controllable valve 258. The incentive agent reservoir 216 also includes a controllable valve 258. Both of the controllable valves 258 are illustrated as being closed as indicated by the closed circles. Flow through the flow channel 104 is illustrated by the two arrows indicating directional flow through the flow channel 104. Flow from right to left toward the mouthpiece 268 is related to an inhalation cycle of a subject using the inhaler. Flow from left to right away from the mouthpiece 268 is related to an exhalation cycle of a subject using the inhaler.

A flow sensor 124 is operably coupled to the flow channel 104 and configured to detect flow through the flow channel 104. An aerosol canister content release mechanism 270 is illustrated with a pushrod actuator 256 operably coupled with each of the active agent reservoir 212 and the incentive agent reservoir 216. The aerosol canister content release mechanism 270 is operably coupled with a control unit 108. The control unit 108 is configured to direct operation of the aerosol canister content release mechanism 270 to control each of the pushrod actuators 256 to facilitate at least partial release from each of the active agent reservoir 212 and the incentive agent reservoir 216. Accordingly, in some embodiments, the control unit 108 may be configured to facilitate at least partial release from one or both of the active agent reservoir 212 and the incentive agent reservoir 216. The control unit 108 is operably coupled with the flow sensor 124. In some embodiments, the control unit 108 may be configured to facilitate at least partial release from one or both of the active agent reservoir 212 and the incentive agent reservoir 216 during an inhalation cycle. In some embodiments, the control unit 108 may be configured to halt at least partial release from one or both of the active agent reservoir 212 and the incentive agent reservoir 216 during an exhalation cycle. In some embodiments, the control unit 108 may be configured to facilitate at least partial release from the active agent reservoir 212 and then facilitate at least partial release from the incentive agent reservoir 216. In some embodiments, the control unit 108 may be configured to facilitate at least partial release from the incentive agent reservoir 216 and then facilitate at least partial release from the active agent reservoir 212. In some embodiments, the control unit 108 may be configured to facilitate at least partial release from the incentive agent reservoir 216 and the active agent reservoir 212 at substantially the same time. In some embodiments, the flow sensor 124 may be configured to detect a quantity of an active agent 214 that is included in the exhalant of a subject using the inhaler. Accordingly, in some embodiments, such information may be transmitted to the control unit 108 that may use the information to calculate a quantity of the active agent 214 that needs to be administered to a subject using the inhaler to reach a predetermined dosage. The control unit 108 may then control the operation of the aerosol canister content release mechanism 270 to administer an additional amount of the active agent 214 to reach the predetermined dosage.

As further shown in FIG. 6, system 600 is illustrated as including a performance indicator 116. In some embodiments, performance indicator 116 may be operably coupled to a flow sensor 124. Accordingly, in some embodiments, a performance indicator 116 may be configured to indicate one or more values related to one or more respiration parameters associated with use of the inhaler by a subject. Examples of such respiration parameters may include, but are not limited to, those related to inhalation performance, exhalation performance, breath hold performance, and the like. The performance indicator 116 in FIG. 6 is illustrated as indicating a low level of respiration performance as compared to the greater level of respiration performance indicated in FIG. 6A. In some embodiments, the flow sensor 124 may be operably coupled with an aerosol canister content release mechanism 270 that is configured to activate a pushrod actuator 256 to facilitate at least partial release of contents from one or both of the active agent reservoir 212 and the incentive agent reservoir 216 when one or more measured respiration parameters meet or exceed one or more threshold values associated with the one or more respiration parameters. An optical sensor 126 is illustrated as being operably coupled with the flow channel 104. In some embodiments, an optical sensor 126 may be configured to assess a quantity of either both of an active agent 214 and an incentive agent 218 that flows through the flow channel 104. Accordingly, in some embodiments, an optical sensor 126 may be operably coupled with a control unit 108 that is configured to assess a quantity of an active agent 214 that is delivered to a subject using the inhaler and then determine an additional amount of active agent 214 that should be delivered to the subject to reach a predetermined dosage level. The control unit 108 may then control the operation of an aerosol canister content release mechanism 270 to facilitate at least partial release from an active agent reservoir 212 to deliver a quantity of an active agent 214 to the subject to reach the predetermined dosage level.

Figure 6A:
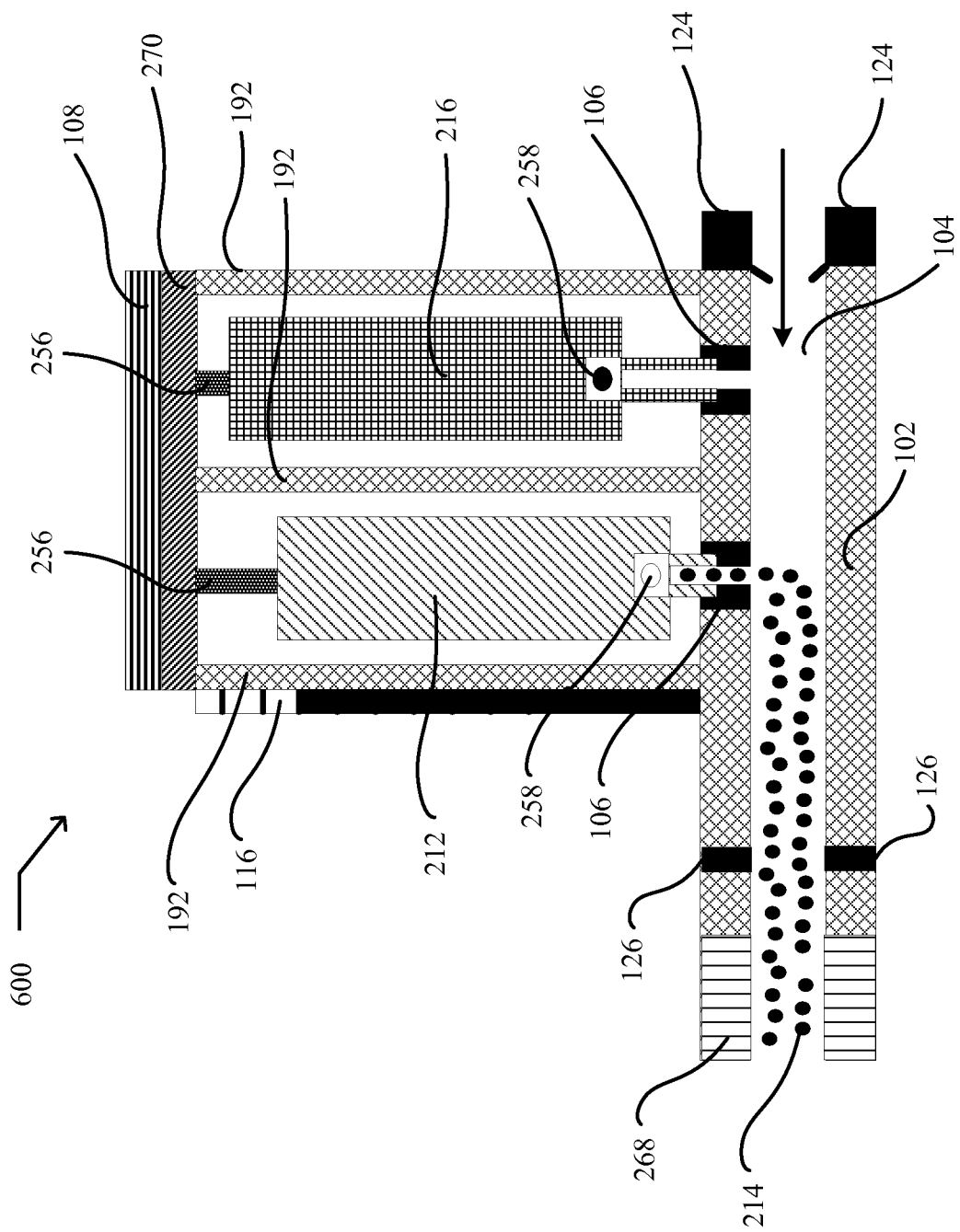
FIG. 6A illustrates a cross-sectional partial side view of an example inhaler 600 in which embodiments may be implemented.

FIG. 6A illustrates a partial cross-sectional side view of system 600. System 600 is shown as an embodiment of an inhaler that is activated to at least partially release an active agent 214 from an active agent reservoir 212. System 600 includes a housing 102 having a flow channel 104 disposed therein. Also illustrated are two ports 106 disposed in the housing 102 and in fluid communication with the flow channel 104. An active agent reservoir 212 is illustrated as being operably coupled to one of the ports 106. An incentive agent reservoir 216 is illustrated as being operably coupled to the other port 106. The active agent reservoir 212 and the incentive agent reservoir 216 are illustrated as being held within a reservoir support 192. The active agent reservoir 212 and the incentive agent reservoir 216 are both configured as aerosol canisters that include a canister body and a valve stem that extends from the canister body into each of the ports 106. The active agent reservoir 212 includes a controllable valve 258. The incentive agent reservoir 216 also includes a controllable valve 258. The controllable valve 258 that is operably coupled to the active agent reservoir 212 is illustrated as being open as indicated by an open circle. The controllable valve 258 that is operably coupled to the incentive agent reservoir 216 is illustrated as being closed as indicated by a closed circle. Flow through the flow channel 104 is illustrated by one arrow indicating directional flow through the flow channel 104 from right to left toward the mouthpiece 268 and indicates an inhalation cycle of a subject using the inhaler. A flow sensor 124 is operably coupled to the flow channel 104 and configured to detect flow through the flow channel 104. An aerosol canister content release mechanism 270 is illustrated with a pushrod actuator 256 operably coupled with each of the active agent reservoir 212 and the incentive agent reservoir 216. The aerosol canister content release mechanism 270 is operably coupled with a control unit 108. The control unit 108 is configured to direct operation of the aerosol canister content release mechanism 270 to control each of the pushrod actuators 256 to facilitate at least partial release from each of the active agent reservoir 212 and the incentive agent reservoir 216. Accordingly, in some embodiments, the control unit 108 may be configured to facilitate at least partial release from one or both of the active agent reservoir 212 and the incentive agent reservoir 216. The control unit 108 is operably coupled with the flow sensor 124. In some embodiments, the control unit 108 may be configured to facilitate at least partial release from one or both of the active agent reservoir 212 and the incentive agent reservoir 216 during an inhalation cycle. In some embodiments, the control unit 108 may be configured to halt at least partial release from one or both of the active agent reservoir 212 and the incentive agent reservoir 216 during an exhalation cycle.

As noted above, in some embodiments, an inhaler may include an operably coupled performance indicator 116. The performance indicator 116 in FIG. 6A is illustrated as indicating a high level of respiration performance as compared to the respiration performance indicated in FIG. 6. In some embodiments a control unit 108 may be configured to control the operation of an aerosol canister content release mechanism 270 that is configured to activate a pushrod actuator 256 to facilitate at least partial release of contents from one or both of the active agent reservoir 212 and the incentive agent reservoir 216 when one or more measured respiration parameters meet or exceed one or more threshold values associated with the one or more respiration parameters. Accordingly, in FIG. 6A the pushrod actuator 256 that is operably coupled to the active agent reservoir 212 is shown as being activated to at least partially release active agent 214 from the active agent reservoir 212 in response to the high level of respiration performance. An optical sensor 126 is illustrated as being operably coupled with the flow channel 104. In some embodiments, an optical sensor 126 may be configured to determine a quantity of either or both of an active agent 214 and an incentive agent 118 that flows through the flow channel 104. Accordingly, in some embodiments, an optical sensor 126 may be operably coupled with a control unit 108 that is configured to determine a quantity of an active agent 214 that is delivered to a subject using the inhaler and then determine an additional amount of active agent 214 that should be delivered to the subject to reach a predetermined dosage level. The control unit 108 may then control the operation of an aerosol canister content release mechanism 270 to facilitate at least partial release from an active agent reservoir 212 to deliver an active agent 214 to the subject to reach the predetermined dosage level.

Figure 6B:
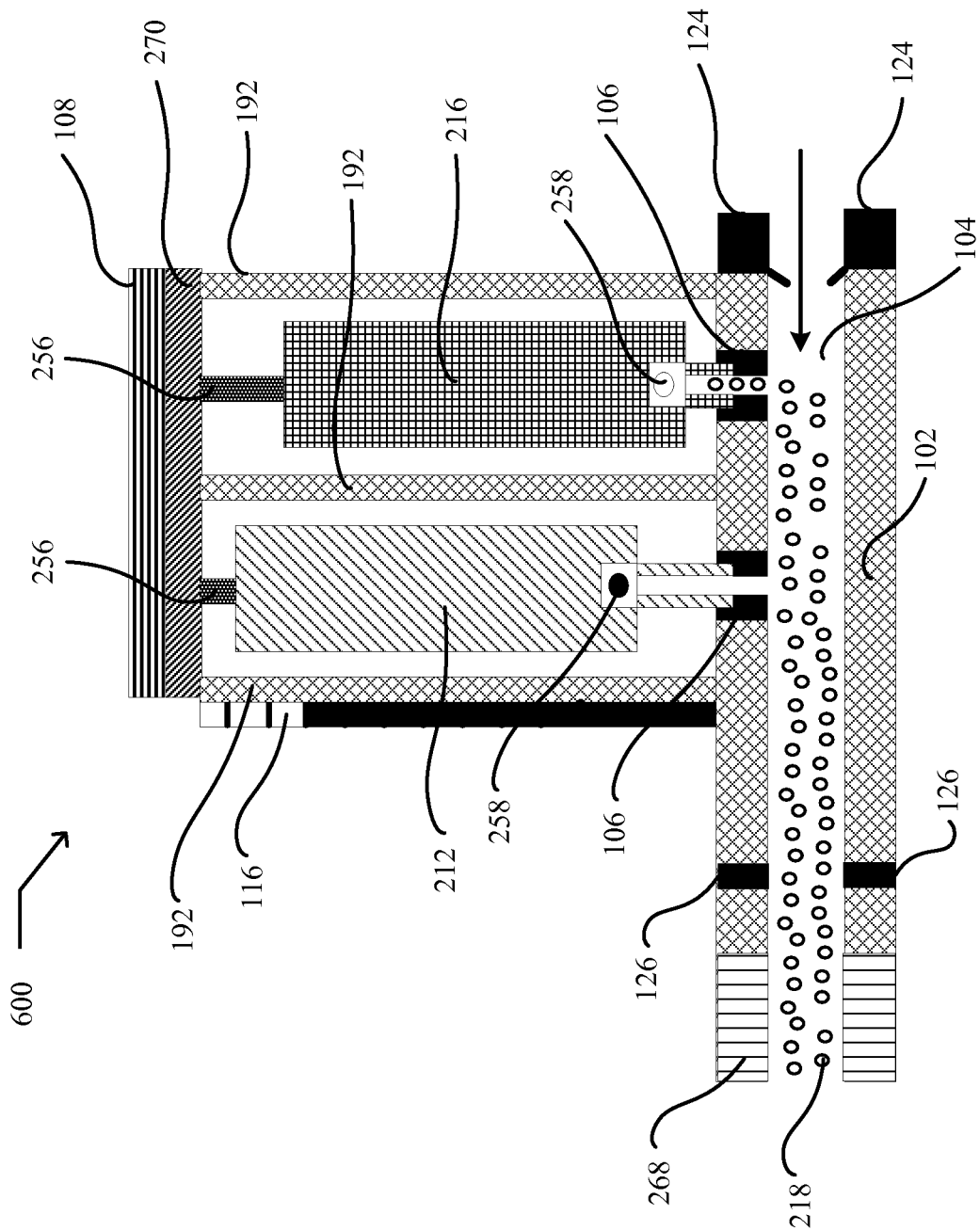
FIG. 6B illustrates a cross-sectional partial side view of an example inhaler 600 in which embodiments may be implemented.

FIG. 6B illustrates a partial cross-sectional side view of system 600. System 600 is shown as an embodiment of an inhaler that is activated to at least partially release an incentive agent 218 from an incentive agent reservoir 216. System 600 includes a housing 102 having a flow channel 104 disposed therein. Also illustrated are two ports 106 disposed in the housing 102 and in fluid communication with the flow channel 104. An active agent reservoir 212 is illustrated as being operably coupled to one of the ports 106. An incentive agent reservoir 216 is illustrated as being operably coupled to the other port 106. The active agent reservoir 212 and the incentive agent reservoir 216 are illustrated as being held within a reservoir support 192. The active agent reservoir 212 and the incentive agent reservoir 216 are both configured as aerosol canisters that include a canister body and a valve stem that extends from the canister body into each of the ports 106. The active agent reservoir 212 includes a controllable valve 258. The incentive agent reservoir 216 also includes a controllable valve 258. The controllable valve 258 that is operably coupled to the active agent reservoir 212 is illustrated as being closed as indicated by a closed circle. The controllable valve 258 that is operably coupled to the incentive agent reservoir 216 is illustrated as being open as indicated by an open circle. Flow through the flow channel 104 is illustrated by one arrow indicating directional flow through the flow channel 104 from right to left toward the mouthpiece 268 and indicates an inhalation cycle of a subject using the inhaler.

A flow sensor 124 is operably coupled to the flow channel 104 and configured to detect flow through the flow channel 104. An aerosol canister content release mechanism 270 is illustrated with a pushrod actuator 256 operably coupled with each of the active agent reservoir 212 and the incentive agent reservoir 216. The aerosol canister content release mechanism 270 is operably coupled with a control unit 108. The control unit 108 is configured to direct operation of the aerosol canister content release mechanism 270 to control each of the pushrod actuators 256 to facilitate at least partial release from each of the active agent reservoir 212 and the incentive agent reservoir 216. Accordingly, in some embodiments, the control unit 108 may be configured to facilitate at least partial release from one or both of the active agent reservoir 212 and the incentive agent reservoir 216. The control unit 108 is operably coupled with the flow sensor 124. Accordingly, in some embodiments, the control unit 108 may be configured to facilitate at least partial release from one or both of the active agent reservoir 212 and the incentive agent reservoir 216. In some embodiments, the control unit 108 may be configured to facilitate at least partial release from one or both of the active agent reservoir 212 and the incentive agent reservoir 216 during an inhalation cycle. In some embodiments, the control unit 108 may be configured to halt at least partial release from one or both of the active agent reservoir 212 and the incentive agent reservoir 216 during an exhalation cycle.

Again, as noted above, in some embodiments, an inhaler may include an operably coupled performance indicator 116. The performance indicator 116 in FIG. 6B is illustrated as indicating a high level of respiration performance as compared to the respiration performance indicated in FIG. 6. In some embodiments a control unit 108 may be configured to control the operation of an aerosol canister content release mechanism 270 to facilitate release of an incentive agent 218 from an incentive agent reservoir 216 when one or more measured parameters related to respiration performance meet or exceed a threshold value. Accordingly, in FIG. 6B the pushrod actuator 256 that is operably coupled to the incentive agent reservoir 216 is shown as being activated to at least partially release an incentive agent 218 from the incentive agent reservoir 216 in response to the high level of respiration performance. An optical sensor 126 is illustrated as being operably coupled with the flow channel 104. In some embodiments, an optical sensor 126 may be configured to determine a quantity of either or both of an active agent 214 and an incentive agent 218 that flows through the flow channel 104. Accordingly, in some embodiments, an optical sensor 126 may be operably coupled with a control unit 108 that is configured to determine a quantity of an incentive agent 218 that is delivered to a subject using the inhaler and then determine an additional amount of an incentive agent 218 that should be delivered to the subject to reach a predetermined administration level. The control unit 108 may then control the operation of an aerosol canister content release mechanism 270 to facilitate at least partial release from one or more incentive agent reservoirs 216 to deliver one or more incentive agents 218 to the subject to reach the predetermined dosage level.

Figure 7:
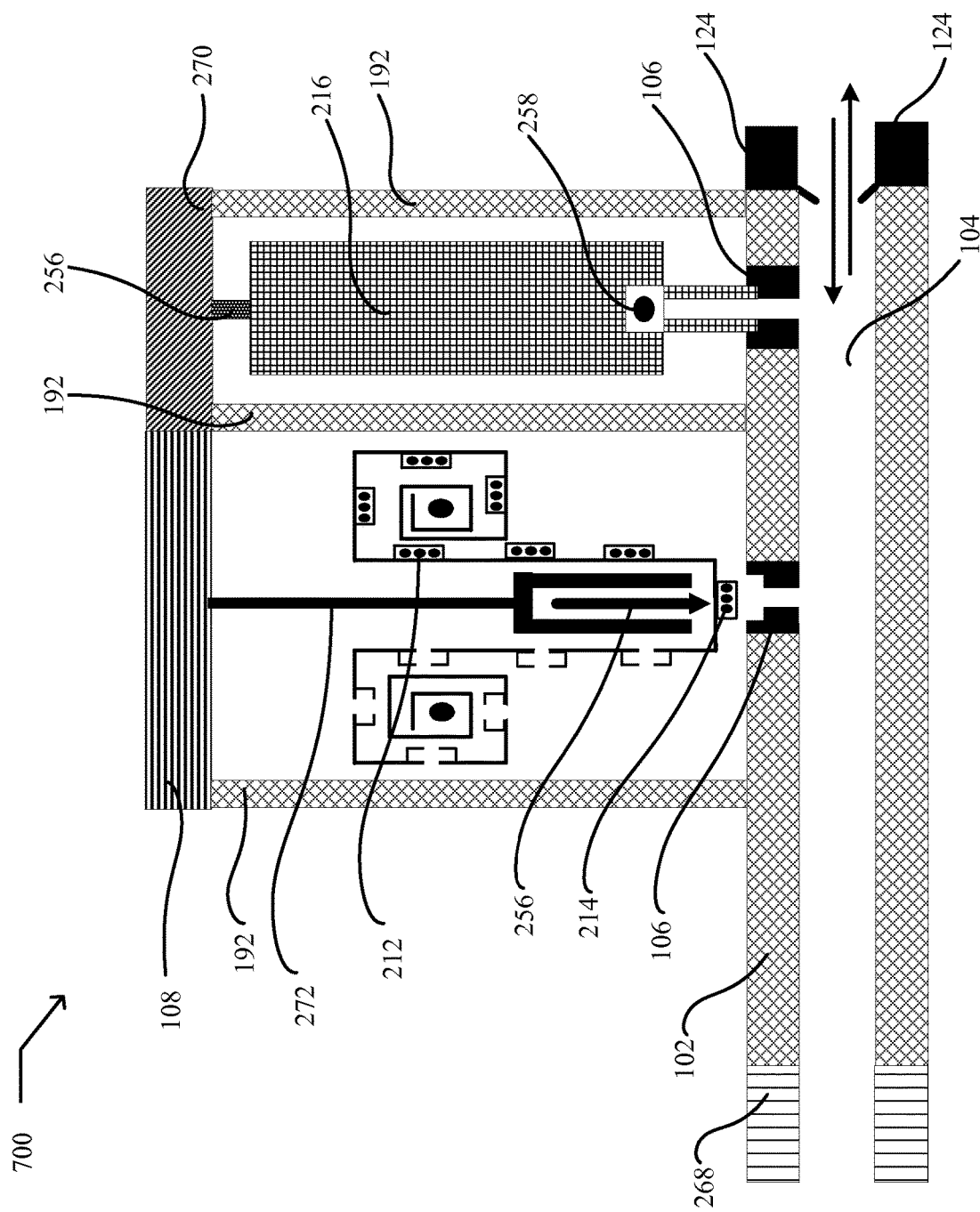
FIG. 7 illustrates a cross-sectional partial side view of an example inhaler 700 in which embodiments may be implemented.

FIG. 7 illustrates a partial cross-sectional side view of system 700 that is configured as an embodiment of an inhaler. System 700 includes a housing 102 having a flow channel 104 disposed therein. Also illustrated are two ports 106 disposed in the housing 102 and in fluid communication with the flow channel 104. An active agent reservoir 212 is illustrated as being aligned with one of the ports 106. An incentive agent reservoir 216 is illustrated as being operably coupled to the other port 106. The active agent reservoir 212 and the incentive agent reservoir 216 are illustrated as being held within a reservoir support 192. The active agent reservoir 212 includes a conveyor with a conveying drive configured to advance a blister strip that includes a plurality of blister packs that are filled with a powdered active agent 214. The conveyor of the active agent reservoir 212 is configured to advance the blister packs past a blister pack puncture mechanism 272. The blister pack puncture mechanism 272 is illustrated as including a pushrod actuator 256 that is configured to puncture a blister pack and propel the powdered active agent 214 contained within the blister pack through port 106 and into the flow channel 104. The incentive agent reservoir 216 is configured as an aerosol canister that includes a canister body and a valve stem that extends from the canister body into a port 106. The incentive agent reservoir 216 includes a controllable valve 258. The controllable valve 258 is illustrated as being closed as indicated by a closed circle. An aerosol canister content release mechanism 270 is operably coupled with the incentive agent reservoir 216 and includes a pushrod actuator 256 that is configured to facilitate at least partial release of incentive agent 218 from the incentive agent reservoir 216. Flow through the flow channel 104 is illustrated by the two arrows indicating directional flow through the flow channel 104. Flow from right to left toward the mouthpiece 268 is related to an inhalation cycle of a subject using the inhaler. Flow from left to right away from the mouthpiece 268 is related to an exhalation cycle of a subject using the inhaler. A flow sensor 124 is operably coupled to the flow channel 104 and configured to detect flow through the flow channel 104.

The aerosol canister content release mechanism 270 is operably coupled with a control unit 108. The blister pack puncture mechanism 272 is operably coupled with a control unit 108. The control unit 108 is configured to direct operation of the aerosol canister content release mechanism 270. The control unit 108 is configured to direct operation of the blister pack puncture mechanism 272. Accordingly, in some embodiments, the control unit 108 may be configured to facilitate at least partial release from one or both of the active agent reservoir 212 and the incentive agent reservoir 216. The control unit 108 is operably coupled with the flow sensor 124. In some embodiments, the control unit 108 may be configured to facilitate at least partial release from one or both of the active agent reservoir 212 and the incentive agent reservoir 216 during an inhalation cycle. In some embodiments, the control unit 108 may be configured to halt at least partial release from one or both of the active agent reservoir 212 and the incentive agent reservoir 216 during an exhalation cycle. In some embodiments, the control unit 108 may be configured to facilitate at least partial release from an active agent reservoir 212 and then facilitate at least partial release from an incentive agent reservoir 216. In some embodiments, the control unit 108 may be configured to facilitate at least partial release from an incentive agent reservoir 216 and then facilitate at least partial release from an active agent reservoir 212. In some embodiments, the control unit 108 may be configured to facilitate at least partial release from both the incentive agent reservoir 216 and from the active agent reservoir 212 at substantially the same time. In some embodiments, the flow sensor 124 may be configured to detect a quantity of active agent 214 that is included in the exhalant of a subject using the inhaler. Accordingly, in some embodiments, such information may be transmitted to the control unit 108 that may use the information to calculate a quantity of the active agent 214 that needs to be administered to the subject to reach a predetermined dosage. The control unit 108 may then control the operation of the blister pack puncture mechanism 272 to administer an additional amount of the active agent 214 to reach the predetermined dosage.

Figure 7A:
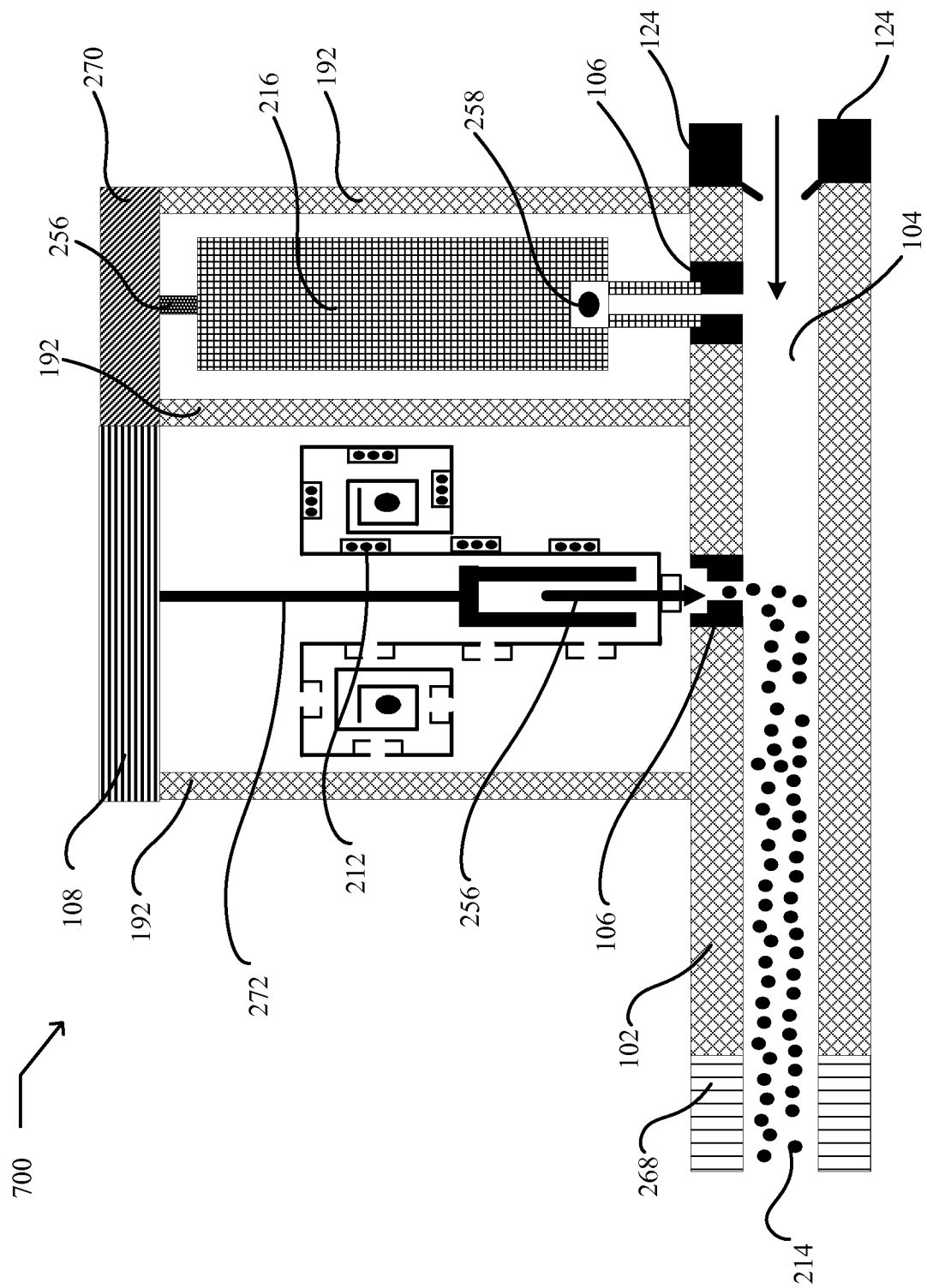
FIG. 7A illustrates a cross-sectional partial side view of an example inhaler 700 in which embodiments may be implemented.

FIG. 7A illustrates a partial cross-sectional side view of system 700 that is configured as an embodiment of an inhaler that is activated to at least partially release active agent 214 from an active agent reservoir 212. System 700 includes a housing 102 having a flow channel 104 disposed therein. Also illustrated are two ports 106 disposed in the housing 102 and in fluid communication with the flow channel 104. An active agent reservoir 212 is illustrated as being aligned with one of the ports 106. An incentive agent reservoir 216 is illustrated as being operably coupled to the other port 106. The active agent reservoir 212 and the incentive agent reservoir 216 are illustrated as being held within a reservoir support 192. The active agent reservoir 212 includes a conveyor with a conveying drive configured to advance a blister strip that includes a plurality of blister packs that are filled with a powdered active agent 214. The conveyor of the active agent reservoir 212 is configured to advance the blister packs past a blister pack puncture mechanism 272. The blister pack puncture mechanism 272 is illustrated as having a pushrod actuator 256 that is configured to puncture a blister pack and propel the powdered active agent 214 contained within the blister pack through port 106 and into the flow channel 104.

In some embodiments, the incentive agent reservoir 216 is configured as an aerosol canister that includes a canister body and a valve stem that extends from the canister body into a port 106. The incentive agent reservoir 216 includes a controllable valve 258. The controllable valve 258 is illustrated as being closed as indicated by a closed circle. An aerosol canister content release mechanism 270 is operably coupled with the incentive agent reservoir 216 and includes a pushrod actuator 256 that is configured to facilitate at least partial release of incentive agent 218 from the incentive agent reservoir 216. Flow through the flow channel 104 is illustrated by an arrow indicating flow from right to left toward the mouthpiece 268. This flow is related to an inhalation cycle of a subject using the inhaler. A flow sensor 124 is operably coupled to the flow channel 104 and configured to detect flow through the flow channel 104. The blister pack puncture mechanism 272 and the aerosol canister content release mechanism 270 are each operably coupled to a control unit 108. Accordingly, in some embodiments, the control unit 108 may direct operation of the blister pack puncture mechanism 272 to facilitate at least partial release of active agent 214 from an active agent reservoir 212. In some embodiments, the control unit 108 may direct operation of the aerosol canister release mechanism 270 to facilitate at least partial release of incentive agent 218 from an incentive agent reservoir 216.

The control unit 108 is operably coupled with the flow sensor 124. In some embodiments, the control unit 108 may be configured to facilitate at least partial release from one or both of the active agent reservoir 212 and the incentive agent reservoir 216 during an inhalation cycle. In some embodiments, the control unit 108 may be configured to halt at least partial release from one or both of the active agent reservoir 212 and the incentive agent reservoir 216 during an exhalation cycle. In some embodiments, the control unit 108 may be configured to facilitate at least partial release from an active agent reservoir 212 and then facilitate at least partial release from an incentive agent reservoir 216. In some embodiments, the control unit 108 may be configured to facilitate at least partial release from an incentive agent reservoir 216 and then facilitate at least partial release from an active agent reservoir 212. In some embodiments, the control unit 108 may be configured to facilitate at least partial release from both the incentive agent reservoir 216 and from the active agent reservoir 212 at substantially the same time. In some embodiments, the flow sensor 124 may be configured to detect a quantity of an active agent 214 that is included in the exhalant of a subject using the inhaler. Accordingly, in some embodiments, such information may be transmitted to the control unit 108 that may use the information to calculate a quantity of the active agent 214 that needs to be administered to the subject to reach a predetermined dosage. The control unit 108 may then control operation of the blister pack puncture mechanism 272 to administer an additional amount of the active agent 214 to reach the predetermined dosage.

Figure 7B:
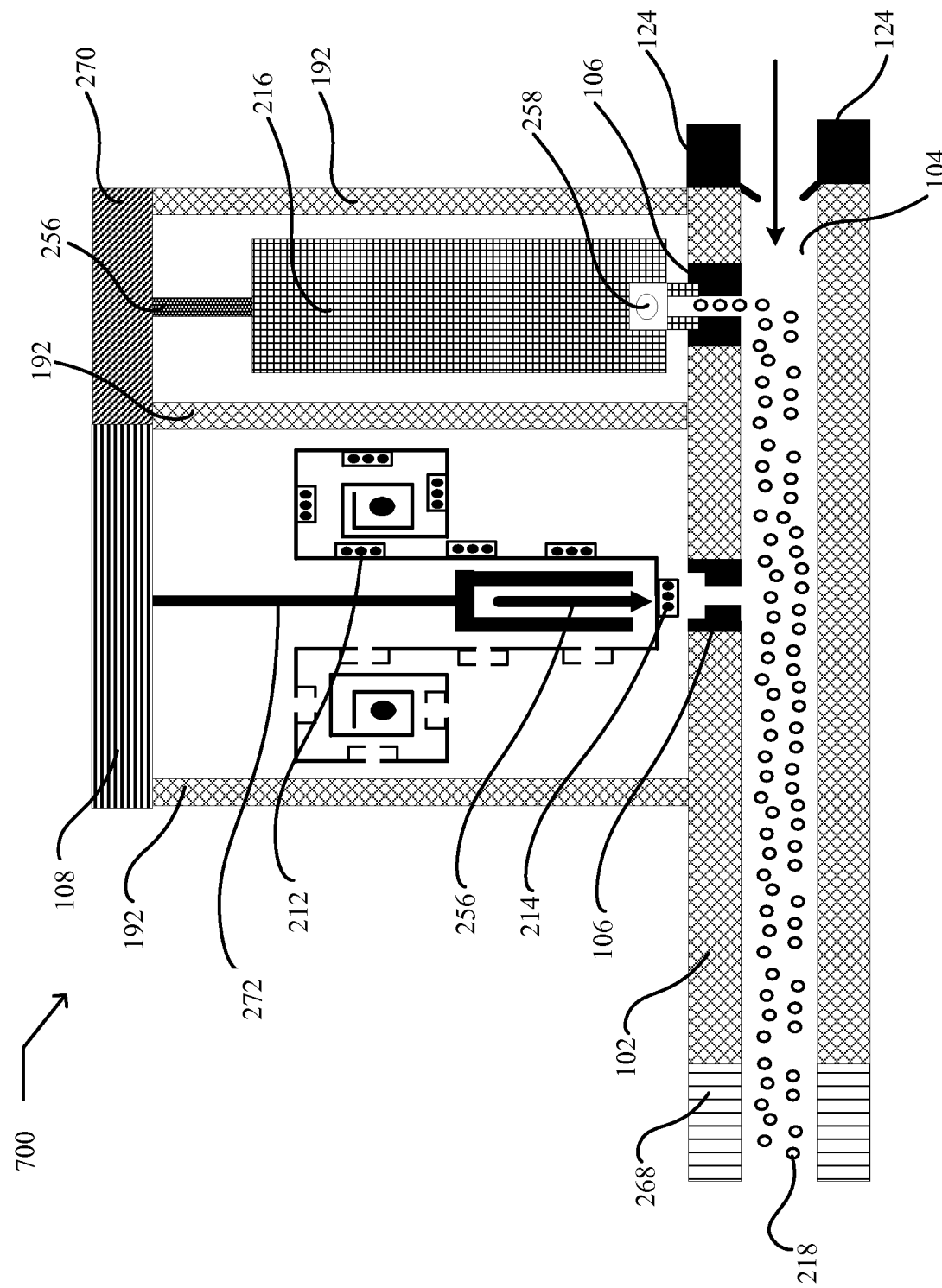
FIG. 7B illustrates a cross-sectional partial side view of an example inhaler 700 in which embodiments may be implemented.

FIG. 7B illustrates a partial cross-sectional side view of system 700 that is configured as an embodiment of an inhaler that is activated to at least partially release an incentive agent 218 from an incentive agent reservoir 216. System 700 includes a housing 102 having a flow channel 104 disposed therein. Also illustrated are two ports 106 disposed in the housing 102 and in fluid communication with the flow channel 104. An active agent reservoir 212 is illustrated as being aligned with one of the ports 106. An incentive agent reservoir 216 is illustrated as being operably coupled to the other port 106. The active agent reservoir 212 and the incentive agent reservoir 216 are illustrated as being held within a reservoir support 192. The active agent reservoir 212 includes a conveyor with a conveying drive configured to advance a blister strip that includes a plurality of blister packs that are filled with a powdered active agent 214. The conveyor of the active agent reservoir 212 is configured to advance the blister packs past a blister pack puncture mechanism 272. The blister pack puncture mechanism 272 is illustrated as including a pushrod actuator 256 that is configured to puncture a blister pack and propel the powdered active agent 214 contained within the blister pack through port 106 and into the flow channel 104.

In some embodiments, the incentive agent reservoir 216 is configured as an aerosol canister that includes a canister body and a valve stem that extends from the canister body into a port 106. The incentive agent reservoir 216 includes a controllable valve 258. An aerosol canister content release mechanism 270 is operably coupled with the incentive agent reservoir 216 and includes a pushrod actuator 256 that is configured to facilitate at least partial release of incentive agent 218 from the incentive agent reservoir 216. The controllable valve 258 is illustrated as being open as indicated by an open circle that facilitates at least partial release of an incentive agent 218 through the port 106 and into the flow channel 104. Flow through the flow channel 104 is illustrated by an arrow indicating flow from right to left toward the mouthpiece 268. This flow is related to an inhalation cycle of a subject using the inhaler. A flow sensor 124 is operably coupled to the flow channel 104 and configured to detect flow through the flow channel 104. The blister pack puncture mechanism 272 and the aerosol canister content release mechanism 270 are each operably coupled to a control unit 108. Accordingly, in some embodiments, the control unit 108 may direct operation of the blister pack puncture mechanism 272 to facilitate at least partial release of active agent 214 from an active agent reservoir 212. In some embodiments, the control unit 108 may direct operation of the aerosol canister release mechanism 270 to facilitate at least partial release of incentive agent 218 from an incentive agent reservoir 216. The control unit 108 is operably coupled with the flow sensor 124. Accordingly, in some embodiments, the control unit 108 may be configured to facilitate at least partial release from one or both of the active agent reservoir 212 and the incentive agent reservoir 216. In some embodiments, the control unit 108 may be configured to facilitate at least partial release from one or both of the active agent reservoir 212 and the incentive agent reservoir 216 during an inhalation cycle. In some embodiments, the control unit 108 may be configured to halt at least partial release from one or both of the active agent reservoir 212 and the incentive agent reservoir 216 during an exhalation cycle. In some embodiments, the control unit 108 may be configured to facilitate at least partial release from an active agent reservoir 212 and then facilitate at least partial release from an incentive agent reservoir 216. In some embodiments, the control unit 108 may be configured to facilitate at least partial release from an incentive agent reservoir 216 and then facilitate at least partial release from an active agent reservoir 212. In some embodiments, the control unit 108 may be configured to facilitate at least partial release from both the incentive agent reservoir 216 and from the active agent reservoir 212 at substantially the same time. In some embodiments, the flow sensor 124 may be configured to detect a quantity of an incentive agent 218 that is included in the exhalant of a subject using the inhaler. Accordingly, in some embodiments, such information may be transmitted to the control unit 108 that may use the information to calculate a quantity of the incentive agent 218 that needs to be administered to the subject to reach a predetermined dosage. The control unit 108 may then control the operation of an aerosol canister release mechanism 270 to administer an additional amount of the incentive agent 218 to reach the predetermined dosage.

Figure 8:
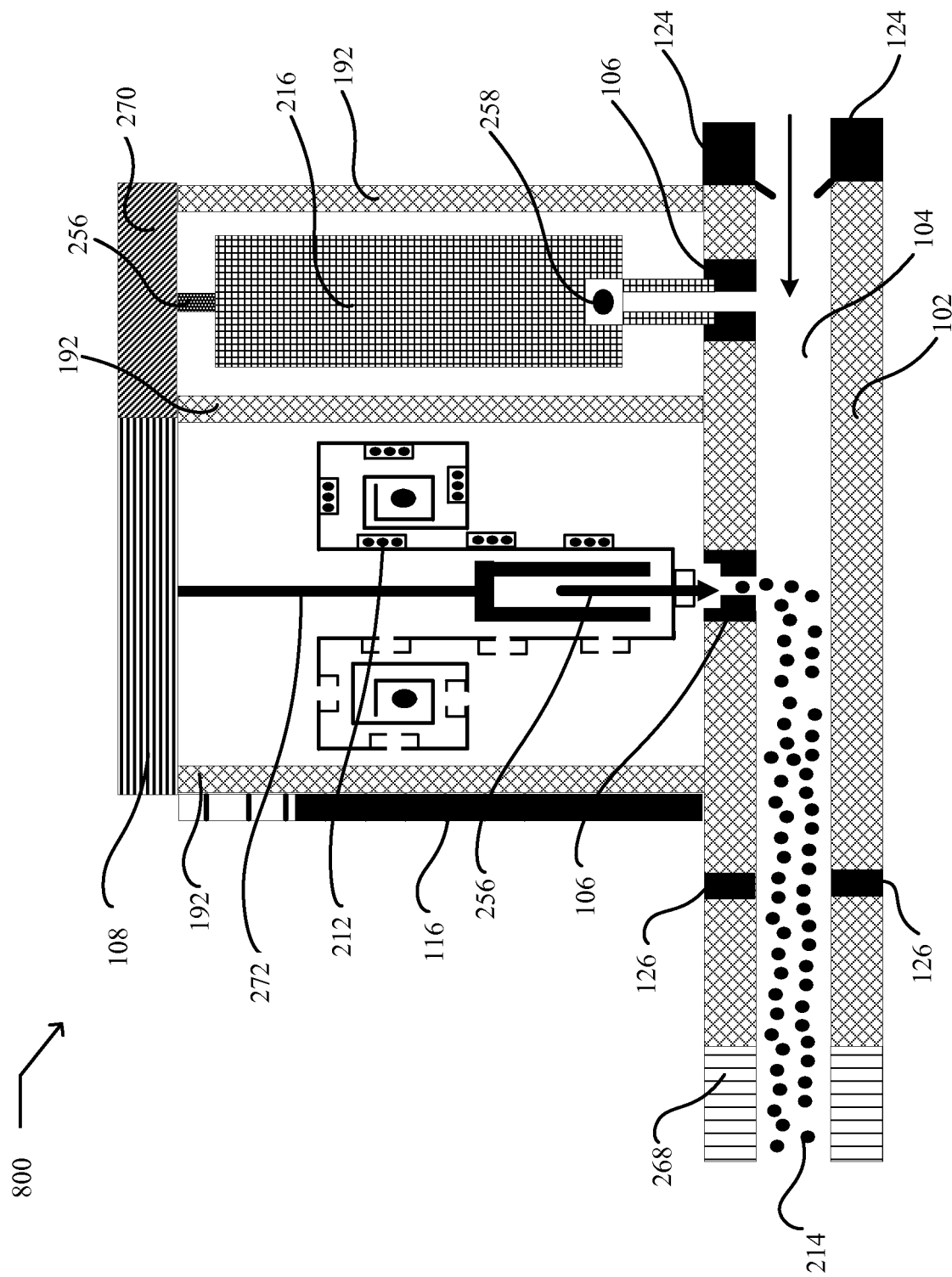
FIG. 8 illustrates a cross-sectional partial side view of an example inhaler 800 in which embodiments may be implemented.

FIG. 8 illustrates a partial cross-sectional side view of system 800 that is configured as an embodiment of an inhaler that is activated to at least partially release active agent 214 from an active agent reservoir 212. System 800 includes a housing 102 having a flow channel 104 disposed therein. Also illustrated are two ports 106 disposed in the housing 102 and in fluid communication with the flow channel 104. An active agent reservoir 212 is illustrated as being aligned with one of the ports 106. An incentive agent reservoir 216 is illustrated as being operably coupled to the other port 106. The active agent reservoir 212 and the incentive agent reservoir 216 are illustrated as being held within a reservoir support 192. The active agent reservoir 212 includes a conveyor with a conveying drive configured to advance a blister strip that includes a plurality of blister packs that are filled with a powdered active agent 214. The conveyor of the active agent reservoir 212 is configured to advance the blister packs past a blister pack puncture mechanism 272. The blister pack puncture mechanism 272 is illustrated as having an activated pushrod actuator 256 that punctured a blister pack and propelled the powdered active agent 214 contained within the blister pack through port 106 and into the flow channel 104. The incentive agent reservoir 216 is configured as an aerosol canister that includes a canister body and a valve stem that extends from the canister body into a port 106. The incentive agent reservoir 216 includes a controllable valve 258. The controllable valve 258 is illustrated as being closed as indicated by a closed circle. An aerosol canister content release mechanism 270 is operably coupled with the incentive agent reservoir 216 and includes a pushrod actuator 256 that is configured to facilitate at least partial release of incentive agent 218 from the incentive agent reservoir 216. Flow through the flow channel 104 is illustrated by an arrow indicating flow from right to left toward the mouthpiece 268. This flow is related to an inhalation cycle of a subject using the inhaler. A flow sensor 124 is operably coupled to the flow channel 104 and configured to detect flow through the flow channel 104. The blister pack puncture mechanism 272 and the aerosol canister content release mechanism 270 are each operably coupled to a control unit 108. Accordingly, in some embodiments, the control unit 108 may direct operation of the blister pack puncture mechanism 272 to facilitate at least partial release of active agent 214 from an active agent reservoir 212. In some embodiments, the control unit 108 may direct operation of the aerosol canister release mechanism 270 to facilitate at least partial release of incentive agent 218 from an incentive agent reservoir 216. The control unit 108 is operably coupled with the flow sensor 124. In some embodiments, the control unit 108 may be configured to facilitate at least partial release from one or both of the active agent reservoir 212 and the incentive agent reservoir 216 during an inhalation cycle. In some embodiments, the control unit 108 may be configured to halt at least partial release from one or both of the active agent reservoir 212 and the incentive agent reservoir 216 during an exhalation cycle. In some embodiments, the control unit 108 may be configured to facilitate at least partial release from an active agent reservoir 212 and then facilitate at least partial release from an incentive agent reservoir 216. In some embodiments, the control unit 108 may be configured to facilitate at least partial release from an incentive agent reservoir 216 and then facilitate at least partial release from an active agent reservoir 212. In some embodiments, the control unit 108 may be configured to facilitate at least partial release from both the incentive agent reservoir 216 and from the active agent reservoir 212 at substantially the same time. In some embodiments, the flow sensor 124 may be configured to detect a quantity of an active agent 214 that is included in the exhalant of a subject using the inhaler. Accordingly, in some embodiments, such information may be transmitted to the control unit 108 that may use the information to calculate a quantity of the active agent 214 that needs to be administered to the subject to reach a predetermined dosage. The control unit 108 may then control the operation of the blister pack puncture mechanism 272 to administer an additional amount of the active agent 214 to reach the predetermined dosage.

In some embodiments, an inhaler may include an operably coupled performance indicator 116. The performance indicator 116 in FIG. 8 is illustrated as indicating a high level of respiration performance. In some embodiments a control unit 108 may be configured to control the operation of a blister pack puncture mechanism 272 to facilitate release of an active agent 214 from an active agent reservoir 212 when one or more assessed parameters related to respiration performance meet or exceed a threshold value. Accordingly, in FIG. 8 the blister pack puncture mechanism 272 is shown as being activated to puncture a blister pack and propel a powdered active agent 214 through a port 106 and into a flow channel 104 in response to the high level of respiration performance. An optical sensor 126 is illustrated as being operably coupled with the flow channel 104. In some embodiments, an optical sensor 126 may be configured to determine a quantity of either or both of an active agent 214 and an incentive agent 218 that flows through the flow channel 104. Accordingly, in some embodiments, an optical sensor 126 may be operably coupled with a control unit 108 that is configured to determine a quantity of an active agent 214 that is delivered to a subject using the inhaler and then determine an additional amount of active agent 214 that should be delivered to the subject to reach a predetermined administration level. The control unit 108 may then control the blister pack puncture mechanism 272 to facilitate at least partial release from one or more active agent reservoirs 212 to deliver active agent 214 to the subject to reach the predetermined dosage level.

Figure 8A:
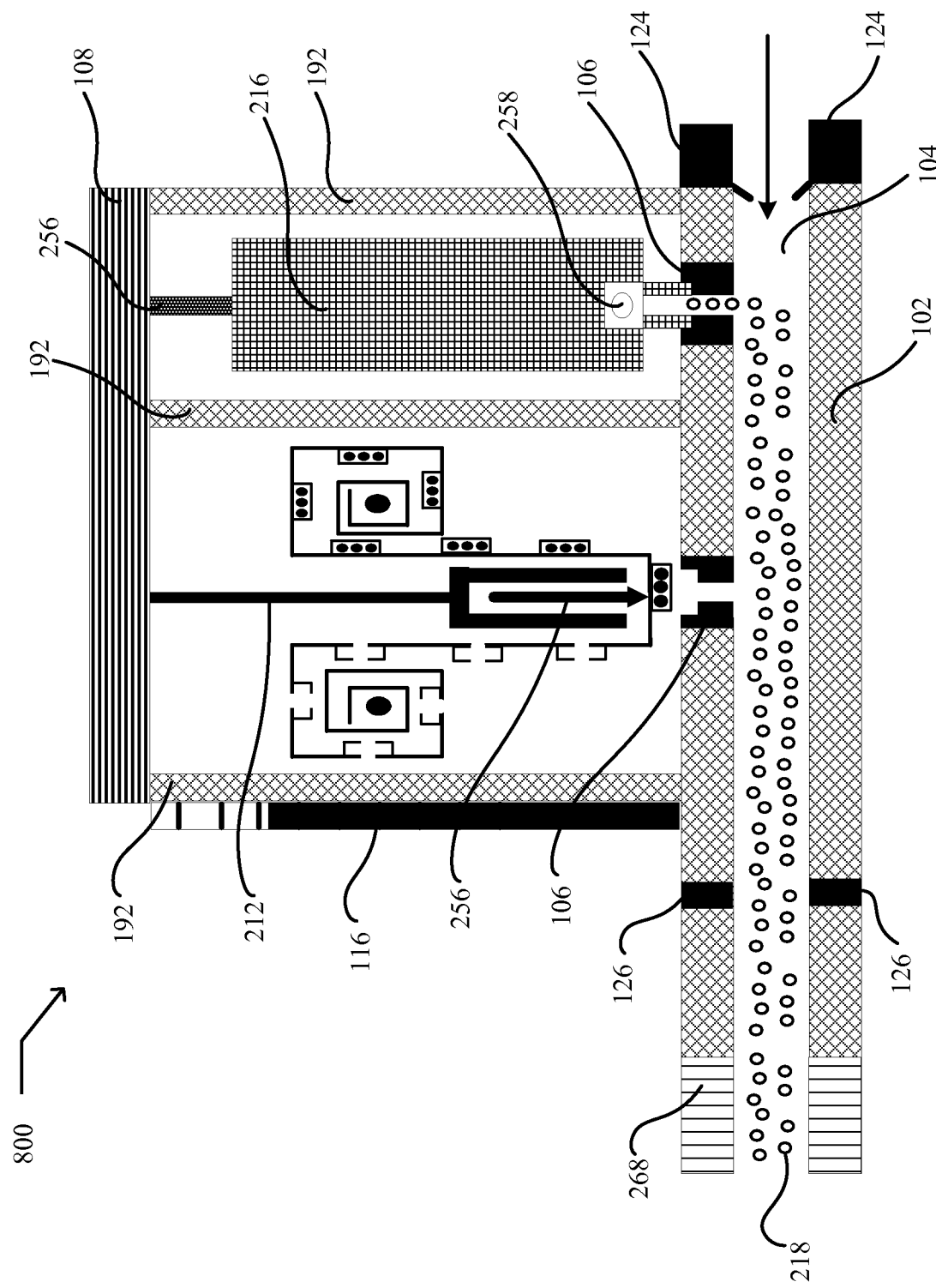
FIG. 8A illustrates a cross-sectional partial side view of an example inhaler 800 in which embodiments may be implemented.

FIG. 8A illustrates a partial cross-sectional side view of system 800 that is configured as an embodiment of an inhaler that is activated to at least partially release an incentive agent 218 from an incentive agent reservoir 216. System 800 includes a housing 102 having a flow channel 104 disposed therein. Also illustrated are two ports 106 disposed in the housing 102 and in fluid communication with the flow channel 104. An active agent reservoir 212 is illustrated as being aligned with one of the ports 106. An incentive agent reservoir 216 is illustrated as being operably coupled to the other port 106. The active agent reservoir 212 and the incentive agent reservoir 216 are illustrated as being held within a reservoir support 192. The active agent reservoir 212 includes a conveyor with a conveying drive configured to advance a blister strip that includes a plurality of blister packs that are filled with a powdered active agent 214. The conveyor of the active agent reservoir 212 is configured to advance the blister packs past a blister pack puncture mechanism 272. The blister pack puncture mechanism 272 is illustrated as having a pushrod actuator 256. The incentive agent reservoir 216 is configured as an aerosol canister that includes a canister body and a valve stem that extends from the canister body into a port 106. The incentive agent reservoir 216 includes a controllable valve 258. The controllable valve 258 is illustrated as being open as indicated by an open circle facilitating release of an incentive agent 218 through a port 106 and into the flow channel 104. Flow through the flow channel 104 is illustrated by an arrow indicating flow from right to left toward the mouthpiece 268. This flow is related to an inhalation cycle of a subject using the inhaler. A flow sensor 124 is operably coupled to the flow channel 104 and configured to detect flow through the flow channel 104. An aerosol canister content release mechanism 270 is illustrated as being operably coupled with the incentive agent reservoir 216. The blister pack puncture mechanism 272 and the aerosol canister content release mechanism 270 are each operably coupled to a control unit 108.

Accordingly, in some embodiments, the control unit 108 may direct operation of the blister pack puncture mechanism 272 to facilitate at least partial release of active agent 214 from an active agent reservoir 212. In some embodiments, the control unit 108 may direct operation of the aerosol canister release mechanism 270 to facilitate at least partial release of incentive agent 218 from an incentive agent reservoir 216. The control unit 108 is operably coupled with the flow sensor 124. In some embodiments, the control unit 108 may be configured to facilitate at least partial release from one or both of the active agent reservoir 212 and the incentive agent reservoir 216 during an inhalation cycle. In some embodiments, the control unit 108 may be configured to halt at least partial release from one or both of the active agent reservoir 212 and the incentive agent reservoir 216 during an exhalation cycle. In some embodiments, the control unit 108 may be configured to facilitate at least partial release from an active agent reservoir 212 and then facilitate at least partial release from an incentive agent reservoir 216. In some embodiments, the control unit 108 may be configured to facilitate at least partial release from an incentive agent reservoir 216 and then facilitate at least partial release from an active agent reservoir 212. In some embodiments, the control unit 108 may be configured to facilitate at least partial release from both the incentive agent reservoir 216 and from the active agent reservoir 212 at substantially the same time.

In some embodiments, the flow sensor 124 may be configured to detect a quantity of an active agent 214 that is included in the exhalant of a subject using the inhaler. Accordingly, in some embodiments, such information may be transmitted to the control unit 108 that may use the information to calculate a quantity of the active agent 214 that needs to be administered to the subject to reach a predetermined dosage. The control unit 108 may then control the operation of a blister pack puncture mechanism 272 to administer an additional amount of the active agent 214 to reach the predetermined dosage.

In some embodiments, an inhaler may include an operably coupled performance indicator 116. The performance indicator 116 in FIG. 8A is illustrated as indicating a high level of respiration performance. In some embodiments a control unit 108 may be configured to control the operation of an aerosol canister content release mechanism 270 to facilitate release of an incentive agent 218 from an incentive agent reservoir 216 when one or more measured parameters related to respiration performance meet or exceed a threshold value. Accordingly, in FIG. 8A the pushrod actuator 256 that is operably coupled to the incentive agent reservoir 216 is shown as being activated to compress the canister body of the incentive agent reservoir 216 against the valve stem to facilitate at least partial release of the incentive agent 218 through a port 106 and into a flow channel 104 in response to the high level of respiration performance. An optical sensor 126 is illustrated as being operably coupled with the flow channel 104. In some embodiments, an optical sensor 126 may be configured to determine a quantity of either or both of an active agent 214 and an incentive agent 218 that flows through the flow channel 104. Accordingly, in some embodiments, an optical sensor 126 may be operably coupled with a control unit 108 that is configured to determine a quantity of an incentive agent 218 that is delivered to a subject using the inhaler and then determine an additional amount of an incentive agent 218 that should be delivered to the subject to reach a predetermined administration level. The control unit 108 may then control the operation of an aerosol canister content release mechanism 270 to facilitate at least partial release from one or more incentive agent reservoirs 216 to deliver an incentive agent 218 to the subject to reach the predetermined dosage level.

Figure 9:
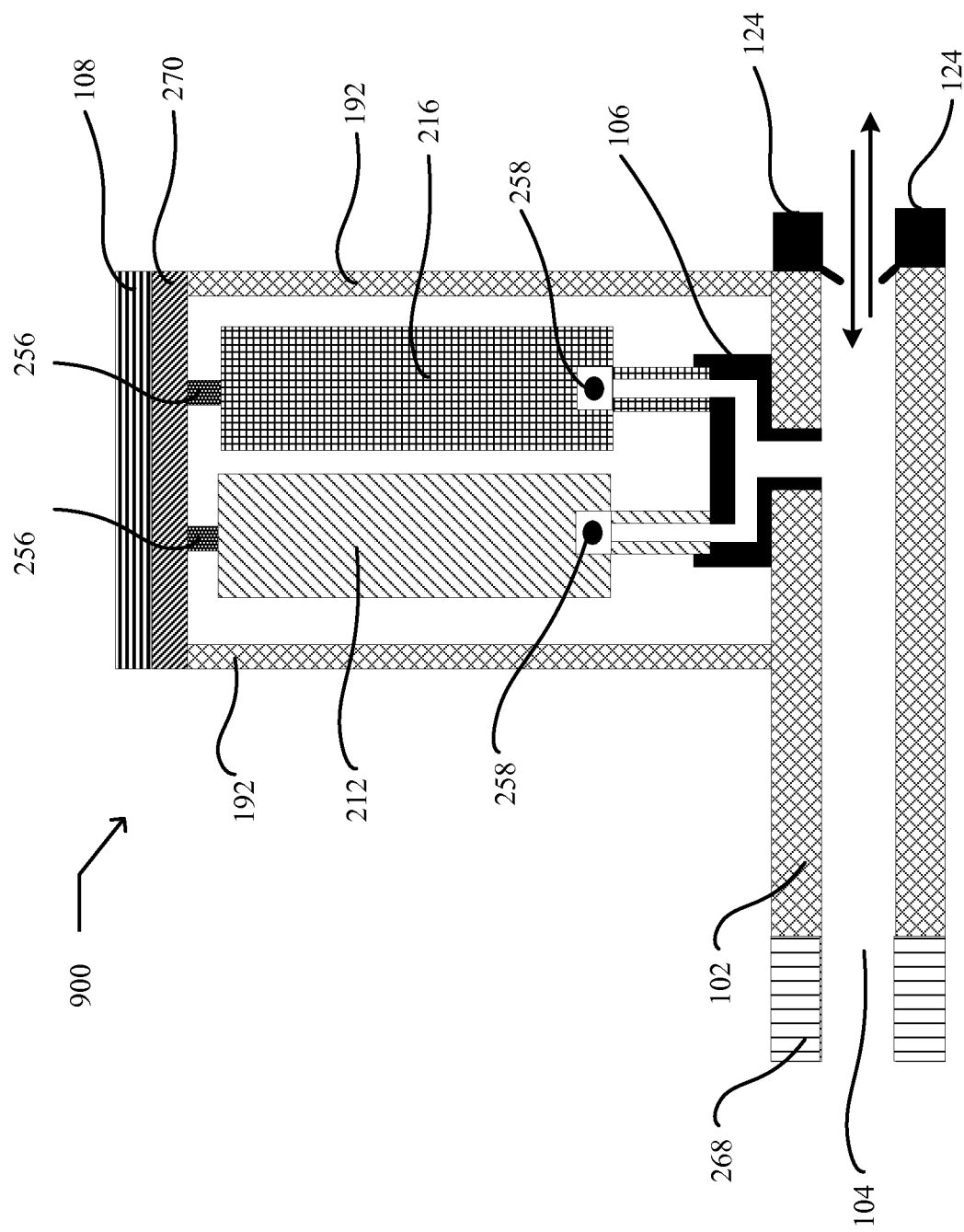
FIG. 9 illustrates a cross-sectional partial side view of an example inhaler 900 in which embodiments may be implemented.

FIG. 9 illustrates a partial cross-sectional side view of system 900 that is configured as an embodiment of an inhaler. System 900 includes a housing 102 having a flow channel 104 disposed therein. Also illustrated is one port 106 disposed in the housing 102 and in fluid communication with the flow channel 104. An active agent reservoir 212 is illustrated as being operably coupled to the port 106. An incentive agent reservoir 216 is illustrated as being operably coupled to the port 106. The active agent reservoir 212 and the incentive agent reservoir 216 are illustrated as being held within a reservoir support 192. The active agent reservoir 212 and the incentive agent reservoir 216 are both configured as aerosol canisters that include a canister body and a valve stem that extends from the canister body into the port 106. The active agent reservoir 212 includes a controllable valve 258. The incentive agent reservoir 216 also includes a controllable valve 258. Both of the controllable valves 258 are illustrated as being closed as indicated by a closed circle. The active agent reservoir 212 and the incentive agent reservoir 216 are both operably coupled with an aerosol canister content release mechanism 270. The aerosol canister content release mechanism 270 includes two pushrod actuators 256. One of the pushrod actuators 256 is operably coupled with the active agent reservoir 212 and the other pushrod actuator 256 is operably coupled to the incentive agent reservoir 216.

Flow through the flow channel 104 is illustrated by the two arrows indicating directional flow through the flow channel 104. Flow from right to left toward the mouthpiece 268 is related to an inhalation cycle of a subject using the inhaler. Flow from left to right away from the mouthpiece 268 is related to an exhalation cycle of a subject using the inhaler. A flow sensor 124 is operably coupled to the flow channel 104 and configured to detect flow through the flow channel 104. The aerosol canister content release mechanism 270 is operably coupled with a control unit 108 that is configured to direct the operation of each of the pushrod actuators 256 to facilitate at least partial release from each of the active agent reservoir 212 and the incentive agent reservoir 216. The control unit 108 is operably coupled with the flow sensor 124. In some embodiments, the control unit 108 may be configured to facilitate at least partial release from one or both of the active agent reservoir 212 and the incentive agent reservoir 216 during an inhalation cycle. In some embodiments, the control unit 108 may be configured to halt at least partial release from one or both of the active agent reservoir 212 and the incentive agent reservoir 216 during an exhalation cycle. In some embodiments, the control unit 108 may be configured to facilitate at least partial release from an active agent reservoir 212 and then facilitate at least partial release from an incentive agent reservoir 216. In some embodiments, the control unit 108 may be configured to facilitate at least partial release from an incentive agent reservoir 216 and then facilitate at least partial release from an active agent reservoir 212. In some embodiments, the control unit 108 may be configured to facilitate at least partial release from both the incentive agent reservoir 216 and from the active agent reservoir 212 at substantially the same time.

Figure 9A:
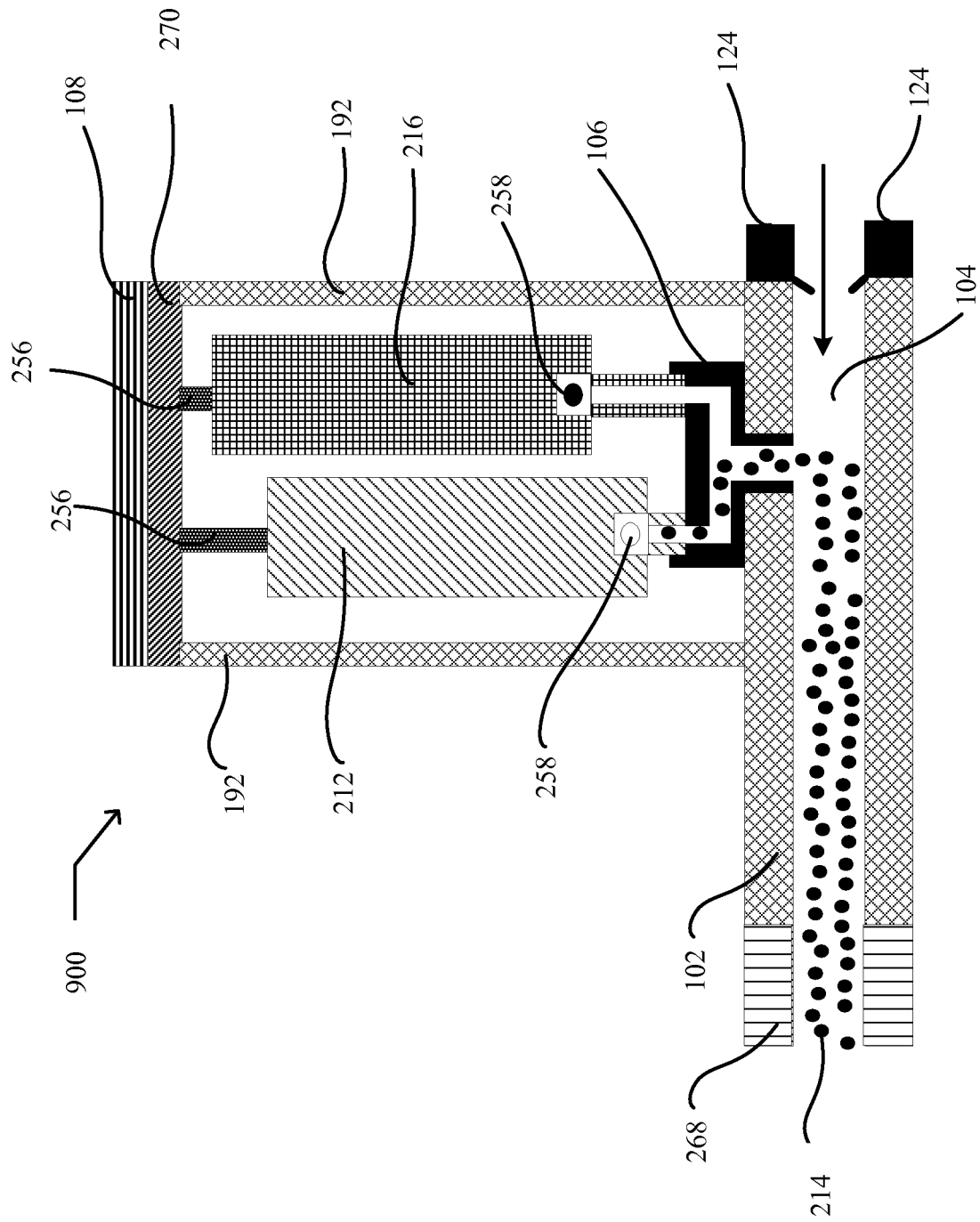
FIG. 9A illustrates a cross-sectional partial side view of an example inhaler 900 in which embodiments may be implemented.

FIG. 9A illustrates a partial cross-sectional side view of system 900 that is configured as an embodiment of an inhaler that is activated to at least partially release an active agent 214 from an active agent reservoir 212. System 900 includes a housing 102 having a flow channel 104 disposed therein. Also illustrated is one port 106 disposed in the housing 102 and in fluid communication with the flow channel 104. An active agent reservoir 212 is illustrated as being operably coupled to the port 106. An incentive agent reservoir 216 is illustrated as being operably coupled to the port 106. The active agent reservoir 212 and the incentive agent reservoir 216 are illustrated as being held within a reservoir support 192. The active agent reservoir 212 and the incentive agent reservoir 216 are both configured as aerosol canisters that include a canister body and a valve stem that extends from the canister body into the port 106. The active agent reservoir 212 includes a controllable valve 258. The incentive agent reservoir 216 also includes a controllable valve 258. The controllable valve 258 that is operably coupled to the active agent reservoir 212 is illustrated as being open to facilitate release of active agent 214 from the active agent reservoir 212 into the flow channel 104 as indicated by an open circle. The controllable valve 258 that is operably coupled to the incentive agent reservoir 216 is illustrated as being closed as indicated by a closed circle.

The active agent reservoir 212 and the incentive agent reservoir 216 are both operably coupled with an aerosol canister content release mechanism 270. The aerosol canister content release mechanism 270 includes two pushrod actuators 256. One of the pushrod actuators 256 is operably coupled with the active agent reservoir 212 and the other pushrod actuator 256 is operably coupled to the incentive agent reservoir 216. Flow through the flow channel 104 is illustrated by the arrow indicating right to left flow through the flow channel 104. Flow from right to left toward the mouthpiece 268 is related to an inhalation cycle of a subject using the inhaler. A flow sensor 124 is operably coupled to the flow channel 104 and configured to detect flow through the flow channel 104. The aerosol canister content release mechanism 270 is operably coupled with a control unit 108 that is configured to direct the operation of each of the pushrod actuators 256 to facilitate at least partial release from each of the active agent reservoir 212 and the incentive agent reservoir 216. The control unit 108 is operably coupled with the flow sensor 124. Accordingly, in some embodiments, the control unit 108 may be configured to facilitate at least partial release from one or both of the active agent reservoir 212 and the incentive agent reservoir 216. In some embodiments, the control unit 108 may be configured to facilitate at least partial release from one or both of the active agent reservoir 212 and the incentive agent reservoir 216 during an inhalation cycle. In some embodiments, the control unit 108 may be configured to halt at least partial release from one or both of the active agent reservoir 212 and the incentive agent reservoir 216 during an exhalation cycle.

Figure 9B:
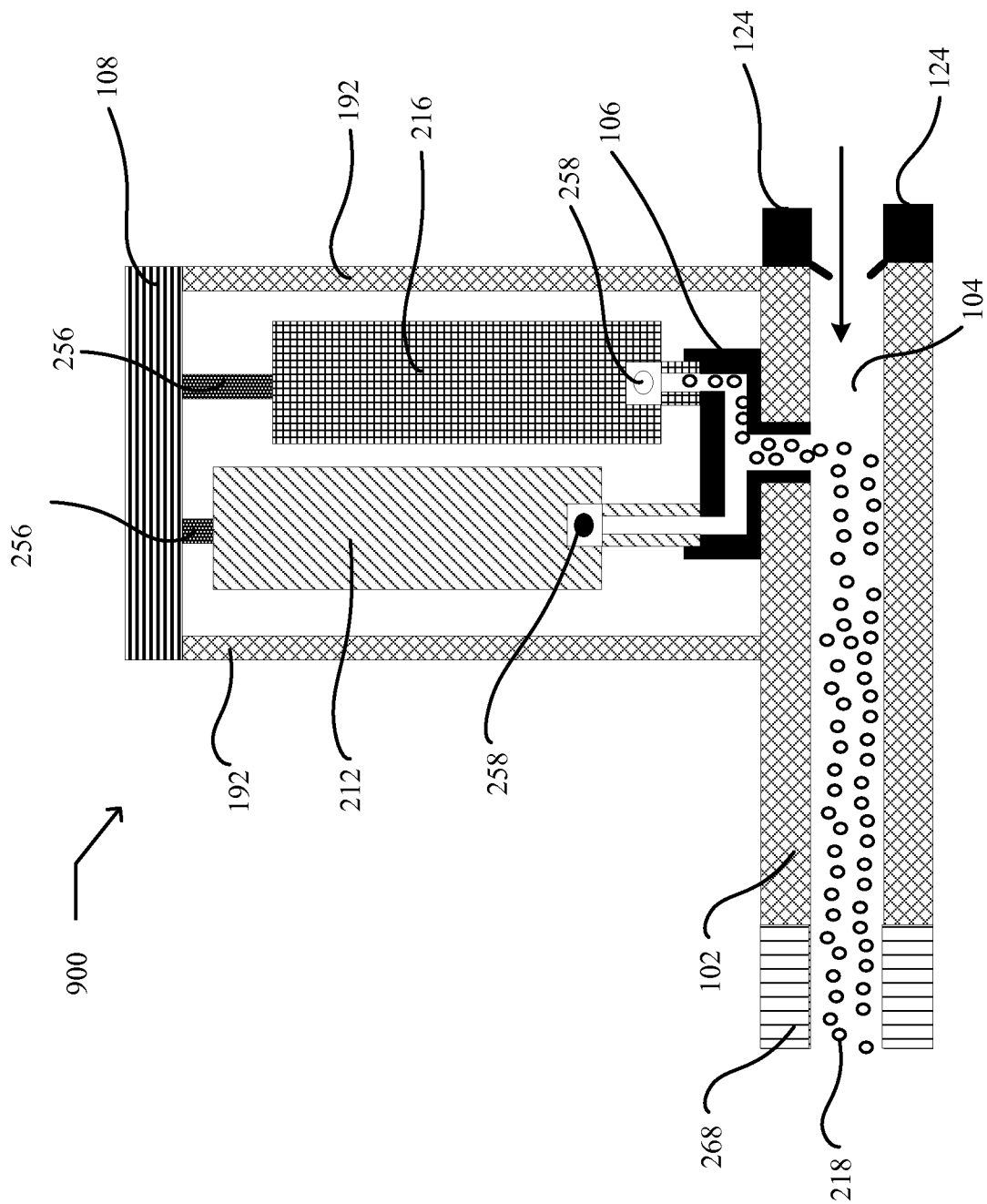
FIG. 9B illustrates a cross-sectional partial side view of an example inhaler 900 in which embodiments may be implemented.

FIG. 9B illustrates a partial cross-sectional side view of system 900 that is configured as an embodiment of an inhaler that is activated to at least partially release an incentive agent 218 from an incentive agent reservoir 216. System 900 includes a housing 102 having a flow channel 104 disposed therein. Also illustrated is one port 106 disposed in the housing 102 and in fluid communication with the flow channel 104. An active agent reservoir 212 is illustrated as being operably coupled to the port 106. An incentive agent reservoir 216 is illustrated as being operably coupled to the port 106. The active agent reservoir 212 and the incentive agent reservoir 216 are illustrated as being held within a reservoir support 192. The active agent reservoir 212 and the incentive agent reservoir 216 are both configured as aerosol canisters that include a canister body and a valve stem that extends from the canister body into the port 106. The active agent reservoir 212 includes a controllable valve 258. The incentive agent reservoir 216 also includes a controllable valve 258. The controllable valve 258 that is operably coupled to the incentive agent reservoir 216 is illustrated as being open to facilitate release of an incentive agent 218 from the incentive agent reservoir 216 into the flow channel 104 as indicated by an open circle. The controllable valve 258 that is operably coupled to the active agent reservoir 212 is illustrated as being closed as indicated by a closed circle. The active agent reservoir 212 and the incentive agent reservoir 216 are both operably coupled with an aerosol canister content release mechanism 270. The aerosol canister content release mechanism 270 includes two pushrod actuators 256. One of the pushrod actuators 256 is operably coupled with the active agent reservoir 212 and the other pushrod actuator 256 is operably coupled to the incentive agent reservoir 216.

Flow through the flow channel 104 is illustrated by the arrow indicating right to left flow through the flow channel 104. Flow from right to left toward the mouthpiece 268 is related to an inhalation cycle of a subject using the inhaler. A flow sensor 124 is operably coupled to the flow channel 104 and configured to detect flow through the flow channel 104. The aerosol canister content release mechanism 270 is operably coupled with a control unit 108 that is configured to direct the operation of each of the pushrod actuators 256 to facilitate at least partial release from each of the active agent reservoir 212 and the incentive agent reservoir 216. The control unit 108 is operably coupled with the flow sensor 124. Accordingly, in some embodiments, the control unit 108 may be configured to facilitate at least partial release from one or both of the active agent reservoir 212 and the incentive agent reservoir 216. In some embodiments, the control unit 108 may be configured to facilitate at least partial release from one or both of the active agent reservoir 212 and the incentive agent reservoir 216 during an inhalation cycle. In some embodiments, the control unit 108 may be configured to halt at least partial release from one or both of the active agent reservoir 212 and the incentive agent reservoir 216 during an exhalation cycle.

Figure 10:
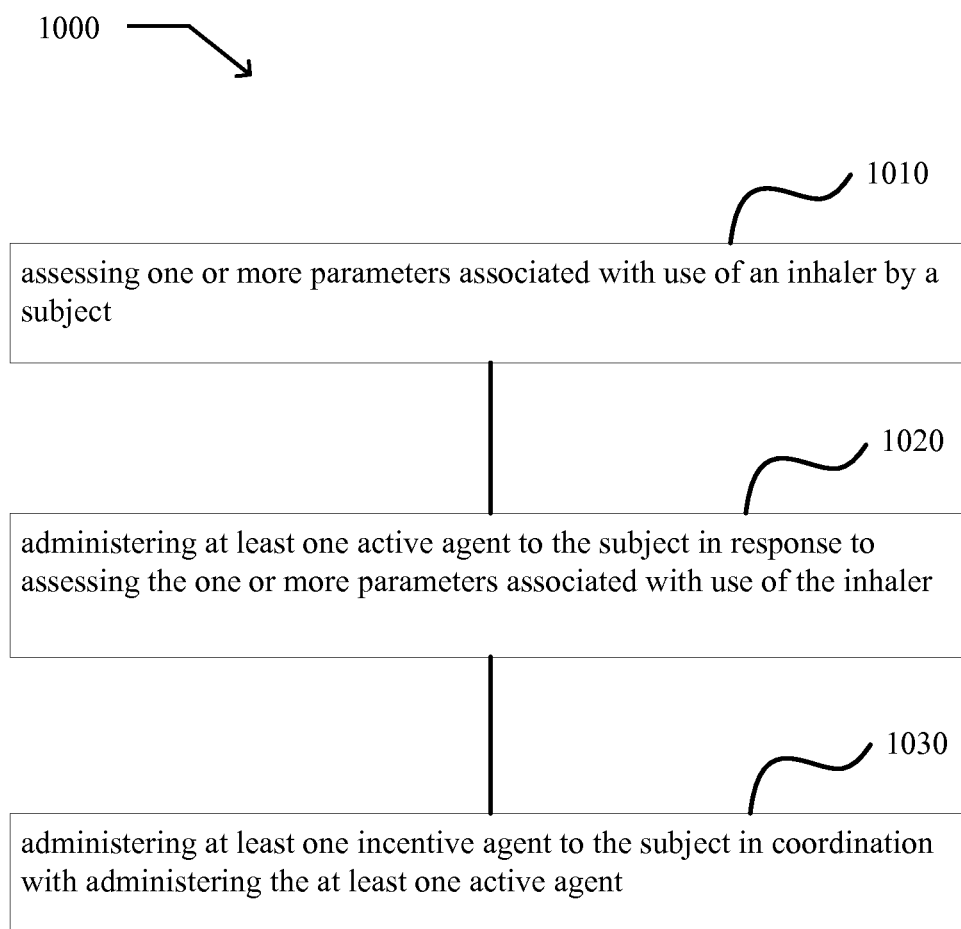
FIG. 10 illustrates an example operational flow 1000 in which embodiments may be implemented.

FIG. 10 illustrates operational flow 1000 that includes operation 1010 that includes assessing one or more parameters associated with use of an inhaler by a subject, operation 1020 that includes administering at least one active agent 214 to the subject in response to assessing the one or more parameters associated with use of the inhaler, and operation 1030 that includes administering at least one incentive agent 218 to the subject in coordination with administering the at least one active agent 214.

In FIG. 10 and in the following description that includes various examples of operations used during performance of the method, discussion and explanation may be provided with respect to any one or combination of the above-described examples, and/or with respect to other examples and contexts. However, it should be understood that the operations may be executed in a number of other environments and contexts, and/or modified versions of the figures. Also, although the various operations are presented in the sequence(s) illustrated, it should be understood that the various operations may be performed in other orders than those which are illustrated, or may be performed concurrently.

Operation 1010 includes assessing one or more parameters associated with use of an inhaler by a subject. In some embodiments, system 100 may be used to assess one or more parameters associated with use of an inhaler by a subject. In some embodiments, components of system 100 may be used to assess one or more parameters associated with use of an inhaler by a subject. For example, in some embodiments, a sensor 114 may be used to assess one or more parameters associated with use of an inhaler by a subject. In some embodiments, a control unit 108 may be used to assess one or more parameters associated with use of an inhaler by a subject. In some embodiments, a performance indicator 116 may be used to assess one or more parameters associated with use of an inhaler by a subject. In some embodiments, a dose counter 118 may be used to assess one or more parameters associated with use of an inhaler by a subject. In some embodiments, a user interface 110 may be used to assess one or more parameters associated with use of an inhaler by a subject. Numerous parameters associated with use of an inhaler may be assessed. Examples of such parameters include, but are not limited to, parameters related to inhalation, exhalation, breath holding, administration of an active agent 214 to a subject, quantity of an active agent 214 administered to a subject, time when an active agent 214 was administered to a subject, administration of an incentive agent 218 to a subject, quantity of an incentive agent 218 administered to a subject, time when an incentive agent 218 was administered to a subject, and the like.

Operation 1020 includes administering at least one active agent 214 to the subject in response to assessing the one or more parameters associated with use of the inhaler. In some embodiments, system 100 may be used to administer at least one active agent 214 to a subject in response to assessing one or more parameters associated with use of an inhaler. In some embodiments, components of system 100 may be used to administer at least one active agent 214 to a subject in response to assessing one or more parameters associated with use of an inhaler. For example, in some embodiments, an actuator 120 may be activated to facilitate at least partial release of an active agent 214 from an active agent reservoir 212. In some embodiments, a blister pack puncture mechanism 272 may be activated to facilitate at least partial release of an active agent 214 from an active agent reservoir 212. In some embodiments, an aerosol canister content release mechanism 270 may be activated to facilitate at least partial release of an active agent 214 from an active agent reservoir 212. In some embodiments, an actuator 120 that is operably coupled with a control unit 108 may be activated to facilitate at least partial release of an active agent 214 from an active agent reservoir 212. In some embodiments, a control unit 108 may receive information that is related to one or more respiration parameters from an operably coupled sensor 114 and then activate one or more operably coupled actuators 120 to facilitate at least partial release of an active agent 214 from an active agent reservoir 212. In some embodiments, a user interface 110 may be used to direct an operably coupled actuator 120 to facilitate at least partial release of an active agent 214 from an active agent reservoir 212. In some embodiments, a performance indicator 116 may be used to direct an operably coupled actuator 120 to facilitate at least partial release of an active agent 214 from an active agent reservoir 212. Accordingly, numerous combinations of components included within system 100 may be used to administer at least one active agent 214 to a subject.

Operation 1030 includes administering at least one incentive agent 218 to the subject in coordination with administering the at least one active agent 214. In some embodiments, system 100 may be used to administer at least one incentive agent 218 to the subject in coordination with administering at least one active agent 214. In some embodiments, components of system 100 may be used to administer at least one incentive agent 218 to the subject in coordination with administering at least one active agent 214. For example, in some embodiments, an actuator 120 may be activated to administer at least one incentive agent 218 to a subject. In some embodiments, a blister pack puncture mechanism 272 may be activated to facilitate at least partial release of an incentive agent 218 from an incentive agent reservoir 216. In some embodiments, an aerosol canister content release mechanism 270 may be activated to facilitate at least partial release of an incentive agent 218 from an incentive agent reservoir 216. In some embodiments, an actuator 120 that is operably coupled with a control unit 108 may be activated to administer at least one incentive agent 218 to a subject. In some embodiments, a control unit 108 may receive information that is related to one or more respiration parameters from an operably coupled sensor 114 and then activate one or more operably coupled actuators 120 to administer at least one incentive agent 218 to a subject. In some embodiments, a user interface 110 may be used to direct an operably coupled actuator 120 to administer at least one incentive agent 218 to a subject. In some embodiments, a performance indicator 116 may be used to direct an operably coupled actuator 120 to administer at least one incentive agent 218 to a subject. Accordingly, numerous combinations of components included within system 100 may be used to administer at least one incentive agent 218 to a subject.

In some embodiments, operation 1010 includes assessing one or more parameters associated with respiration (not shown). In some embodiments, system 100 may be used to assess one or more parameters associated with respiration. For example, in some embodiments, one or more sensors 114 may be configured to assess one or more parameters associated with respiration. In some embodiments, one or more control units 108 may be configured to assess one or more parameters associated with respiration. Numerous parameters associated with respiration by a subject using an inhaler may be assessed. Examples of such parameters include, but are not limited to, time associated with an inhalation cycle, time associated with an exhalation cycle, time associated with a breath hold cycle, volume of flow inhaled through a flow channel 104, volume of flow exhaled through a flow channel 104, velocity of flow through a flow channel 104, and the like.

In some embodiments, operation 1010 includes assessing one or more parameters associated with inhalation (not shown). In some embodiments, system 100 may be used to assess one or more parameters associated with inhalation. For example, in some embodiments, one or more sensors 114 may be configured to assess one or more parameters associated with inhalation. In some embodiments, one or more control units 108 may be configured to assess one or more parameters associated with inhalation. Numerous parameters associated with inhalation by a subject using an inhaler may be assessed. Examples of such parameters include, but are not limited to, time associated with an inhalation cycle, volume of flow inhaled through a flow channel 104, velocity of flow through a flow channel 104 during an inhalation cycle, and the like.

In some embodiments, operation 1010 includes assessing one or more parameters associated with exhalation (not shown). In some embodiments, system 100 may be used to assess one or more parameters associated with exhalation. For example, in some embodiments, one or more sensors 114 may be configured to assess one or more parameters associated with exhalation. In some embodiments, one or more control units 108 may be configured to assess one or more parameters associated with exhalation. Numerous parameters associated with exhalation by a subject using an inhaler may be assessed. Examples of such parameters include, but are not limited to, time associated with an exhalation cycle, volume of flow exhaled through a flow channel 104, velocity of flow through a flow channel 104 during an exhalation cycle, and the like.

In some embodiments, operation 1010 includes assessing one or more parameters associated with breath holding (not shown). In some embodiments, system 100 may be used to assess one or more parameters associated with breath holding. For example, in some embodiments, one or more sensors 114 may be configured to assess one or more parameters associated with breath holding. In some embodiments, one or more control units 108 may be configured to assess one or more parameters associated with breath holding. Numerous parameters associated with breath holding by a subject using an inhaler may be assessed. Examples of such parameters include, but are not limited to, time associated with a breath holding cycle, volume of flow inhaled through a flow channel 104 and held during a breath holding cycle, velocity of flow through a flow channel 104 during an inhalation cycle prior to a breath holding cycle, and the like.

In some embodiments, operation 1010 includes assessing one or more volumes of gas flowing through the inhaler (not shown). In some embodiments, system 100 may be used to assess one or more volumes of gas flowing through the inhaler. For example, in some embodiments, one or more sensors 114 may be configured as a volume sensor 128 to assess one or more volumes of gas flowing through one or more flow channels 104 disposed within an inhaler.

In some embodiments, operation 1010 includes assessing a velocity with which gas flows through the inhaler (not shown). In some embodiments, system 100 may be used to assess a velocity with which gas flows through an inhaler. In some embodiments, one or more sensors 114 may be configured to assess a velocity with which gas flows through one or more flow channels disposed within the inhaler. For example, in some embodiments, a velocimeter 138 may be used to assess a velocity with which gas flows through one or more flow channels 104 disposed within an inhaler.

In some embodiments, operation 1010 includes assessing an amount of negative pressure (e.g. vacuum or suction with respect to a surrounding atmospheric pressure) applied to the inhaler by the subject (not shown). In some embodiments, system 100 may be used to assess an amount of negative pressure applied to an inhaler by a subject using the inhaler. In some embodiments, one or more sensors 114 may be configured to determine an amount of negative pressure applied to an inhaler by a subject using the inhaler. For example, in some embodiments, a vacuum sensor 132 may be used to assess an amount of negative pressure applied to an inhaler by a subject using the inhaler.

In some embodiments, operation 1010 includes assessing a quality of physical contact between the subject and the inhaler (not shown). In some embodiments, system 100 may be used to assess a quality of physical contact between a subject and an inhaler used by the subject. In some embodiments, one or more sensors 114 may be configured to assess a quality of physical contact between a subject and an inhaler used by the subject. For example, in some embodiments, a pressure sensor 130 (e.g., strain sensor and/or a stress sensor) may be configured to measure an amount of force applied to a mouthpiece of an inhaler used by a subject.

In some embodiments, operation 1010 includes assessing a time period associated with any of an inhalation cycle, a breath hold cycle, or an exhalation cycle through the inhaler (not shown). In some embodiments, system 100 may be used to assess a time period associated with any of an inhalation cycle, a breath hold cycle, or an exhalation cycle through one or more flow channels 104 disposed within an inhaler. In some embodiments, one or more sensors 114 may be configured to assess a time period associated with any of an inhalation cycle, a breath hold cycle, or an exhalation cycle through one or more flow channels 104 disposed within an inhaler. For example, in some embodiments, a timer 134 may be used to assess a time period associated with any of an inhalation cycle, a breath hold cycle, or an exhalation cycle through one or more flow channels 104 disposed within an inhaler.

In some embodiments, operation 1010 includes assessing if at least one value associated with a respiration parameter meets or exceeds a threshold value (not shown). In some embodiments, system 100 may be used to assess if at least one value associated with a respiration parameter meets or exceeds a threshold value. In some embodiments, one or more sensors 114 and one or more control units 108 may be configured to assess if at least one value associated with a respiration parameter meets or exceeds a threshold value. For example, in some embodiments, a sensor 114 may be configured as a flow sensor 124 to assess at least one value associated with at least one respiration parameter and then transmit one or more signals that include the value to a control unit 108 that determines if the value meets or exceeds a threshold value. Numerous respiration parameters may be assessed to determine if the respiration parameters meet or exceed an associated threshold value. Examples of such respiration parameters include, but are not limited to, volume of flow through one or more flow channels disposed within an inhaler, velocity of flow through one or more flow channels disposed within an inhaler, and the like.

In some embodiments, operation 1010 includes assessing if at least one value associated with an inhalation parameter meets or exceeds a threshold value (not shown). In some embodiments, system 100 may be used to assess if at least one value associated with an inhalation parameter meets or exceeds a threshold value. In some embodiments, one or more sensors 114 and one or more control units 108 may be configured to assess if at least one value associated with an inhalation parameter meets or exceeds a threshold value. For example, in some embodiments, a sensor 114 may be configured as a flow sensor 124 to assess at least one value associated with at least one inhalation parameter and then transmit one or more signals that include the value to a control unit 108 that assesses if the value meets or exceeds a threshold value. Numerous inhalation parameters may be assessed to determine if the respiration parameter meets or exceeds an associated threshold value. Examples of such inhalation parameters include, but are not limited to, volume of flow through one or more flow channels disposed within an inhaler during an inhalation cycle, velocity of flow through one or more flow channels disposed within an inhaler during an inhalation cycle, and the like.

In some embodiments, operation 1010 includes assessing if at least one value associated with an exhalation parameter meets or exceeds a threshold value (not shown). In some embodiments, system 100 may be used to assess if at least one value associated with an exhalation parameter meets or exceeds a threshold value. In some embodiments, one or more sensors 114 and one or more control units 108 may be configured to determine if at least one value associated with an exhalation parameter meets or exceeds a threshold value. For example, in some embodiments, a sensor 114 may be configured as a flow sensor 124 to assess at least one value associated with at least one exhalation parameter and then transmit one or more signals that include the value to a control unit 108 that assess if the value meets or exceeds a threshold value. Numerous exhalation parameters may be assessed to determine if the exhalation parameter meets or exceeds an associated threshold value. Examples of such exhalation parameters include, but are not limited to, volume of flow through one or more flow channels disposed within an inhaler during an exhalation cycle, velocity of flow through one or more flow channels disposed within an inhaler during an exhalation cycle, and the like.

In some embodiments, operation 1010 includes assessing if at least one value associated with a breath hold parameter meets or exceeds a threshold value (not shown). In some embodiments, system 100 may be used to assess if at least one value associated with a breath hold parameter meets or exceeds a threshold value. In some embodiments, one or more sensors 114 and one or more control units 108 may be configured to assess if at least one value associated with a breath hold parameter meets or exceeds a threshold value. For example, in some embodiments, a timer 134 may be used to measure the length of time associated with a breath hold cycle of a subject using an inhaler and then transmit one or more signals that include the information to a control unit 108 that assesses if the breath hold value meets or exceeds a threshold value. In some embodiments, a sensor 114 may be configured as a flow sensor 124 to assess a volume of flow through one or more flow channels disposed within an inhaler and held during a breath hold cycle of a subject using an inhaler and then transmit one or more signals that include the information to a control unit 108 that assesses if the breath hold value meets or exceeds a threshold value.

In some embodiments, operation 1010 includes assessing one or more values associated with one or more inhalation parameters and estimating a quantity of the at least one active agent 214 that will be effectively delivered in response to the one or more assessed values associated with the one or more inhalation parameters (not shown). In some embodiments, system 100 may be used to assess one or more values associated with one or more inhalation parameters and estimate a quantity of at least one active agent 214 that will be effectively delivered in response to the one or more assessed values associated with the one or more inhalation parameters. Parameters associated with numerous inhalation parameters may be assessed. Examples of such parameters include, but are not limited to, volume of flow through one or more flow channels 104 during an inhalation cycle by a subject using an inhaler, velocity of flow through one or more flow channels 104 during an inhalation cycle by a subject using an inhaler, frequency of inhalation by a subject using an inhaler, time of inhalation by a subject using an inhaler, quantity of active agent 214 flowing through one or more flow channels 104, and the like. In some embodiments, a sensor 114 may be used to determine one or more values associated with an inhalation parameter. The sensor 114 may then transmit one or more signals that include the one or more values to a control unit 108 that uses the one or more values to estimate a quantity of at least one active agent 214 that will be delivered. In some embodiments, a control unit 108 may utilize information that is related to a subject in combination with one or more assessed values associated with an inhalation parameter. For example, in some embodiments, a control unit 108 may use the total volume of flow that was inhaled by a subject with an assessed inhalation value and a quantity of active agent 214 that flowed through a flow channel 104 during an inhalation cycle to estimate a quantity of active agent 214 that was effectively delivered to the subject.

In some embodiments, operation 1010 includes assessing one or more values associated with one or more breath hold parameters and estimating a quantity of the at least one active agent 214 that will be effectively delivered in response to the one or more assessed values associated with the one or more breath hold parameters (not shown). In some embodiments, system 100 may be used to assess one or more values associated with one or more breath hold parameters and estimate a quantity of at least one active agent 214 that will be effectively delivered in response to the one or more assessed values associated with the one or more breath hold parameters. Parameters associated with numerous breath hold parameters may be assessed. Examples of such parameters include, but are not limited to, volume of flow held during a breath hold cycle, time period of a breath hold cycle, quantity of active agent 214 flowing through one or more flow channels 104 during inhalation prior to the breath hold cycle, and the like. In some embodiments, a sensor 114 may be used to assess one or more values associated with a breath hold cycle. The sensor 114 may then transmit one or more signals that include the one or more values to a control unit 108 that uses the one or more values to estimate a quantity of at least one active agent 214 that will be delivered. In some embodiments, a control unit 108 may utilize information that is related to a subject in combination with one or more assessed values associated with a breath hold cycle. For example, in some embodiments, a control unit 108 may use a physical parameter, such as total lung capacity, that is associated with a subject with a determined breath hold value and a quantity of active agent 214 that flowed through a flow channel 104 during an inhalation cycle to estimate a quantity of active agent 214 that was effectively delivered to the subject.

In some embodiments, operation 1010 includes assessing one or more values associated with one or more inhalation parameters and estimating a quantity of the at least one incentive agent 218 that will be effectively delivered in response to the one or more assessed values associated with the one or more inhalation parameters (not shown). In some embodiments, system 100 may be used to assess one or more values associated with one or more inhalation parameters and estimating a quantity of the at least one incentive agent 218 that will be effectively delivered in response to the one or more assessed values associated with the one or more inhalation parameters. Numerous inhalation parameters may be assessed. Examples of such parameters include, but are not limited to, volume of flow through one or more flow channels 104 during an inhalation cycle, velocity of flow through one or more flow channels 104 during an inhalation cycle, quantity of incentive agent 218 flowing through one or more flow channels 104 during an inhalation cycle, and the like. In some embodiments, a sensor 114 may be used to assess one or more values associated with an inhalation parameter. The sensor 114 may then transmit one or more signals that include the one or more values to a control unit 108 that uses the one or more values to estimate a quantity of at least one incentive agent 218 that will be delivered. In some embodiments, a control unit 108 may utilize information that is related to a subject in combination with one or more assessed values associated with an inhalation parameter. For example, in some embodiments, a control unit 108 may use a physical parameter, such as total lung capacity, that is associated with a subject with an assessed value related to an inhalation parameter and a quantity of incentive agent 218 that flowed through a flow channel 104 during an inhalation cycle to estimate a quantity of incentive agent 218 that was effectively delivered to the subject.

In some embodiments, operation 1010 includes assessing one or more values associated with one or more breath hold parameters and estimating a quantity of the at least one incentive agent 218 that will be effectively delivered in response to the one or more assessed values associated with the one or more breath hold parameters (not shown). In some embodiments, system 100 may be used to assess one or more values associated with one or more breath hold parameters and estimate a quantity of the at least one incentive agent 218 that will be effectively delivered in response to the one or more assessed values associated with the one or more breath hold parameters. Numerous breath hold parameters may be assessed. Examples of such parameters include, but are not limited to, volume of flow through one or more flow channels 104 that is held during a breath hold cycle, a time period associated with a breath hold cycle, a quantity of incentive agent 218 flowing through one or more flow channels 104 during an inhalation cycle prior to the breath hold cycle, and the like. In some embodiments, a sensor 114 may be used to assess one or more values associated with a breath hold parameter. The sensor 114 may then transmit one or more signals that include the one or more values to a control unit 108 that uses the one or more values to estimate a quantity of at least one incentive agent 218 that will be delivered. In some embodiments, a control unit 108 may utilize information that is related to a subject in combination with one or more assessed values associated with a breath hold parameter. For example, in some embodiments, a control unit 108 may use a physical parameter, such as total lung capacity, that is associated with a subject with an assessed value related to a breath hold parameter and a quantity of incentive agent 218 that flowed through a flow channel 104 during an inhalation cycle to estimate a quantity of incentive agent 218 that will be effectively delivered to the subject. In some embodiments, a control unit 108 may utilize an absorption rate that is associated with an incentive agent 218 to estimate a quantity of the incentive agent 218 that will be delivered to a subject.

In some embodiments, operation 1020 includes administering the at least one active agent 214 to the subject when at least one value associated with the one or more parameters associated with use of the inhaler meets or exceeds a threshold value (not shown). In some embodiments, system 100 may be used to administer at least one active agent 214 to a subject when at least one value associated with one or more parameters associated with use of an inhaler meets or exceeds a threshold value. For example, in some embodiments, a control unit 108 may receive one or more signals that include one or more assessed values associated with velocity of flow through one or more flow channels 104 disposed within an inhaler during an inhalation cycle by a subject from a sensor 114. The control unit 108 may compare the one or more assessed values to one or more threshold values associated with velocity of flow during an inhalation cycle and activate one or more actuators 120 to facilitate at least partial release of one or more active agents 214 from one or more active agent reservoirs 212 to deliver the one or more active agents 214 to the subject using the inhaler if the one or more assessed values meet or exceed the one or more threshold values.

In some embodiments, operation 1020 includes administering the at least one active agent 214 to the subject in response to assessing at least one value associated with a respiration parameter (not shown). In some embodiments, system 100 may be used to administer at least one active agent 214 to the subject in response to assessing at least one value associated with a respiration parameter. For example, in some embodiments, a control unit 108 may receive one or more signals that include one or more assessed values associated with a volume of flow through one or more flow channels 104 disposed within an inhaler used by a subject from a sensor 114. The control unit 108 may then utilize the assessed value to determine a quantity of active agent 214 to be released from an active agent reservoir 212 based on the assessed volume of flow. In some embodiments, a control unit 108 may receive information associated with a time period associated with an inhalation cycle of a subject using an inhaler. The control unit 108 may then direct an actuator 120 to facilitate at least partial release from an active agent reservoir 212 during an early stage of an inhalation cycle.

In some embodiments, operation 1020 includes administering the at least one active agent 214 to the subject when at least one value associated with a respiration parameter meets or exceeds a threshold value (not shown). In some embodiments, system 100 may be used to administer at least one active agent 214 to a subject when at least one value associated with a respiration parameter meets or exceeds a threshold value. For example, in some embodiments, a control unit 108 may receive one or more signals that include one or more assessed values associated with velocity of flow through one or more flow channels 104 disposed within an inhaler used by a subject during an inhalation cycle from one or more sensors 114. The control unit 108 may compare the one or more assessed values to one or more threshold values associated with the velocity of flow and activate one or more actuators 120 to facilitate at least partial release of one or more active agents 214 from one or more active agent reservoirs 212 to administer the one or more active agents 214 to the subject using the inhaler if the one or more assessed values associated with velocity of flow meet or exceed the one or more threshold values. In some embodiments, a control unit 108 may receive one or more signals that include one or more assessed values associated with a volume of flow through one or more flow channels 104 disposed within an inhaler used by a subject during an exhalation cycle from a sensor 114. The control unit 108 may compare the one or more assessed values to one or more threshold values associated with volume of flow during an exhalation cycle. The control unit 108 may then receive one or more signals that include one or more assessed values associated with velocity of flow through one or more flow channels 104 disposed within the inhaler used by a subject during an inhalation cycle from a sensor 114. The control unit 108 may then compare the one or more assessed values to one or more threshold values associated with velocity of flow during an inhalation cycle. The control unit 108 may then activate one or more actuators 120 to facilitate at least partial release of one or more active agents 214 from one or more active agent reservoirs 212 to administer the one or more formulations 214 to the subject using the inhaler if the one or more measured values associated with volume of flow and velocity of flow each meet or exceed threshold values associated with the volume of flow and velocity of flow.

In some embodiments, operation 1020 includes administering the at least one active agent 214 to the subject when at least one value associated with an inhalation parameter meets or exceeds a threshold value (not shown). In some embodiments, system 100 may be used to administer at least one active agent 214 to a subject when at least one value associated with an inhalation parameter meets or exceeds a threshold value. For example, in some embodiments, a control unit 108 may receive one or more signals that include one or more assessed values associated with velocity of flow through one or more flow channels 104 disposed within an inhaler used by a subject during an inhalation cycle from a sensor 114. The control unit 108 may compare the one or more assessed values to one or more threshold values associated with the velocity of flow and activate one or more actuators 120 to facilitate at least partial release of one or more active agents 214 from one or more active agent reservoirs 212 to administer the one or more active agents 214 to the subject using the inhaler if the one or more assessed values associated with the velocity of flow during the inhalation cycle meet or exceed the one or more threshold values.

In some embodiments, operation 1020 includes administering the at least one active agent 214 to the subject when at least one value associated with a breath hold parameter meets or exceeds a threshold value (not shown). In some embodiments, system 100 may be used to administer at least one active agent 214 to a subject when at least one value associated with a breath hold parameter meets or exceeds a threshold value. For example, in some embodiments, a control unit 108 may receive one or more signals that include one or more assessed time values associated with a breath hold period by a subject using an inhaler. The control unit 108 may compare the one or more assessed time values to one or more threshold time values associated with a breath hold period and activate one or more actuators 120 to facilitate at least partial release of one or more active agents 214 from one or more active agent reservoirs 212 to administer the one or more active agents 214 to the subject using the inhaler if the one or more assessed time values associated with the breath hold period meets or exceeds the one or more threshold values. In some embodiments, a control unit 108 may receive one or more signals that include one or more assessed values associated with a volume of flow held by a subject using an inhaler during a breath hold period from a sensor 114. The control unit 108 may compare the one or more assessed values associated with the volume of flow held to one or more threshold values associated with a volume of flow. The control unit 108 may activate one or more actuators 120 to facilitate at least partial release of one or more active agents 214 from one or more active agent reservoirs 212 to deliver the one or more active agents 214 to the subject using the inhaler if the one or more assessed values associated with the volume of flow held by the subject during a breath hold cycle meet or exceed the one or more threshold values.

In some embodiments, operation 1020 includes administering the at least one active agent 214 to the subject when at least one value associated with an exhalation parameter meets or exceeds a threshold value (not shown). In some embodiments, system 100 may be used to administer at least one active agent 214 to a subject when at least one value associated with an exhalation parameter meets or exceeds a threshold value. For example, in some embodiments, a control unit 108 may receive one or more signals that include one or more assessed values associated with a volume of flow through one or more flow channels 104 disposed within an inhaler used by a subject during an exhalation cycle from a sensor 114. The control unit 108 may compare the one or more assessed values to one or more threshold values associated with the volume of flow and activate one or more actuators 120 to facilitate at least partial release of one or more active agents 214 from one or more active agent reservoirs 212 to administer the one or more active agents 214 to the subject using the inhaler if the one or more assessed values associated with the volume of flow meet or exceed the one or more threshold values. In some embodiments, a control unit 108 may activate an actuator 120 to facilitate at least partial release from one or more active agent reservoirs 212 at the beginning of an inhalation cycle that follows an exhalation cycle where the volume of flow that was exhaled meets or exceeds a threshold value.

In some embodiments, operation 1020 includes administering the at least one active agent 214 to the subject when at least one value associated with an exhalation parameter meets or exceeds a threshold value and when at least one value associated with an inhalation parameter meets or exceeds a threshold value (not shown). In some embodiments, system 100 may be used to administer at least one active agent 214 to a subject when at least one value associated with an exhalation parameter meets or exceeds a threshold value and when at least one value associated with an inhalation parameter meets or exceeds a threshold value. For example, in some embodiments, a control unit 108 may receive one or more signals that include one or more assessed values associated with volume of flow through one or more flow channels 104 disposed within an inhaler used by a subject during an exhalation cycle from a sensor 114. The control unit 108 may compare the one or more assessed values to one or more threshold values associated with the volume of flow. The control unit 108 may then receive one or more signals that include one or more assessed values associated with velocity of flow through one or more flow channels 104 disposed within the inhaler used by the subject during an inhalation cycle and compare the one or more assessed values to one or more threshold values associated with the velocity of flow. The control unit 108 may then activate an actuator 120 to facilitate at least partial release from one or more active agent reservoirs 212 during the inhalation cycle if the velocity of flow during the inhalation cycle meets or exceeds a threshold value and the volume of flow that was exhaled meets or exceeds a threshold value.

In some embodiments, operation 1030 includes administering the at least one incentive agent 218 after the at least one active agent 214 is administered (not shown). In some embodiments, system 100 may be used to administer at least one incentive agent 218 after at least one active agent 214 is administered. In some embodiments, a control unit 108 may direct one or more actuators 120 to facilitate at least partial release from one or more active agent reservoirs 212 to administer one or more active agents 214 to a subject using an inhaler and then direct one or more actuators 120 to facilitate at least partial release from one or more incentive agent reservoirs 216 to administer one or more incentive agents 218 to the subject.

In some embodiments, operation 1030 includes administering the at least one incentive agent 218 substantially concurrently with the at least one active agent 214 (not shown). In some embodiments, system 100 may be used to administer the at least one incentive agent 218 substantially concurrently with the at least one active agent 214. In some embodiments, a control unit 108 may direct one or more actuators 120 to facilitate at least partial release from one or more active agent reservoirs 212 to administer one or more active agents 214 to a subject using an inhaler and direct one or more actuators 120 to facilitate at least partial release from one or more incentive agent reservoirs 216 to administer one or more incentive agents 218 to the subject at substantially the same time.

In some embodiments, operation 1030 includes administering the at least one incentive agent 218 before the at least one active agent 214 is administered (not shown). In some embodiments, system 100 may be used to administer at least one incentive agent 218 before at least one active agent 214 is administered. In some embodiments, a control unit 108 may direct one or more actuators 120 to facilitate at least partial release from one or more incentive agent reservoirs 216 to administer one or more incentive agents 218 to a subject using an inhaler and then direct one or more actuators 120 to facilitate at least partial release from one or more active agent reservoirs 212 to administer one or more active agents 214 to the subject at a later time.

In some embodiments, operation 1030 includes administering caffeine (not shown). In some embodiments, system 100 may be used to administer caffeine. In some embodiments, a control unit 108 may direct one or more actuators 120 to facilitate at least partial release from one or more incentive agent reservoirs 216 to administer caffeine to a subject using an inhaler.

In some embodiments, operation 1030 includes administering nicotine (not shown). In some embodiments, system 100 may be used to administer nicotine. In some embodiments, a control unit 108 may direct one or more actuators 120 to facilitate at least partial release from one or more incentive agent reservoirs 216 to administer nicotine to a subject using an inhaler.

In some embodiments, operation 1030 includes administering a flavoring agent (not shown). In some embodiments, system 100 may be used to administer a flavoring agent. In some embodiments, a control unit 108 may direct one or more actuators 120 to facilitate at least partial release from one or more incentive agent reservoirs 216 to administer a flavoring agent to a subject using an inhaler. Numerous types of flavoring agents may be administered. Examples of flavoring agents include, but are not limited to, orange flavoring agents, lemon flavoring agents, cherry flavoring agents, and the like.

In some embodiments, operation 1030 includes administering menthol (not shown). In some embodiments, system 100 may be used to administer menthol. In some embodiments, a control unit 108 may direct one or more actuators 120 to facilitate at least partial release from one or more incentive agent reservoirs 216 to administer menthol to a subject using an inhaler.

In some embodiments, operation 1030 includes administering the at least one incentive agent 218 in a quantity that is based on a quantity of the at least one active agent 214 that was delivered to the subject (not shown). In some embodiments, system 100 may be used to administer at least one incentive agent 218 in a quantity that is based on a quantity of at least one active agent 214 that was delivered to a subject. In some embodiments, an optical sensor 126 may be used to assess a quantity of one or more active agents 214 that flow through one or more flow channels 104 disposed within an inhaler that is used by a subject. In some embodiments, a phase Doppler interferometer 136 may be used to assess a quantity of one or more active agents 214 that flow through one or more flow channels 104 disposed within an inhaler that is used by a subject. In some embodiments, an ultrasonic flow meter 140 may be used to assess a quantity of one or more active agents 214 that flow through one or more flow channels 104 disposed within an inhaler that is used by a subject. In some embodiments, a sensor 114 may transmit one or more signals that include one or more assessed values associated with a quantity of one or more active agents 214 to a control unit 108 that uses one or more assessed values to determine a quantity of one or more active agents 214 that were delivered to a subject using the inhaler. The control unit 108 may then direct one or more actuators 120 to facilitate at least partial release from one or more incentive agent reservoirs 216 to administer one or more incentive agents 218 to a subject using the inhaler in a quantity that is related to the quantity of one or more active agents 214 that were administered to the subject. In some embodiments, the quantity of an incentive agent 218 may be proportional to the quantity of one or more active agents 214 that were administered to the subject.

In some embodiments, operation 1030 includes administering the at least one incentive agent 218 in response to assessing the one or more parameters associated with use of the inhaler (not shown). In some embodiments, system 100 may be used to administer at least one incentive agent 218 in response to assessing one or more parameters associated with use of the inhaler. An incentive agent 218 may be administered in response to assessing numerous types of parameters. Examples of such parameters include, but are not limited to, parameters associated with inhalation through an inhaler, parameters associated with exhalation through an inhaler, parameters associated with breath holding while using an inhaler, parameters associated with administration of one or more active agents 214 to a subject using an inhaler, parameters associated with administration of one or more incentive agents 218 to a subject using an inhaler, and the like. In some embodiments, a sensor 114 may be configured to assess a quantity of one or more active agents 214 that are administered to a subject through use of an inhaler. The sensor 114 may transmit one or more signals that include the one or more assessed values associated with the quantity of one or more active agents 214 that are administered to a subject to a control unit 108. The control unit 108 may determine if the one or more assessed values meet or exceed a preselected dosage of the one or more active agents 214 that are to be administered to the subject using the inhaler. If the one or more values meet or exceed a preselected dosage the control unit 108 may direct an actuator 120 to facilitate at least partial release from one or more incentive agent reservoirs 216 to administer one or more incentive agents 218 to the subject using the inhaler. In some embodiments, a sensor 114 may be configured to assess one or more values associated with a quality of physical contact between the mouth of the subject and the inhaler. The sensor 114 may transmit one or more signals that include the one or more assessed values associated with the quality of physical contact to a control unit 108. The control unit 108 may determine if the one or more assessed values meet or exceed a preselected value. If the one or more values meet or exceed a preselected value the control unit 108 may direct an actuator 120 to facilitate at least partial release from one or more incentive agent reservoirs 216 to administer one or more incentive agents 218 to the subject using the inhaler.

In some embodiments, operation 1030 includes administering the at least one incentive agent 218 in response to assessing at least one value associated with a respiration parameter associated with use of the inhaler (not shown). In some embodiments, system 100 may be used to administer at least one incentive agent 218 in response to assessing at least one value associated with a respiration parameter associated with use of the inhaler. An incentive agent 218 may be administered in response to assessing numerous parameters related to respiration performance by a subject. Examples of such parameters include, but are not limited to, velocity of flow through one or more flow channels disposed within an inhaler during an inhalation cycle, velocity of flow through one or more flow channels disposed within an inhaler during an exhalation cycle, volume of flow through one or more flow channels disposed within an inhaler during an inhalation cycle, volume of flow through one or more flow channels disposed within an inhaler during an exhalation cycle, and the like. In some embodiments, an incentive agent 218 may be administered to a subject using an inhaler in response to the performance of the subject using the inhaler. For example, in some embodiments, a flow sensor 124 may measure the volume of flow through one or more flow channels 104 disposed within an inhaler and transmit one or more signals that include the one or more assessed values associated with the volume of flow to a control unit 108. The control unit 108 may determine if the one or more assessed values associated with the volume of flow meet or exceed a threshold value associated with a volume of flow through the inhaler. If the one or more assessed values meet or exceed a threshold value, the control unit 108 may direct an actuator 120 to facilitate at least partial release from one or more incentive agent reservoirs 216 to administer one or more incentive agents 218 to the subject using the inhaler.

In some embodiments, operation 1030 includes administering the at least one incentive agent 218 in response to assessing at least one value associated with an inhalation parameter associated with use of the inhaler (not shown). In some embodiments, system 100 may be used to administer at least one incentive agent 218 in response to assessing at least one value associated with an inhalation parameter associated with use of the inhaler. An incentive agent 218 may be administered in response to assessing numerous parameters related to inhalation performance by a subject. Examples of such parameters include, but are not limited to, velocity of flow through one or more flow channels disposed within an inhaler during an inhalation cycle, volume of flow through one or more flow channels disposed within an inhaler during an inhalation cycle, and the like. In some embodiments, a flow sensor 124 may assess the volume of flow through one or more flow channels 104 disposed within an inhaler during an inhalation cycle by a subject using the inhaler and transmit one or more signals that include the one or more values associated with the assessed volume of flow to a control unit 108. The control unit 108 may determine if the one or more assessed values associated with the measured volume of flow meet or exceed a threshold value associated with a volume of flow through the inhaler. If the assessed flow meets or exceeds a threshold value, the control unit 108 may direct an actuator to facilitate at least partial release from one or more incentive agent reservoirs 216 to administer one or more incentive agents 218 to the subject using the inhaler.

In some embodiments, operation 1030 includes administering the at least one incentive agent 218 in response to assessing at least one value associated with a breath hold parameter associated with use of the inhaler (not shown). In some embodiments, system 100 may be used to administer at least one incentive agent 218 in response to assessing at least one value associated with a breath hold parameter associated with use of the inhaler. An incentive agent 218 may be administered in response to assessing numerous parameters related to breath hold performance by a subject using an inhaler. Examples of such parameters include, but are not limited to, volume of flow held during a breath hold cycle, length of a breath hold cycle, and the like. In some embodiments, a flow sensor 124 may assess the volume of flow that is held during a breath hold cycle by a subject using the inhaler and transmit one or more signals that include the one or more values associated with the assessed volume of flow to a control unit 108. The control unit 108 may determine if the one or more values associated with the assessed volume of flow meet or exceed a threshold value associated with a volume of flow through the inhaler. If the one or more assessed values meet or exceed a threshold value, the control unit 108 may direct an actuator 120 to facilitate at least partial release from one or more incentive agent reservoirs 216 to administer one or more incentive agents 218 to the subject using the inhaler. In some embodiments, a timer 134 may assess the time of a breath hold cycle by a subject using the inhaler and transmit one or more signals that include the one or more values associated with the assessed time to a control unit 108. The control unit 108 may determine if the one or more assessed values associated with the time of the breath hold cycle meet or exceed a threshold value associated with the time. If the one or more assessed time values meet or exceed a threshold value, the control unit 108 may direct an actuator 120 to facilitate at least partial release from one or more incentive agent reservoirs 216 to administer one or more incentive agents 218 to the subject using the inhaler.

In some embodiments, operation 1030 includes administering the at least one incentive agent 218 in response to assessing at least one value associated with an exhalation parameter associated with use of the inhaler (not shown). In some embodiments, system 100 may be used to administer at least one incentive agent 218 in response to assessing at least one value associated with an exhalation parameter associated with use of the inhaler. An incentive agent 218 may be administered in response to assessing numerous parameters related to exhalation performance by a subject. Examples of such parameters include, but are not limited to, velocity of flow through one or more flow channels 104 disposed within an inhaler during an exhalation cycle, volume of flow through one or more flow channels 104 disposed within an inhaler during an exhalation cycle, and the like. In some embodiments, a flow sensor 124 may assess the volume of flow through one or more flow channels 104 disposed within an inhaler during an exhalation cycle by a subject using the inhaler and transmit one or more signals that include one or more values associated with the assessed volume of flow to a control unit 108. The control unit 108 may determine if the one or more assessed values associated with the volume of flow meet or exceed a threshold value associated with a volume of flow through the inhaler. If the assessed flow meets or exceeds a threshold value, the control unit 108 may direct an actuator 120 to facilitate at least partial release from one or more incentive agent reservoirs 216 to administer one or more incentive agents 218 to the subject using the inhaler.

In some embodiments, operation 1030 includes administering the at least one incentive agent 218 to the subject when at least one value associated with the one or more parameters associated with use of the inhaler meets or exceeds a threshold value (not shown). In some embodiments, system 100 may be used to administer at least one incentive agent 218 to the subject when at least one value associated with one or more parameters associated with use of the inhaler meets or exceeds a threshold value. Numerous parameters associated with use of an inhaler may be assessed. In some embodiments, such parameters may include, but are not limited to, velocity of flow through one or more flow channels 104 disposed within an inhaler during an inhalation cycle, a breath hold cycle, or an exhalation cycle. In some embodiments, such parameters may include, but are not limited to, volume of flow through one or more flow channels 104 disposed within an inhaler during an inhalation cycle, a breath hold cycle, or an exhalation cycle. In some embodiments, such parameters may be associated with the quality of physical contact between the mouth of the subject and the inhaler. Accordingly, in some embodiments, a sensor 114 may assess one or more values associated with one or more parameters associated with use of an inhaler. The sensor 114 may transmit one or more signals that include the one or more assessed values to a control unit 108 that determines if the one or more assessed values meet or exceed one or more threshold values associated with the one or more parameters. If the one or more assessed values meet or exceed one or more threshold values, the control unit 108 may direct an actuator 120 to facilitate at least partial release from one or more incentive agent reservoirs 216 to administer one or more incentive agents 218 to the subject using the inhaler.

In some embodiments, operation 1030 includes administering the at least one incentive agent to the subject when at least one value associated with a respiration parameter meets or exceeds a threshold value (not shown). In some embodiments, system 100 may be used to administer at least one incentive agent to a subject when at least one value associated with a respiration parameter meets or exceeds a threshold value. Numerous respiration parameters may be assessed. In some embodiments, such parameters may include, but are not limited to, velocity of flow through one or more flow channels 104 disposed within an inhaler during an inhalation cycle, a breath hold cycle, or an exhalation cycle. In some embodiments, such parameters may include, but are not limited to, volume of flow through one or more flow channels 104 disposed within an inhaler during an inhalation cycle, a breath hold cycle, or an exhalation cycle. Accordingly, in some embodiments, a sensor 114 may assess one or more values associated with one or more respiration parameters and transmit one or more signals that include the one or more assessed values to a control unit 108. The control unit 108 may determine if the one or more assessed values meet or exceed one or more threshold values associated with the one or more respiration parameters. If the one or more assessed values meet or exceed one or more threshold values, the control unit 108 may direct an actuator 120 to facilitate at least partial release from one or more incentive agent reservoirs 216 to administer one or more incentive agents 218 to the subject using the inhaler.

In some embodiments, operation 1030 includes administering the at least one incentive agent to the subject when at least one value associated with an inhalation parameter meets or exceeds a threshold value (not shown). In some embodiments, system 100 may be used to administer at least one incentive agent to a subject when at least one value associated with an inhalation parameter meets or exceeds a threshold value. Numerous inhalation parameters may be assessed. In some embodiments, such inhalation parameters may include, but are not limited to, velocity of flow through one or more flow channels 104 disposed within an inhaler during an inhalation cycle, volume of flow through one or more flow channels 104 disposed within an inhaler during an inhalation cycle, a period of time associated with an inhalation cycle, a quantity of active agent 214 released from an active agent reservoir 212 during an inhalation cycle, and the like. Accordingly, in some embodiments, a sensor 114 may assess one or more values associated with one or more inhalation parameters and transmit one or more signals that include the one or more assessed values to a control unit 108. The control unit 108 may determine if the one or more assessed values meet or exceed one or more threshold values associated with the one or more inhalation parameters. If the one or more assessed values meet or exceed one or more threshold values, the control unit 108 may direct an actuator 120 to facilitate at least partial release from one or more incentive agent reservoirs 216 to administer one or more incentive agents 218 to the subject using the inhaler.

In some embodiments, operation 1030 includes administering the at least one incentive agent to the subject when at least one value associated with a breath hold parameter meets or exceeds a threshold value (not shown). In some embodiments, system 100 may be used to administer at least one incentive agent to a subject when at least one value associated with a breath hold parameter meets or exceeds a threshold value. Numerous breath hold parameters may be assessed. In some embodiments, such breath hold parameters may include, but are not limited to, a volume of flow held during a breath hold cycle, a time period associated with a breath hold cycle, a quantity of active agent 214 administered to a subject during an inhalation cycle preceding a breath hold cycle, and the like. Accordingly, in some embodiments, a sensor 114 may assess one or more values associated with one or more breath hold parameters and transmit one or more signals that include the one or more assessed values to a control unit 108. The control unit 108 may determine if the one or more assessed values meet or exceed one or more threshold values associated with the one or more breath hold parameters. If the one or more assessed values meet or exceed one or more threshold values, the control unit 108 may direct an actuator 120 to facilitate at least partial release from one or more incentive agent reservoirs 216 to administer one or more incentive agents 218 to the subject using the inhaler.

In some embodiments, operation 1030 includes administering the at least one incentive agent to the subject when at least one value associated with an exhalation parameter meets or exceeds a threshold value (not shown). In some embodiments, system 100 may be used to administer at least one incentive agent to a subject when at least one value associated with an exhalation parameter meets or exceeds a threshold value. Numerous exhalation parameters may be assessed. In some embodiments, such exhalation parameters may include, but are not limited to, a volume of flow through one or more flow channels disposed within an inhaler during an exhalation cycle, a time period associated with an exhalation cycle, and the like. Accordingly, in some embodiments, a sensor 114 may assess one or more values associated with one or more exhalation parameters and transmit one or more signals that include the one or more assessed values to a control unit 108. The control unit 108 may determine if the one or more assessed values meet or exceed one or more threshold values associated with the one or more exhalation parameters. If the one or more assessed values meet or exceed one or more threshold values, the control unit 108 may direct an actuator 120 to facilitate at least partial release from one or more incentive agent reservoirs 216 to administer one or more incentive agents 218 to the subject using the inhaler.

In some embodiments, operation 1030 includes administering the at least one incentive agent to the subject when at least one value associated with an exhalation parameter meets or exceeds a threshold value and when at least one value associated with an inhalation parameter meets or exceeds a threshold value (not shown). In some embodiments, system 100 may be used to administer at least one incentive agent to a subject when at least one value associated with an exhalation parameter meets or exceeds a threshold value and when at least one value associated with an inhalation parameter meets or exceeds a threshold value. Numerous exhalation parameters may be assessed. Examples of such exhalation parameters include, but are not limited to, velocity of flow through one or more flow channels disposed within an inhaler during an exhalation cycle by a subject using the inhaler, volume of flow through one or more flow channels disposed within an inhaler during an exhalation cycle by a subject using the inhaler, a period of time associated with an exhalation cycle by a subject using the inhaler, and the like. Numerous inhalation parameters may be assessed. Examples of such inhalation parameters include, but are not limited to, velocity of flow through one or more flow channels disposed within an inhaler during an inhalation cycle by a subject using the inhaler, volume of flow through one or more flow channels disposed within an inhaler during an inhalation cycle by a subject using the inhaler, a period of time associated with an inhalation cycle by a subject using the inhaler, and the like. Accordingly, in some embodiments, a sensor 114 may assess one or more values associated with one or more exhalation parameters and transmit one or more signals that include the one or more assessed values to a control unit 108. The control unit 108 may determine if the one or more assessed values meet or exceed one or more threshold values associated with the one or more exhalation parameters. A sensor 114 may assess one or more values associated with one or more inhalation parameters and transmit one or more signals that include the one or more assessed values to a control unit 108. The control unit 108 may determine if the one or more assessed values meet or exceed one or more threshold values associated with the one or more inhalation parameters. If the one or more assessed values associated with the one or more exhalation parameters and the one or more inhalation parameters meet or exceed one or more threshold values, the control unit 108 may direct an actuator 120 to facilitate at least partial release from one or more incentive agent reservoirs 216 to administer one or more incentive agents 218 to the subject using the inhaler.

Figure 11:
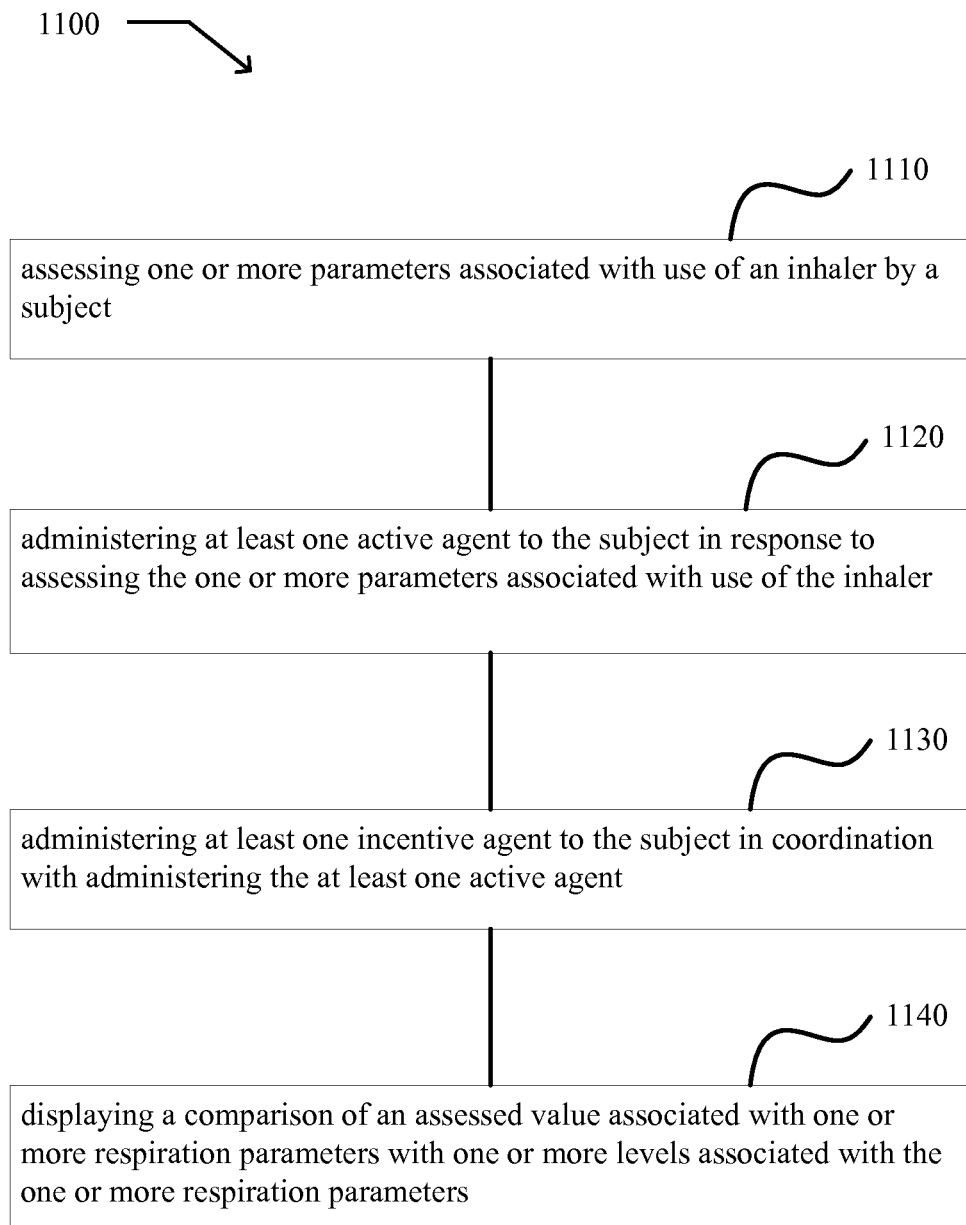
FIG. 11 illustrates an example operational flow 1100 in which embodiments may be implemented.

FIG. 11 illustrates operational flow 1100 that includes operation 1110 that includes assessing one or more parameters associated with use of an inhaler by a subject, operation 1120 that includes administering at least one active agent 214 to the subject in response to assessing the one or more parameters associated with use of the inhaler, operation 1130 that includes administering at least one incentive agent 218 to the subject in coordination with administering the at least one active agent 214, and operation 1140 that includes displaying a comparison of an assessed value associated with one or more respiration parameters with one or more levels associated with the one or more respiration parameters. Operations 1110, 1120, and 1130 correspond to operations 1010, 1020, and 1030 as previously described with reference to FIG. 10.

In FIG. 11 and in the following description that includes various examples of operations used during performance of the method, discussion and explanation may be provided with respect to any one or combination of the above-described examples, and/or with respect to other examples and contexts. However, it should be understood that the operations may be executed in a number of other environments and contexts, and/or modified versions of the figures. Also, although the various operations are presented in the sequence(s) illustrated, it should be understood that the various operations may be performed in other orders than those which are illustrated, or may be performed concurrently.

Operation 1140 includes displaying a comparison of an assessed value associated with one or more respiration parameters with one or more levels associated with the one or more respiration parameters. In some embodiments, system 100 may display a comparison of an assessed value associated with one or more respiration parameters with one or more levels associated with the one or more respiration parameters. In some embodiments, one or more performance indicators 116 may display a comparison of an assessed value associated with one or more respiration parameters with one or more levels associated with the one or more respiration parameters. A performance indicator 116 may display a comparison of numerous assessed values to numerous levels associated with one or more respiration parameters. A performance indicator 116 may display a comparison in numerous formats. For example, in some embodiments, a performance indicator 116 may display a comparison in a numeric format. In some embodiments, a performance indicator 116 may display a comparison in a colorimetric format. In some embodiments, a performance indicator 116 may display a comparison in an audio format. Examples of respiration parameters include, but are not limited to, volume of flow through one or more flow channels 104 disposed within an inhaler, velocity of flow through one or more flow channels 104 disposed within an inhaler, a time period associated with flow through one or more flow channels 104 disposed within an inhaler, and the like. In some embodiments, a performance indicator 116 may display the quality of physical contact between the mouth of a subject and a mouthpiece 268 associated with an inhaler. In some embodiments, a flow sensor 124 may be used to assess a value associated with flow through one or more flow channels 104 disposed within an inhaler used by a subject during an inhalation cycle. The flow sensor 124 may transmit one or more signals 112 that include the assessed value to a performance indicator 116 that displays a comparison of the assessed value with one or more levels associated with flow through the one or more flow channels 104 during an inhalation cycle. In some embodiments, the flow sensor 124 may transmit one or more signals 112 that include an assessed value associated with flow through one or more flow channels 104 to a control unit 108 that processes the information and then transmits one or more signals 112 to a performance indicator 116 that displays a comparison of the assessed value with one or more levels associated with flow through the one or more flow channels 104. In some embodiments, such levels associated with one or more respiration parameters may be threshold levels. For example, in some embodiments, such levels may represent either or both of an upper and lower flow level that are associated with a desired level of flow though one or more flow channels 104 disposed within an inhaler.

In some embodiments, operation 1140 includes displaying a comparison of the assessed value associated with one or more respiration parameters to a range of levels associated with the one or more respiration parameters and instructing the subject to achieve a value of the one or more respiration parameters that is within a range of threshold levels associated with the one or more respiration parameters (not shown). In some embodiments, system 100 may be used to display a comparison of an assessed value associated with one or more respiration parameters to a range of levels associated with the one or more respiration parameters and instruct a subject to achieve a value of the one or more respiration parameters that is within a range of threshold levels associated with the one or more respiration parameters. Values related to numerous respiration parameters may be assessed and compared to ranges associated with the respiration parameters. Examples of such respiration parameters include, but are not limited to, velocity of flow through one or more flow channels 104 disposed within an inhaler, volume of flow through one or more flow channels 104 disposed within an inhaler, time of flow through one or more flow channels 104 disposed within an inhaler, amount of active agent 214 flowing through one or more flow channels 104 disposed within an inhaler, amount of incentive agent 218 flowing through one or more flow channels 104 disposed within an inhaler, and the like. For example, in some embodiments, a flow sensor 124 may be used to assess one or more values associated with volume of flow through one or more flow channels 104 disposed within an inhaler when the inhaler is used by a subject. The flow sensor 124 may transmit one or more signals 112 that include the one or more assessed values to a performance indicator 116 which displays the one or more assessed values in comparison to a range of levels associated with one or more parameters associated with a volume of flow. In some embodiments, a velocimeter 138 may be configured to determine one or more values associated with the velocity of flow during an inhalation cycle and an exhalation cycle through one or more flow channels 104 disposed within an inhaler used by a subject. The velocimeter 138 may transmit one or more signals 112 that include the one or more assessed values to a performance indicator 116 that displays the one or more assessed values in comparison to one or more ranges of levels associated with the velocity of flow. In some embodiments, a performance indicator 116 may instruct a subject to achieve one or more values associated with one or more respiration parameters that is within the range of levels associated with the one or more respiration parameters. For example, in some embodiments, a performance indicator 116 may instruct a subject to increase volume of flow through one or more flow channels 104 disposed within an inhaler. In some embodiments, a performance indicator 116 may instruct a subject to decrease volume of flow through one or more flow channels 104 disposed within an inhaler. In some embodiments, a performance indicator 116 may instruct a subject to maintain their current level of flow through one or more flow channels 104 disposed within an inhaler. In some embodiments, a performance indicator 116 may instruct a subject to increase volume of flow during an exhalation cycle through one or more flow channels 104 disposed within an inhaler. In some embodiments, a performance indicator 116 may instruct a subject to decrease volume of flow during an exhalation cycle through one or more flow channels 104 disposed within an inhaler. In some embodiments, a performance indicator 116 may instruct a subject to maintain their current level of flow during an exhalation cycle through one or more flow channels 104 disposed within an inhaler. In some embodiments, a performance indicator 116 may instruct a subject to increase the length of a breath hold cycle while using an inhaler. In some embodiments, a performance indicator 116 may instruct a subject to decrease the length of a breath hold cycle while using an inhaler. In some embodiments, a performance indicator 116 may instruct a subject to maintain their current length of a breath hold cycle while using an inhaler. Accordingly, in some embodiments, a performance indicator 116 may be used to instruct a subject with regard to numerous respiration parameters. In some embodiments, a control unit 108 may be operably coupled with one or more sensors 114 that are configured to assess one or more values associated with one or more respiration parameters. The control unit 108 may receive one or more signals 112 that include the one or more assessed values related to one or more respiration parameters from the one or more sensors 114 and then direct one or more performance indicators 116 to display a comparison of the one or more assessed values to one or more ranges of levels associated with the one or more respiration parameters. In some embodiments, a control unit 108 may receive one or more signals 112 that include one or more assessed values related to one or more respiration parameters from one or more sensors 114 and then direct one or more performance indicators 116 to instruct a subject to achieve a value of the one or more respiration parameters that is within the range of levels associated with the one or more respiration parameters.

In some embodiments, operation 1140 includes displaying a comparison of the assessed value associated with one or more inhalation parameters to a range of levels associated with the one or more inhalation parameters and instructing the subject to achieve a value of the one or more inhalation parameters that is within a range of threshold levels associated with the one or more inhalation parameters (not shown). In some embodiments, system 100 may be used to display a comparison of an assessed value associated with one or more inhalation parameters to a range of levels associated with the one or more inhalation parameters and instruct a subject to achieve a value of the one or more inhalation parameters that is within a range of threshold levels associated with the one or more inhalation parameters. Values related to numerous inhalation parameters may be assessed and compared to ranges of levels associated with the inhalation parameters. Examples of such inhalation parameters include, but are not limited to, velocity of flow through one or more flow channels 104 disposed within an inhaler during an inhalation cycle, volume of flow through one or more flow channels 104 disposed within an inhaler during an inhalation cycle, time of flow through one or more flow channels 104 disposed within an inhaler during an inhalation cycle, amount of active agent 214 flowing through one or more flow channels 104 disposed within an inhaler during an inhalation cycle, amount of incentive agent 218 flowing through one or more flow channels 104 disposed within an inhaler during an inhalation cycle, and the like. For example, in some embodiments, a flow sensor 124 may be used to assess one or more values associated with volume of flow through one or more flow channels 104 disposed within an inhaler during an inhalation cycle. The flow sensor 124 may transmit one or more signals 112 that include the one or more assessed values to a performance indicator 116 which displays a comparison of the one or more assessed values to a range of levels associated with one or more inhalation parameters. In some embodiments, a velocimeter 138 may be used to assess one or more values associated with the velocity of flow through one or more flow channels 104 disposed within an inhaler during an inhalation cycle. The velocimeter 138 may transmit one or more signals 112 that include the one or more assessed values to a performance indicator 116 that displays the one or more assessed values in comparison to one or more ranges of levels associated with the one or more inhalation parameters. The performance indicator 116 may display the comparison in numerous formats. In some embodiments, a performance indicator 116 may instruct a subject to achieve one or more values associated with one or more inhalation parameters that is within the range of levels associated with the one or more inhalation parameters. For example, in some embodiments, a performance indicator 116 may instruct a subject to increase the velocity of flow through an inhaler. In some embodiments, a performance indicator 116 may instruct a subject to decrease the velocity of flow through an inhaler. In some embodiments, a performance indicator 116 may instruct a subject to maintain a velocity of flow through an inhaler. In some embodiments, a performance indicator 116 may instruct a subject using an inhaler to increase the time period of an inhalation cycle through an inhaler. In some embodiments, a performance indicator 116 may instruct a subject to decrease the time period of an inhalation cycle through an inhaler. In some embodiments, a performance indicator 116 may instruct a subject to maintain the time period of an inhalation cycle through an inhaler. Accordingly, in some embodiments, a performance indicator 116 may be used to instruct a subject with regard to numerous inhalation parameters. In some embodiments, a control unit 108 may be operably coupled with one or more sensors 114 that are configured to assess on or more values associated with one or more inhalation parameters. The control unit 108 may receive one or more signals 112 that include assessed values related to one or more inhalation parameters from the one or more sensors 114 and then direct one or more performance indicators 116 to display a comparison of the one or more assessed values to one or more ranges of levels associated with the one or more inhalation parameters. In some embodiments, a control unit 108 may receive one or more signals that include assessed values related to one or more inhalation parameters from the one or more sensors 114 and then direct one or more performance indicators 116 to instruct the subject to achieve a value of the one or more inhalation parameters that is within the range of levels associated with the one or more inhalation parameters.

In some embodiments, operation 1140 includes displaying a comparison of the assessed value associated with one or more breath hold parameters to a range of levels associated with the one or more breath hold parameters and instructing the subject to achieve a value of the one or more breath hold parameters that is within the range of threshold levels associated with the one or more breath hold parameters (not shown). In some embodiments, system 100 may be used to display a comparison of an assessed value associated with one or more breath hold parameters to a range of levels associated with the one or more breath hold parameters and instruct a subject to achieve a value of the one or more breath hold parameters that is within the range of threshold levels associated with the one or more breath hold parameters. Values related to numerous breath hold parameters may be assessed and compared to ranges of levels associated with the breath hold parameters. Examples of such breath hold parameters include, but are not limited to, a time period associated with a breath hold cycle, an inhaled volume associated with a breath hold cycle, a quantity of active agent 214 that is inhaled and held during a breath hold cycle, a quantity of an incentive agent 218 that is inhaled and held during a breath hold cycle, and the like. For example, in some embodiments, a flow sensor 124 may be used to assess one or more values associated with a volume of flow that is held during a breath hold cycle. In some embodiments, a timer 134 may be used to assess one or more values associated with a time period associated with a breath hold cycle. In some embodiments, a sensor 114 may transmit one or more signals 112 that include one or more assessed values to a performance indicator 116 which displays the one or more assessed values in comparison to a range of levels associated with one or more breath hold parameters. The performance indicator 116 may display the comparison in numerous formats. In some embodiments, a performance indicator 116 may instruct a subject to achieve one or more values associated with one or more breath hold parameters that are within a range of levels associated with the one or more breath hold parameters. For example, in some embodiments, a performance indicator 116 may instruct a subject to increase the volume of flow that is held during a breath hold cycle. In some embodiments, a performance indicator 116 may instruct a subject to decrease the volume of flow that is held during a breath hold cycle. In some embodiments, a performance indicator 116 may instruct a subject to increase the time period of a breath hold cycle. In some embodiments, a performance indicator 116 may instruct a subject to decrease the time period of a breath hold cycle. Accordingly, in some embodiments, a performance indicator 116 may be used to instruct a subject with regard to numerous breath hold parameters. In some embodiments, a control unit 108 may be operably coupled with one or more sensors 114 that are configured to assess on or more values associated with one or more breath hold parameters. The control unit 108 may receive one or more signals 112 that include assessed values related to one or more breath hold parameters from the one or more sensors 114 and then direct one or more performance indicators 116 to display a comparison of the one or more assessed values to one or more ranges of levels associated with the one or more breath hold parameters. In some embodiments, a control unit 108 may receive one or more signals 112 that include one or more assessed values related to one or more breath hold parameters from one or more sensors 114 and then direct one or more performance indicators 116 to instruct a subject to achieve a value of the one or more breath hold parameters that is within the range of levels associated with the one or more breath hold parameters.

In some embodiments, operation 1140 includes displaying a comparison of an assessed value associated with one or more exhalation parameters to a range of levels associated with the one or more exhalation parameters and instructing the subject to achieve a value of the one or more exhalation parameters that is within the range of threshold levels associated with the one or more exhalation parameters (not shown). In some embodiments, system 100 may be used to display a comparison of an assessed value associated with one or more exhalation parameters to a range of levels associated with the one or more exhalation parameters and instruct a subject to achieve a value of the one or more exhalation parameters that is within the range of threshold levels associated with the one or more exhalation parameters. Values related to numerous exhalation parameters may be assessed and compared to ranges of levels associated with the exhalation parameters. Examples of such exhalation parameters include, but are not limited to, velocity of flow through one or more flow channels 104 disposed within an inhaler during an exhalation cycle, volume of flow through one or more flow channels 104 disposed within an inhaler during an exhalation cycle, time of flow through one or more flow channels 104 disposed within an inhaler during an exhalation cycle, amount of active agent 214 flowing through one or more flow channels 104 disposed within an inhaler during an exhalation cycle, amount of incentive agent 218 flowing through one or more flow channels 104 disposed within an inhaler during an exhalation cycle, and the like. For example, in some embodiments, a flow sensor 124 may be used to assess one or more values associated with volume of flow through one or more flow channels 104 disposed within an inhaler during an exhalation cycle. The flow sensor 124 may transmit one or more signals 112 that include the one or more assessed values to a performance indicator 116 which displays a comparison of the one or more assessed values to a range of levels associated with one or more exhalation parameters. In some embodiments, a velocimeter 138 may be used to assess one or more values associated with the velocity of flow through one or more flow channels 104 disposed within an inhaler during an exhalation cycle. The velocimeter 138 may transmit one or more signals 112 that include the one or more assessed values to a performance indicator 116 that displays the one or more assessed values in comparison to one or more ranges of levels associated with the one or more exhalation parameters. The performance indicator 116 may display the comparison in numerous formats. In some embodiments, a performance indicator 116 may instruct a subject to achieve one or more values associated with one or more exhalation parameters that is within the range of levels associated with the one or more exhalation parameters. For example, in some embodiments, a performance indicator 116 may instruct a subject to increase the velocity of flow through an inhaler. In some embodiments, a performance indicator 116 may instruct a subject to decrease the velocity of flow through an inhaler. In some embodiments, a performance indicator 116 may instruct a subject to maintain a velocity of flow through an inhaler. In some embodiments, a performance indicator 116 may instruct a subject using an inhaler to increase the time period of an exhalation cycle through an inhaler. In some embodiments, a performance indicator 116 may instruct a subject to decrease the time period of an exhalation cycle through an inhaler. In some embodiments, a performance indicator 116 may instruct a subject to maintain the time period of an exhalation cycle through an inhaler. Accordingly, in some embodiments, a performance indicator 116 may be used to instruct a subject with regard to numerous exhalation parameters. In some embodiments, a control unit 108 may be operably coupled with one or more sensors 114 that are configured to assess on or more values associated with one or more exhalation parameters. The control unit 108 may receive one or more signals 112 that include an assessed value related to one or more exhalation parameters from the one or more sensors 114 and then direct one or more performance indicators 116 to display a comparison of the one or more assessed values to one or more ranges of levels associated with the one or more exhalation parameters. In some embodiments, a control unit 108 may receive one or more signals that include an assessed value related to one or more exhalation parameters from the one or more sensors 114 and then direct one or more performance indicators 116 to instruct the subject to achieve a value of the one or more exhalation parameters that is within the range of levels associated with the one or more exhalation parameters.

In some embodiments, operation 1140 includes displaying a comparison of an assessed value associated with one or more exhalation parameters to a range of levels associated with the one or more exhalation parameters and instructing the subject to achieve a value of the one or more exhalation parameters that is within the range of threshold levels associated with the one or more exhalation parameters and then displaying a comparison of an assessed value associated with one or more inhalation parameters to a range of levels associated with the one or more inhalation parameters and instructing the subject to achieve a value of the one or more inhalation parameters that is within the range of threshold levels associated with the one or more inhalation parameters (not shown). In some embodiments, system 100 may be used to display a comparison of an assessed value associated with one or more exhalation parameters to a range of levels associated with the one or more exhalation parameters and instruct a subject to achieve a value of the one or more exhalation parameters that is within the range of threshold levels associated with the one or more exhalation parameters and then display a comparison of an assessed value associated with one or more inhalation parameters to a range of levels associated with the one or more inhalation parameters and instruct the subject to achieve a value of the one or more inhalation parameters that is within the range of threshold levels associated with the one or more inhalation parameters. In some embodiments, a performance indicator 116 may display a comparison of one or more assessed exhalation parameters to a range of levels associated with the one or more exhalation parameters. For example, in some embodiments, a performance indicator 116 may receive one or more signals 112 that include one or more assessed values associated with one or more exhalation parameters from one or more sensors 114 and display the one or more values in comparison to a range of levels associated with the one or more exhalation parameters. In some embodiments, a control unit 108 may receive one or more signals 112 that include one or more assessed values that are associated with one or more exhalation parameters from one or more sensors 114 and then direct a performance indicator 116 to display the one or more values associated with one or more exhalation parameters in comparison to one or more levels associated with the one or more exhalation parameters. In some embodiments, a performance indicator 116 may instruct a subject to achieve a value of one or more exhalation parameters that are within a range of levels associated with the one or more exhalation parameters. In some embodiments, a control unit 108 may direct a performance indicator 116 to instruct a subject to achieve a value of one or more exhalation parameters that are within a range of levels associated with the one or more exhalation parameters. In some embodiments, a performance indicator 116 may display a comparison of one or more assessed inhalation parameters to a range of levels associated with the one or more inhalation parameters. For example, in some embodiments, a performance indicator 116 may receive one or more signals 112 that include one or more assessed values that are associated with one or more inhalation parameters from one or more sensors 114 and display the one or more values in comparison to a range of levels associated with the one or more inhalation parameters. In some embodiments, a control unit 108 may receive one or more signals 112 that include one or more assessed values associated with one or more inhalation parameters from one or more sensors 114 and then direct a performance indicator 116 to display the one or more values associated with one or more inhalation parameters in comparison to one or more levels associated with the one or more inhalation parameters. In some embodiments, a performance indicator 116 may instruct a subject to achieve a value of one or more inhalation parameters that are within a range of levels associated with the one or more inhalation parameters. In some embodiments, a control unit 108 may direct a performance indicator 116 to instruct a subject to achieve a value of one or more inhalation parameters that are within a range of levels associated with the one or more inhalation parameters.

Figure 12:
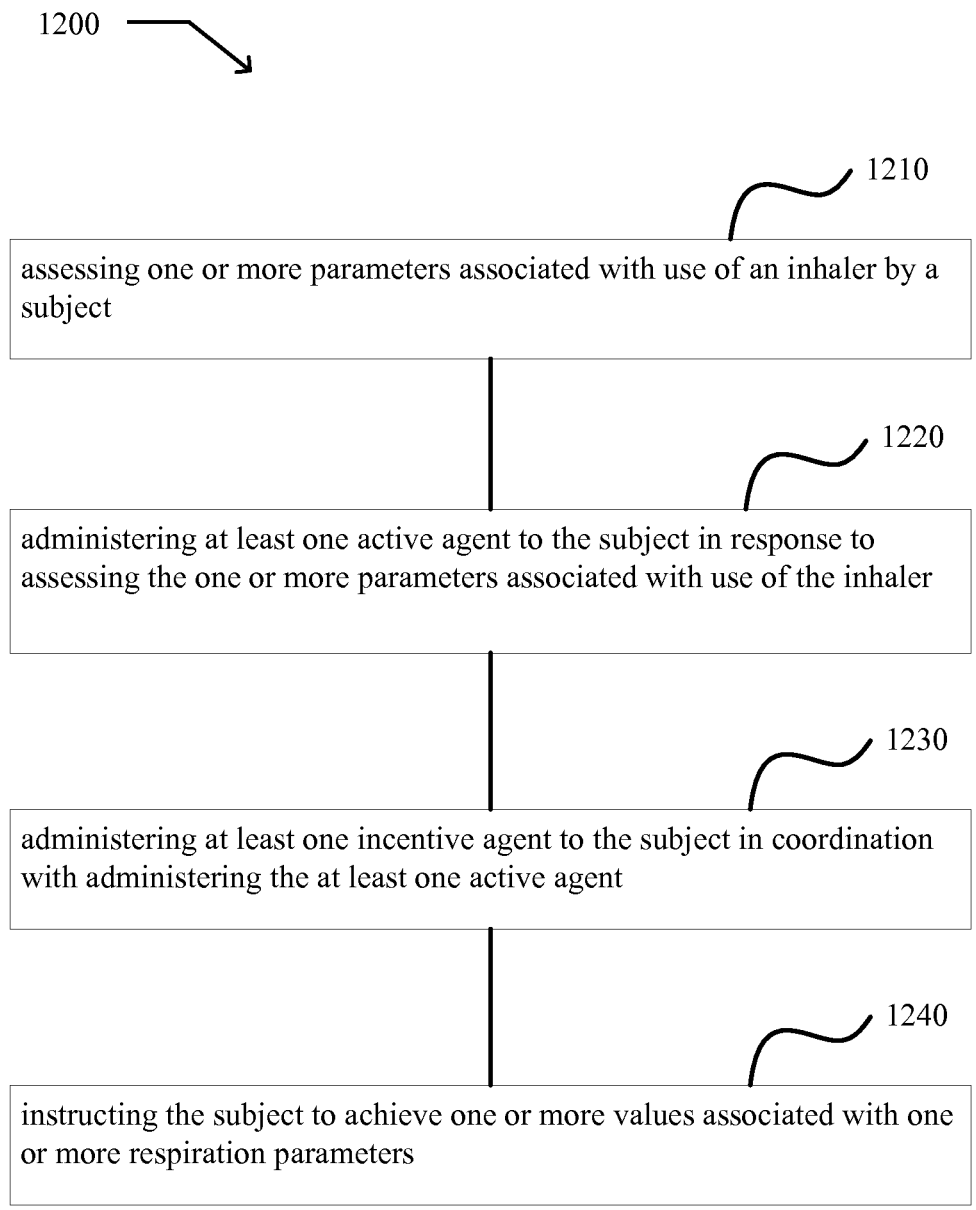
FIG. 12 illustrates an example operational flow 1200 in which embodiments may be implemented.

FIG. 12 illustrates operational flow 1200 that includes operation 1210 that includes assessing one or more parameters associated with use of an inhaler by a subject, operation 1220 that includes administering at least one active agent 214 to the subject in response to assessing the one or more parameters associated with use of the inhaler, operation 1230 that includes administering at least one incentive agent 218 to the subject in coordination with administering the at least one active agent 214, and operation 1240 that includes instructing the subject to achieve one or more values associated with one or more respiration parameters. Operations 1210, 1220, and 1230 correspond to operations 1010, 1020, and 1030 as previously described with reference to FIG. 10.

In FIG. 12 and in the following description that includes various examples of operations used during performance of the method, discussion and explanation may be provided with respect to any one or combination of the above-described examples, and/or with respect to other examples and contexts. However, it should be understood that the operations may be executed in a number of other environments and contexts, and/or modified versions of the figures. Also, although the various operations are presented in the sequence(s) illustrated, it should be understood that the various operations may be performed in other orders than those which are illustrated, or may be performed concurrently.

Operation 1240 includes instructing the subject to achieve one or more values associated with one or more respiration parameters. In some embodiments, system 100 may be used to instruct a subject to achieve one or more values associated with one or more respiration parameters. In some embodiments, a performance indicator 116 may instruct a subject to achieve one or more values associated with one or more respiration parameters. A performance indicator may instruct a subject to achieve one or more values associated with numerous types of respiration parameters. Examples of such respiration parameters include, but are not limited to, parameters associated with flow through one or more flow channels 104 disposed within an inhaler, release of one or more active agents 214 from one or more active agent reservoirs 212, release of one or more incentive agents 218 from one or more incentive agent reservoirs 216, and the like. For example, in some embodiments, a performance indicator 116 may instruct a subject to increase volume of flow through one or more flow channels 104 disposed within an inhaler. In some embodiments, a performance indicator 116 may instruct a subject to decrease volume of flow through one or more flow channels 104 disposed within an inhaler. In some embodiments, a performance indicator 116 may instruct a subject to maintain their current level of flow through one or more flow channels 104 disposed within an inhaler. In some embodiments, a performance indicator 116 may instruct a subject to increase volume of flow during an exhalation cycle through one or more flow channels 104 disposed within an inhaler. In some embodiments, a performance indicator 116 may instruct a subject to decrease volume of flow during an exhalation cycle through one or more flow channels 104 disposed within an inhaler. In some embodiments, a performance indicator 116 may instruct a subject to maintain their current level of flow during an exhalation cycle through one or more flow channels 104 disposed within an inhaler. In some embodiments, a performance indicator 116 may instruct a subject to increase the length of a breath hold cycle while using an inhaler. In some embodiments, a performance indicator 116 may instruct a subject to decrease the length of a breath hold cycle while using an inhaler. In some embodiments, a performance indicator 116 may instruct a subject to maintain their current length of a breath hold cycle while using an inhaler. Accordingly, in some embodiments, a performance indicator 116 may be used to instruct a subject with regard to numerous respiration parameters. In some embodiments, a control unit 108 may be operably coupled with one or more sensors 114 that are configured to assess one or more values associated with one or more respiration parameters. In some embodiments, a control unit 108 may receive one or more signals 112 that include one or more assessed values related to one or more respiration parameters from one or more sensors 114 and then direct one or more performance indicators 116 to instruct a subject to achieve a value assigned to the one or more respiration parameters.

In some embodiments, operation 1240 includes instructing the subject to achieve one or more values associated with one or more respiration parameters that meet or exceed one or more threshold levels associated with the one or more respiration parameters (not shown). In some embodiments, system 100 may be used to instruct a subject to achieve one or more values associated with one or more respiration parameters that meet or exceed one or more threshold levels associated with the one or more respiration parameters. In some embodiments, one or more performance indicators 116 may be configured to instruct a subject to achieve one or more values associated with one or more respiration parameters that meet or exceed one or more threshold levels associated with the one or more respiration parameters. For example, in some embodiments, a flow sensor 124 may assess a value associated with flow through one or more flow channels 104 disposed within an inhaler during an inhalation cycle by a subject using the inhaler. The flow sensor 124 may transmit one or more signals 112 that include the assessed value to a performance indicator 116. If the assessed value does not meet a minimum threshold value for flow, the performance indicator 116 may instruct the subject to increase flow through the one or more flow channels 104 during the inhalation cycle. In another example, a timer 134 may assess a breath holding period following an inhalation cycle and transmit one or more signals 112 that include the assessed value to a performance indicator 116. If the assessed breath holding value is below a breath holding threshold value the performance indicator 116 may instruct a subject to increase their breath holding period after an inhalation cycle. A performance indicator 116 may provide instructions to a subject in numerous formats. For example, in some embodiments, a performance indicator 116 may provide audible instructions. In some embodiments, a performance indicator 116 may provide visual instructions. In some embodiments, a performance indicator 116 may provide tactile instructions.

In some embodiments, operation 1240 includes instructing the subject to achieve one or more values associated with one or more respiration parameters that are within one or more ranges of levels associated with the one or more respiration parameters (not shown). In some embodiments, system 100 may be used to instruct a subject to achieve one or more values associated with one or more respiration parameters that are within one or more ranges of levels associated with the one or more respiration parameters. For example, in some embodiments, a flow sensor 124 may assess a value associated with flow through one or more flow channels 104 disposed within an inhaler during use of the inhaler by a subject. The flow sensor 124 may transmit one or more signals 112 that include the assessed value to a performance indicator 116. If the assessed value is not within one or more ranges of values associated with one or more respiration parameters the performance indicator 116 may instruct the subject to achieve one or more respiration parameters that are within one or more ranges of levels. In another example, a timer 134 may assess a period of time that a subject inhales through an inhaler. The timer 134 may transmit one or more signals 112 that include the assessed value to a performance indicator 116. If the assessed time period value is outside the one or more ranges the performance indicator 116 may instruct the subject to inhale through the inhaler for a time period that is within the one or more ranges. In some embodiments, a sensor 114 may assess one or more respiration parameters associated with use of an inhaler by a subject and then transmit one or more signals 112 that include the information to a control unit 108. The control unit 108 may then direct a performance indicator 116 to instruct the subject to achieve one or more levels that are within one or more ranges of levels.

In some embodiments, operation 1240 includes instructing the subject to achieve one or more values associated with one or more inhalation parameters that are within one or more ranges of levels associated with the one or more inhalation parameters (not shown). In some embodiments, system 100 may be used to instruct a subject to achieve one or more values associated with one or more inhalation parameters that are within one or more ranges of levels associated with the one or more inhalation parameters. For example, in some embodiments, one or more velocimeters 138 may assess one or more values associated with the velocity of flow through one or more flow channels 104 disposed within an inhaler during an inhalation cycle of a subject using the inhaler. The one or more velocimeters 138 may transmit one or more signals 112 that include the one or more values to a performance indicator 116. The performance indicator 116 may then instruct the subject to achieve one or more values that are within one or more ranges of levels associated with the one or more inhalation parameters. Examples of such instructions may include, but are not limited to, instructing the subject to increase flow though the inhaler, instructing the subject to decrease flow though the inhaler, instructing the subject to maintain the current level of flow though the inhaler, and the like.

In some embodiments, operation 1240 includes instructing the subject to achieve one or more values associated with one or more breath hold parameters that are within one or more ranges of levels associated with the one or more breath hold parameters (not shown). In some embodiments, system 100 may be used to instruct a subject to achieve one or more values associated with one or more breath hold parameters that are within one or more ranges of levels associated with the one or more breath hold parameters. Values related to numerous breath hold parameters may be assessed and used to instruct a subject to achieve one or more values associated with one or more breath hold parameters that are within one or more ranges of levels associated with the one or more breath hold parameters. Examples of such breath hold parameters include, but are not limited to, a time period associated with a breath hold cycle, inhalation volume associated with a breath hold cycle, a quantity of formulation 214 that is inhaled and held during a breath hold cycle, a quantity of an incentive agent 218 that is inhaled and held during a breath hold cycle, and the like. In some embodiments, a timer 134 may assess one or more time periods associated with a breath hold cycle. The timer 134 may transmit one or more signals 112 that include the one or more assessed values to a performance indicator 116 that instructs the subject to achieve one or more values associated with one or more breath hold periods that are within a range of levels associated with the one or more breath hold periods. In some embodiments, a performance indicator 116 may instruct the subject to increase the volume of flow that is inhaled and held during a breath hold cycle. In some embodiments, a performance indicator 116 may instruct the subject to decrease the volume of flow that is inhaled and held during a breath hold cycle. In some embodiments, a sensor 114 may transmit one or more signals 112 that include an assessed value to a control unit 108 that directs a performance indicator 116 to instruct the subject to achieve one or more values associated with one or more breath hold parameters that are within a range of levels associated with the one or more breath hold parameters.

In some embodiments, operation 1240 includes instructing the subject to achieve one or more values associated with one or more exhalation parameters that are within one or more ranges of levels associated with the one or more exhalation parameters (not shown). In some embodiments, system 100 may be used to instruct a subject to achieve one or more values associated with one or more exhalation parameters that are within one or more ranges of levels associated with the one or more exhalation parameters. For example, in some embodiments, one or more velocimeters 138 may assess one or more values associated with the velocity of flow through one or more flow channels 104 disposed within an inhaler during an exhalation cycle of a subject using the inhaler. The one or more velocimeters 138 may transmit one or more signals 112 that include the one or more values to a performance indicator 116 that instructs the subject to achieve one or more values associated with one or more exhalation parameters that are within one or more ranges of levels associated with the one or more exhalation parameters. Examples of such instructions may include, but are not limited to, instructing the subject to increase flow though the inhaler, instructing the subject to decrease flow though the inhaler, instructing the subject to maintain the current level of flow though the inhaler, and the like.

Figure 13:
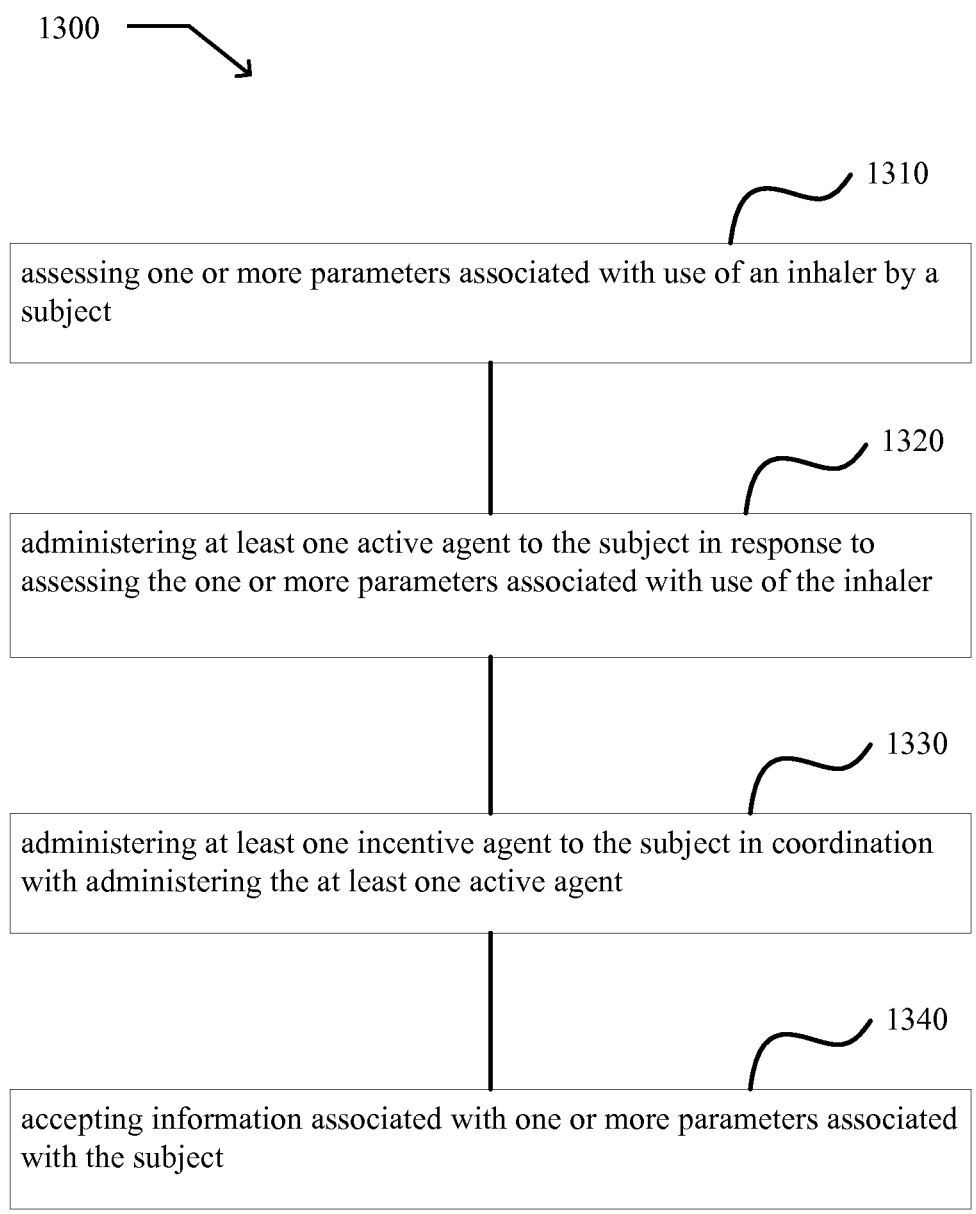
FIG. 13 illustrates an example operational flow 1300 in which embodiments may be implemented.

FIG. 13 illustrates operational flow 1300 that includes operation 1310 that includes assessing one or more parameters associated with use of an inhaler by a subject, operation 1320 that includes administering at least one active agent 214 to the subject in response to assessing the one or more parameters associated with use of the inhaler, operation 1330 that includes administering at least one incentive agent 218 to the subject in coordination with administering the at least one active agent 214, and operation 1340 that includes accepting information associated with one or more parameters associated with the subject. Operations 1310, 1320, and 1330 correspond to operations 1010, 1020, and 1030 as previously described with reference to FIG. 10.

In FIG. 13 and in the following description that includes various examples of operations used during performance of the method, discussion and explanation may be provided with respect to any one or combination of the above-described examples, and/or with respect to other examples and contexts. However, it should be understood that the operations may be executed in a number of other environments and contexts, and/or modified versions of the figures. Also, although the various operations are presented in the sequence(s) illustrated, it should be understood that the various operations may be performed in other orders than those which are illustrated, or may be performed concurrently.

Operation 1340 includes accepting information associated with one or more parameters associated with the subject. In some embodiments, system 100 may be used to accept information associated with one or more parameters associated with a subject. For example, in some embodiments, a user interface 110 may accept information associated with one or more parameters associated with a subject. In some embodiments, a control unit 108 may accept information associated with one or more parameters associated with a subject. In some embodiments, a performance indicator 116 may accept information associated with one or more parameters associated with a subject. Accordingly, numerous components of system 100 may accept information associated with one or more parameters associated with a subject. Numerous types of information associated with one or more parameters associated with a subject may be accepted. Examples of such information include, but are not limited to, height, weight, age, activity level, drug use, nutraceutical use, heart rate, tidal volume, dosage of a drug used by the subject, and the like.

In some embodiments, operation 1340 includes accepting information associated with one or more physical parameters associated with the subject (not shown). In some embodiments, system 100 may be used to accept information associated with one or more physical parameters associated with a subject. For example, in some embodiments, a user interface 110 may accept information associated with one or more physical parameters associated with a subject. In some embodiments, a control unit 108 may accept information associated with one or more physical parameters associated with a subject. In some embodiments, a performance indicator 116 may accept information associated with one or more physical parameters associated with a subject. Accordingly, numerous components of system 100 may accept information associated with one or more physical parameters associated with a subject. Numerous types of information associated with one or more physical parameters associated with a subject may be accepted. Examples of such information include, but are not limited to, height, weight, age, activity level, heart rate, tidal volume, and the like.

In some embodiments, operation 1340 includes accepting information associated with one or more parameters associated with the subject and using the information in combination with one or more respiration parameters to determine one or more subject specific respiration characteristics (not shown). In some embodiments, system 100 may be used to accept information associated with one or more parameters associated with a subject and use the information in combination with one or more respiration parameters to determine one or more subject specific respiration characteristics. In some embodiments, a control unit 108 may accept information associated with one or more parameters associated with a subject and use the information in combination with one or more respiration parameters to determine one or more subject specific respiration characteristics associated with the subject. For example, in some embodiments, a control unit 108 may accept information associated with the total lung capacity associated with a subject. The control unit 108 may also receive one or more signals 112 that include one or more assessed values associated with the tidal volume of the subject from one or more sensors 114 associated with an inhaler used by the subject. The control unit 108 may then use the total lung capacity and the tidal volume to calculate the residual volume that is specific to the subject. Accordingly, numerous subject specific respiration characteristics may be determined. Examples of such subject specific respiration characteristics include, but are not limited to, total lung capacity, tidal volume, residual volume, expiratory reserve volume, inspiratory reserve volume, inspiratory capacity, inspiratory vital capacity, vital capacity, function residual volume, alveolar gas volume, actual volume of the lung, forced vital capacity, forced expiratory volume, forced expiratory flow, forced inspiratory flow, peak expiratory flow, maximal voluntary ventilation, and the like.

In some embodiments, operation 1340 includes accepting information associated with one or more parameters associated with the subject and using the information in combination with one or more delivery parameters to estimate a quantity of the active agent 214 that will be effectively delivered to the subject (not shown). In some embodiments, system 100 may be used to accept information associated with one or more parameters associated with a subject and use the information in combination with one or more delivery parameters to estimate a quantity of an active agent 214 that will be effectively delivered to the subject. For example, in some embodiments, a control unit 108 may accept information associated with the total lung capacity of a subject. The control unit 108 may also receive one or more signals that include information associated with a total volume of flow and quantity of active agent 214 that flowed through one or more flow channels 104 in an inhaler used by the subject during an inhalation cycle from one or more sensors 114. The control unit 108 may then estimate a quantity of active agent 214 that was effectively delivered to the subject based on the inhaled volume and the quantity of the active agent 214 that was delivered.

Figure 14:
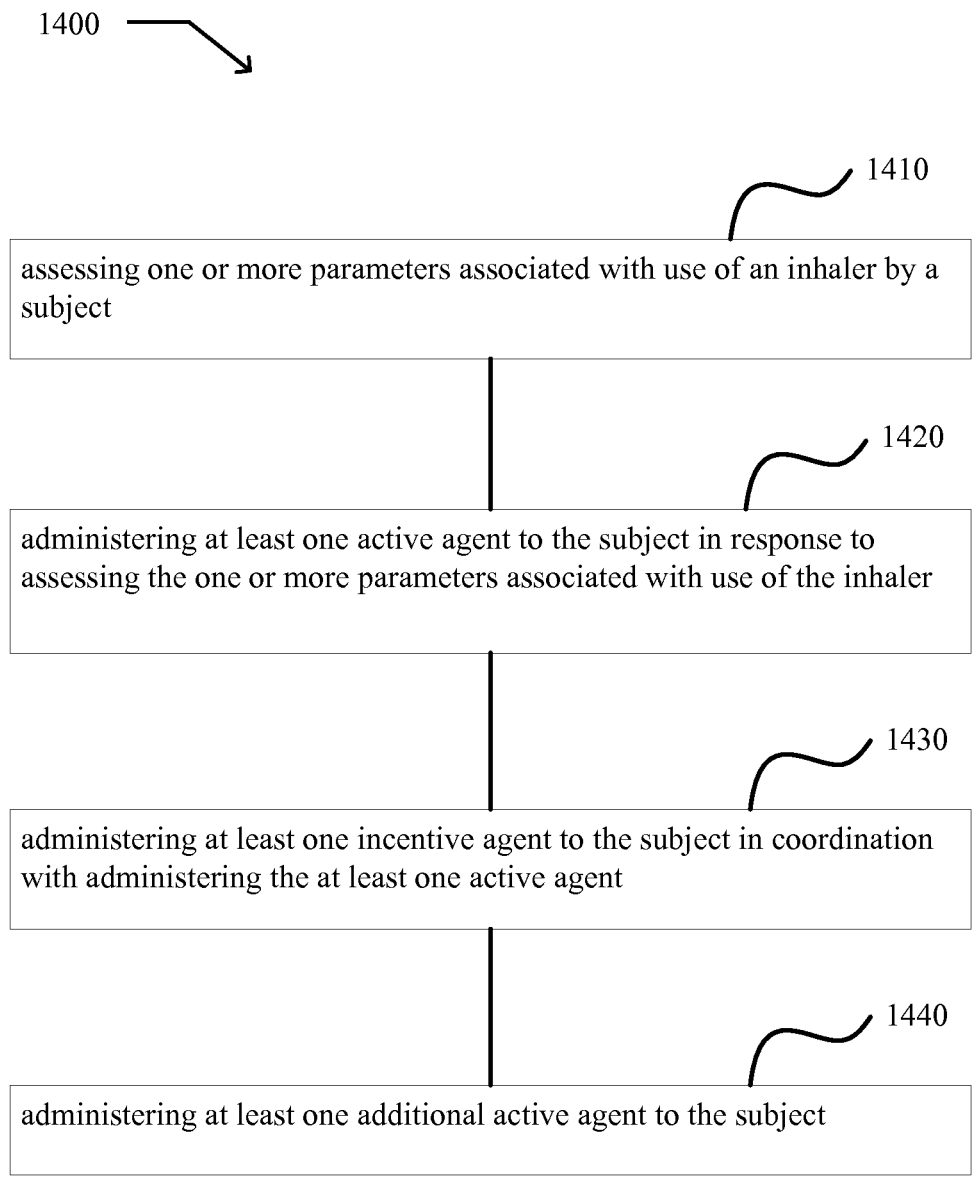
FIG. 14 illustrates an example operational flow 1400 in which embodiments may be implemented.

FIG. 14 illustrates operational flow 1400 that includes operation 1410 that includes assessing one or more parameters associated with use of an inhaler by a subject, operation 1420 that includes administering at least one active agent 214 to the subject in response to assessing the one or more parameters associated with use of the inhaler, operation 1430 that includes administering at least one incentive agent 218 to the subject in coordination with administering the at least one active agent 214, and operation 1440 that includes administering at least one additional active agent 214 to the subject. Operations 1410, 1420, and 1430 correspond to operations 1010, 1020, and 1030 as previously described with reference to FIG. 10.

In FIG. 14 and in the following description that includes various examples of operations used during performance of the method, discussion and explanation may be provided with respect to any one or combination of the above-described examples, and/or with respect to other examples and contexts. However, it should be understood that the operations may be executed in a number of other environments and contexts, and/or modified versions of the figures. Also, although the various operations are presented in the sequence(s) illustrated, it should be understood that the various operations may be performed in other orders than those which are illustrated, or may be performed concurrently.

Operation 1440 includes administering at least one additional active agent 214 to the subject. In some embodiments, system 100 may be used to administer at least one additional active agent 214 to a subject. For example, in some embodiments, a control unit 108 may direct one or more actuators 120 to facilitate at least partial release of at least one additional active agent 214 from one or more active agent reservoirs 212. Numerous types of active agents 214 may be administered. Examples of such active agents 214 include, but are not limited to, steroids, anti-inflammatory drugs, bronchodilators, leukotriene modifiers, long-acting beta antagonists, 1,3-dimethylxanthine, short-acting beta agonists, [8-methyl-8-(1-methylethyl)-8-azoniabicyclo[3.2.1]oct-3-yl]3-hydroxy-2-phenyl-propanoate, antibodies, and the like (see e.g., *Remingtion: The Science and Practice of Pharmacy*, Lippincott, Williams & Wilkins, 20th edition, Baltimore, Md., USA (2000), *Physicians' Desk Reference*, Thomson PDR, 58th edition, Montvale, N.J. (2004); *Merck Index*, Merck and Co., 13th edition, Whitehouse Station, N.J. (2001); which are hereby incorporated by reference). Accordingly, numerous combinations of active agents 214 may be administered to a subject.

In some embodiments, operation 1440 includes administering at least one pulmonary vasodilator (not shown). In some embodiments, system 100 may be used to administer at least one pulmonary vasodilator. For example, in some embodiments, a control unit 108 may direct one or more actuators 120 to facilitate at least partial release of one or more pulmonary vasodilators from one or more active agent reservoirs 212. Examples of pulmonary vasodilators include, but are not limited to, endothelin receptor antagonists, phosphodiesterase type 5 (PDE-5) inhibitors, prostacyclin derivatives, and 5-{(E)-(1S,5S,6R,7R)-7-hydroxy-6[(E)-(3S,4RS)-3-hydroxy-4-methyl-1-octen-6-inyl]-bicyclo[3.3.0]octan-3-ylidene}pentanoic acid.

In some embodiments, operation 1440 includes administering at least one anti-inflammatory agent (not shown). In some embodiments, system 100 may be used to administer at least one anti-inflammatory agent. For example, in some embodiments, a control unit 108 may direct one or more actuators 120 to facilitate at least partial release of one or more anti-inflammatory agents from one or more active agent reservoirs 212. Examples of anti-inflammatory agents include, but are not limited to, beclomethasone dipropionate, fluticasione propionate, flunisolide, budesonide, mometasone, ciclesonide, cromolyn sodium, and nedocromil sodium.

Figure 15:
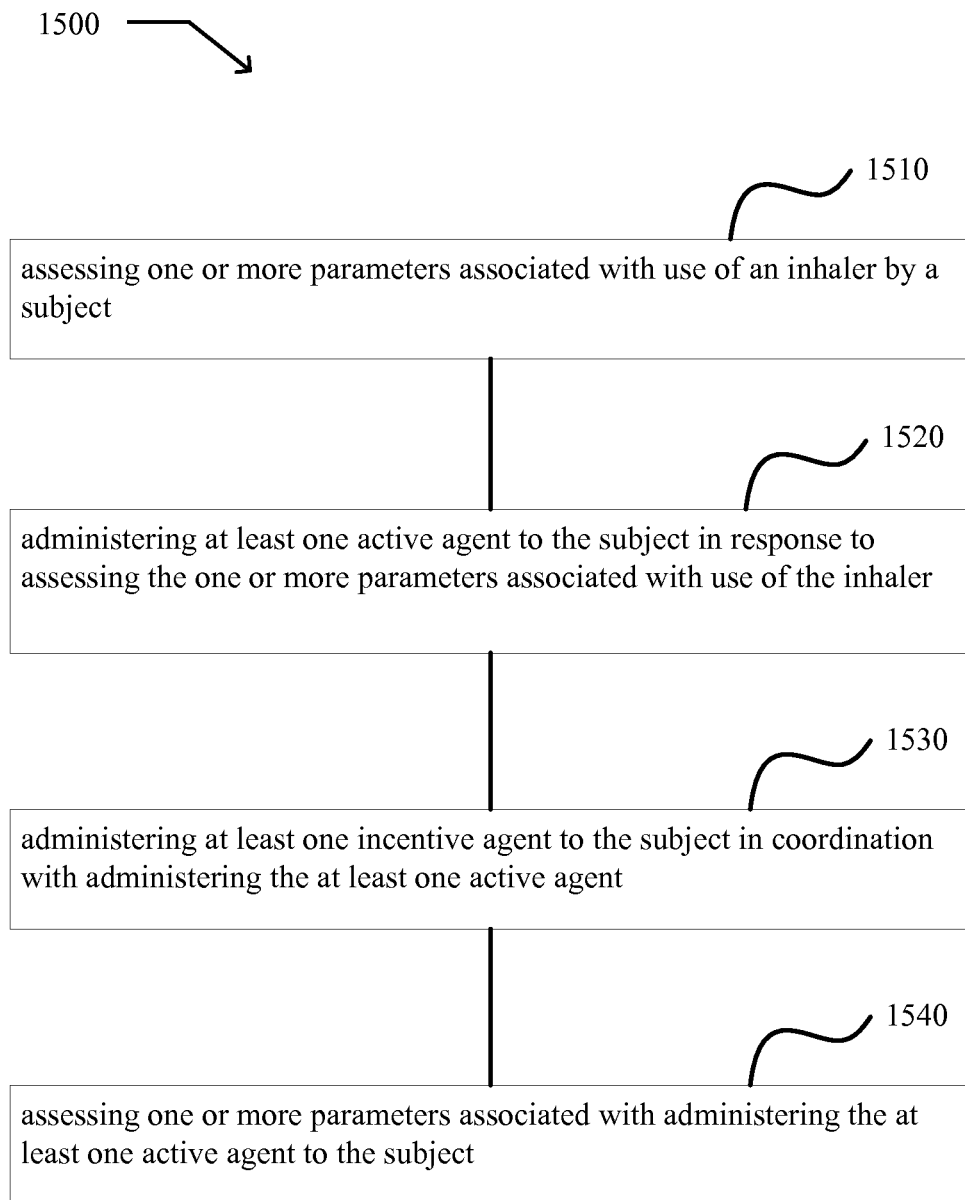
FIG. 15 illustrates an example operational flow 1500 in which embodiments may be implemented.

FIG. 15 illustrates operational flow 1500 that includes operation 1510 that includes assessing one or more parameters associated with use of an inhaler by a subject, operation 1520 that includes administering at least one active agent 214 to the subject in response to assessing the one or more parameters associated with use of the inhaler, operation 1530 that includes administering at least one incentive agent 218 to the subject in coordination with administering the at least one active agent 214, and operation 1540 that includes assessing one or more parameters associated with administering the at least one active agent 214 to the subject. Operations 1510, 1520, and 1530 correspond to operations 1010, 1020, and 1030 as previously described with reference to FIG. 10.

In FIG. 15 and in the following description that includes various examples of operations used during performance of the method, discussion and explanation may be provided with respect to any one or combination of the above-described examples, and/or with respect to other examples and contexts. However, it should be understood that the operations may be executed in a number of other environments and contexts, and/or modified versions of the figures. Also, although the various operations are presented in the sequence(s) illustrated, it should be understood that the various operations may be performed in other orders than those which are illustrated, or may be performed concurrently.

Operation 1540 includes assessing one or more parameters associated with administering the at least one active agent 214 to the subject. In some embodiments, system 100 may be used to assess one or more parameters associated with administering at least one active agent 214 to the subject. For example, in some embodiments, an optical sensor 126 may be used to assess a quantity of one or more active agents 214 that flow through one or more flow channels 104 that are disposed within an inhaler during use of the inhaler by a subject. In some embodiments, a velocimeter 138 may be used to assess the velocity with which one or more active agents 214 flow through one or more flow channels 104 that are disposed within an inhaler during use of the inhaler by a subject. Accordingly, numerous parameters may be determined that are associated with administration of one or more active agents 214 to a subject.

In some embodiments, operation 1540 includes assessing one or more parameters associated with a velocity with which the at least one active agent 214 was administered to the subject (not shown). In some embodiments, system 100 may be used to assess one or more parameters associated with a velocity with which at least one active agent 214 was administered to a subject. For example, in some embodiments, a velocimeter 138 may be used to assess the velocity with which one or more active agents 214 flow through one or more flow channels 104 that are disposed within an inhaler during use of the inhaler by a subject.

In some embodiments, operation 1540 includes assessing one or more parameters associated with a volume of gas in which the at least one active agent 214 was administered to the subject (not shown). In some embodiments, system 100 may be used to assess one or more parameters associated with a volume of gas in which at least one active agent 214 was administered to a subject. For example, in some embodiments, a volume sensor 128 may be used to assess a volume of gas in which one or more active agents 214 flow through one or more flow channels 104 disposed within an inhaler when the inhaler is used by a subject.

In some embodiments, operation 1540 includes assessing a time period associated with administering the at least one active agent 214 to the subject (not shown). In some embodiments, system 100 may be used to assess a time period associated with administering at least one active agent 214 to a subject. For example, in some embodiments, a timer 134 may be used to assess a time period in which one or more active agents 214 are administered through one or more flow channels 104 disposed within an inhaler when the inhaler is used by a subject.

In some embodiments, operation 1540 includes assessing a quantity of the at least one active agent 214 that was administered to the subject (not shown). In some embodiments, system 100 may be used to assess a quantity of at least one active agent 214 that was administered to a subject. In some embodiments, an optical sensor 126 may be used to assess a quantity of one or more active agents 214 that flow through one or more flow channels 104 disposed within an inhaler that is used by a subject. In some embodiments, a phase Doppler interferometer 136 may be used to assess a quantity of one or more active agents 214 that flow through one or more flow channels 104 disposed within an inhaler that is used by a subject. In some embodiments, an ultrasonic flow meter 140 may be used to assess a quantity of one or more active agents 214 that flow through one or more flow channels 104 disposed within an inhaler that is used by a subject. In some embodiments, a sensor 114 may transmit one or more signals 112 that include one or more assessed values associated with a quantity of one or more active agents 214 to a control unit 108 that receives the one or more assessed values and then determines a quantity of one or more active agents 214 that were delivered to a subject using an inhaler.

In some embodiments, operation 1540 includes assessing a quantity of the at least one active agent 214 that was administered to the subject and then repeating the administration of the at least one active agent 214 until a preselected quantity of the at least one active agent 214 is administered to the subject (not shown). In some embodiments, system 100 may be used to assess a quantity of at least one active agent 214 that was administered to a subject and then repeat administration of the at least one active agent 214 until a preselected quantity of the at least one active agent 214 is administered to the subject. In some embodiments, an optical sensor 126 may be used to assess a quantity of one or more active agents 214 that flow through one or more flow channels 104 disposed within an inhaler that is used by a subject. In some embodiments, a phase Doppler interferometer 136 may be used to assess a quantity of one or more active agents 214 that flow through one or more flow channels 106 disposed within an inhaler that is used by a subject. In some embodiments, an ultrasonic flow meter 140 may be used to assess a quantity of one or more active agents 214 that flow through one or more flow channels 104 disposed within an inhaler that is used by a subject. In some embodiments, a sensor 114 may transmit one or more signals 112 that include one or more assessed values associated with a quantity of one or more active agents 214 to a control unit 108 that receives the one or more assessed values and then determines a quantity of one or more active agents 214 that were delivered to a subject using the inhaler. The control unit 108 may then assess the quantity of one or more active agents 214 that were delivered to a subject using the inhaler and determine an additional quantity of the one or more active agents 214 that are to be delivered to the subject to reach a preselected quantity of the one or more active agents 214 for delivery. The control unit 108 may then direct one or more actuators 120 to facilitate at least partial release of one or more active agents 214 from one or more active agent reservoirs 212 until the preselected quantity of the one or more active agents 214 are administered to the subject.

Figure 16:
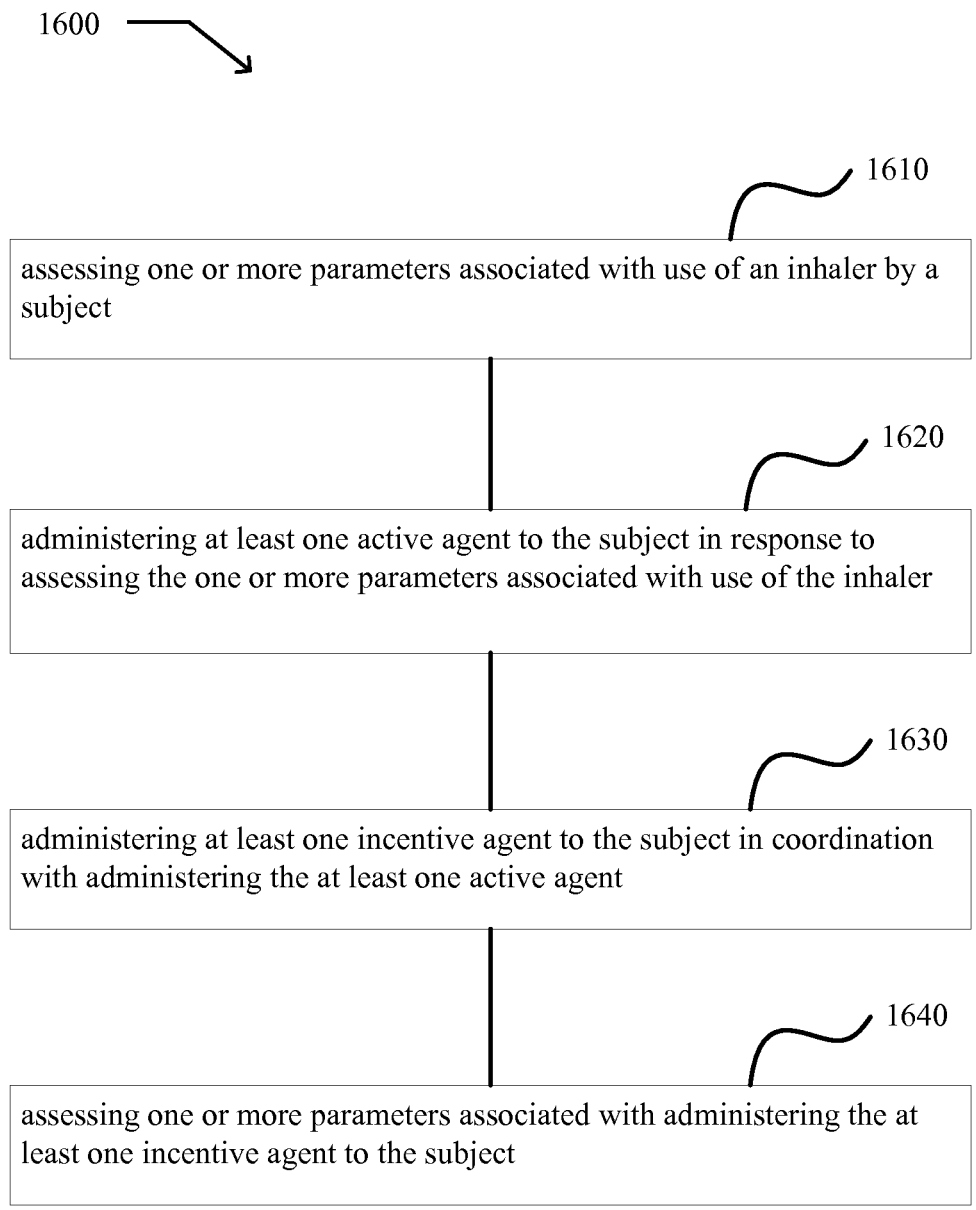
FIG. 16 illustrates an example operational flow 1600 in which embodiments may be implemented.

FIG. 16 illustrates operational flow 1600 that includes operation 1610 that includes assessing one or more parameters associated with use of an inhaler by a subject, operation 1620 that includes administering at least one active agent 214 to the subject in response to assessing the one or more parameters associated with use of the inhaler, operation 1630 that includes administering at least one incentive agent 218 to the subject in coordination with administering the at least one active agent 214, and operation 1640 that includes assessing one or more parameters associated with administering the at least one incentive agent 218 to the subject. Operations 1610, 1620, and 1630 correspond to operations 1010, 1020, and 1030 as previously described with reference to FIG. 10.

In FIG. 16 and in the following description that includes various examples of operations used during performance of the method, discussion and explanation may be provided with respect to any one or combination of the above-described examples, and/or with respect to other examples and contexts. However, it should be understood that the operations may be executed in a number of other environments and contexts, and/or modified versions of the figures. Also, although the various operations are presented in the sequence(s) illustrated, it should be understood that the various operations may be performed in other orders than those which are illustrated, or may be performed concurrently.

Operation 1640 includes assessing one or more parameters associated with administering the at least one incentive agent 218 to the subject. In some embodiments, system 100 may be used to assess one or more parameters associated with administering at least one incentive agent 218 to the subject. For example, in some embodiments, an optical sensor 126 may be used to assess a quantity of one or more incentive agents 218 that flow through one or more flow channels 104 that are disposed within an inhaler during use of the inhaler by a subject. In some embodiments, a velocimeter 138 may be used to assess the velocity with which one or more incentive agents 218 flow through one or more flow channels 104 that are disposed within an inhaler during use of the inhaler by a subject. Accordingly, numerous parameters may be determined that are associated with administration of one or more incentive agents 218 to a subject.

In some embodiments, operation 1640 includes assessing one or more parameters associated with a velocity with which the at least one incentive agent 218 was administered to the subject (not shown). In some embodiments, system 100 may be used to assess one or more parameters associated with a velocity with which at least one incentive agent 218 was administered to a subject. For example, in some embodiments, a velocimeter 138 may be used to assess the velocity with which one or more incentive agents 218 flow through one or more flow channels 104 that are disposed within an inhaler during use of the inhaler by a subject.

In some embodiments, operation 1640 includes assessing one or more parameters associated with a volume of gas in which the at least one incentive agent 218 was administered to the subject (not shown). In some embodiments, system 100 may be used to assess one or more parameters associated with a volume of gas in which at least one incentive agent 218 was administered to a subject. For example, in some embodiments, a volume sensor 128 may be used to assess a volume of gas in which one or more incentive agents 218 flow through one or more flow channels 104 disposed within an inhaler when the inhaler is used by a subject.

In some embodiments, operation 1640 includes assessing a time period associated with administering the at least one incentive agent 218 to the subject (not shown). In some embodiments, system 100 may be used to assess a time period associated with administering at least one incentive agent 218 to a subject. For example, in some embodiments, a timer 134 may be used to assess a time period in which one or more incentive agents 218 are administered through one or more flow channels 104 disposed within an inhaler when the inhaler is used by a subject.

In some embodiments, operation 1640 includes assessing a quantity of the at least one incentive agent 218 that was administered to the subject (not shown). In some embodiments, system 100 may be used to assess a quantity of at least one incentive agent 218 that was administered to a subject. In some embodiments, an optical sensor 126 may be used to assess a quantity of one or more incentive agents 218 that flow through one or more flow channels 104 disposed within an inhaler that is used by a subject. In some embodiments, a phase Doppler interferometer 136 may be used to assess a quantity of one or more incentive agents 218 that flow through one or more flow channels 104 disposed within an inhaler that is used by a subject. In some embodiments, an ultrasonic flow meter 140 may be used to assess a quantity of one or more incentive agents 218 that flow through one or more flow channels 104 disposed within an inhaler that is used by a subject. In some embodiments, a sensor 114 may transmit one or more signals 112 that include one or more assessed values associated with a quantity of one or more incentive agents 218 to a control unit 108 that receives the one or more assessed values and then determines a quantity of one or more incentive agents 218 that were delivered to a subject using an inhaler.

In some embodiments, operation 1640 includes assessing a quantity of the at least one incentive agent 218 that was administered to the subject and then repeating the administration of the at least one incentive agent 218 until a preselected quantity of the at least one active agent 214 is administered to the subject (not shown). In some embodiments, system 100 may be used to assess a quantity of at least one incentive agent 218 that was administered to a subject and then repeat administration of the at least one incentive agent 218 until a preselected quantity of the at least one incentive agent 218 is administered to the subject. In some embodiments, an optical sensor 126 may be used to assess a quantity of one or more incentive agents 218 that flow through one or more flow channels 104 disposed within an inhaler that is used by a subject. In some embodiments, a phase Doppler interferometer 136 may be used to assess a quantity of one or more incentive agents 218 that flow through one or more flow channels 106 disposed within an inhaler that is used by a subject. In some embodiments, an ultrasonic flow meter 140 may be used to assess a quantity of one or more incentive agents 218 that flow through one or more flow channels 104 disposed within an inhaler that is used by a subject. In some embodiments, a sensor 114 may transmit one or more signals 112 that include one or more assessed values associated with a quantity of one or more incentive agents 218 to a control unit 108 that receives the one or more assessed values and then determines a quantity of one or more incentive agents 218 that were delivered to a subject using the inhaler. The control unit 108 may then assess the quantity of one or more incentive agents 218 that were delivered to a subject using the inhaler and determine an additional quantity of the one or more incentive agents 218 that are to be delivered to the subject to reach a preselected quantity of the one or more incentive agents 218 for delivery. The control unit 108 may then direct one or more actuators 120 to facilitate at least partial release of one or more incentive agents 218 from one or more incentive agent reservoirs 216 until the preselected quantity of the one or more incentive agents 218 are administered to the subject.

Figure 17:
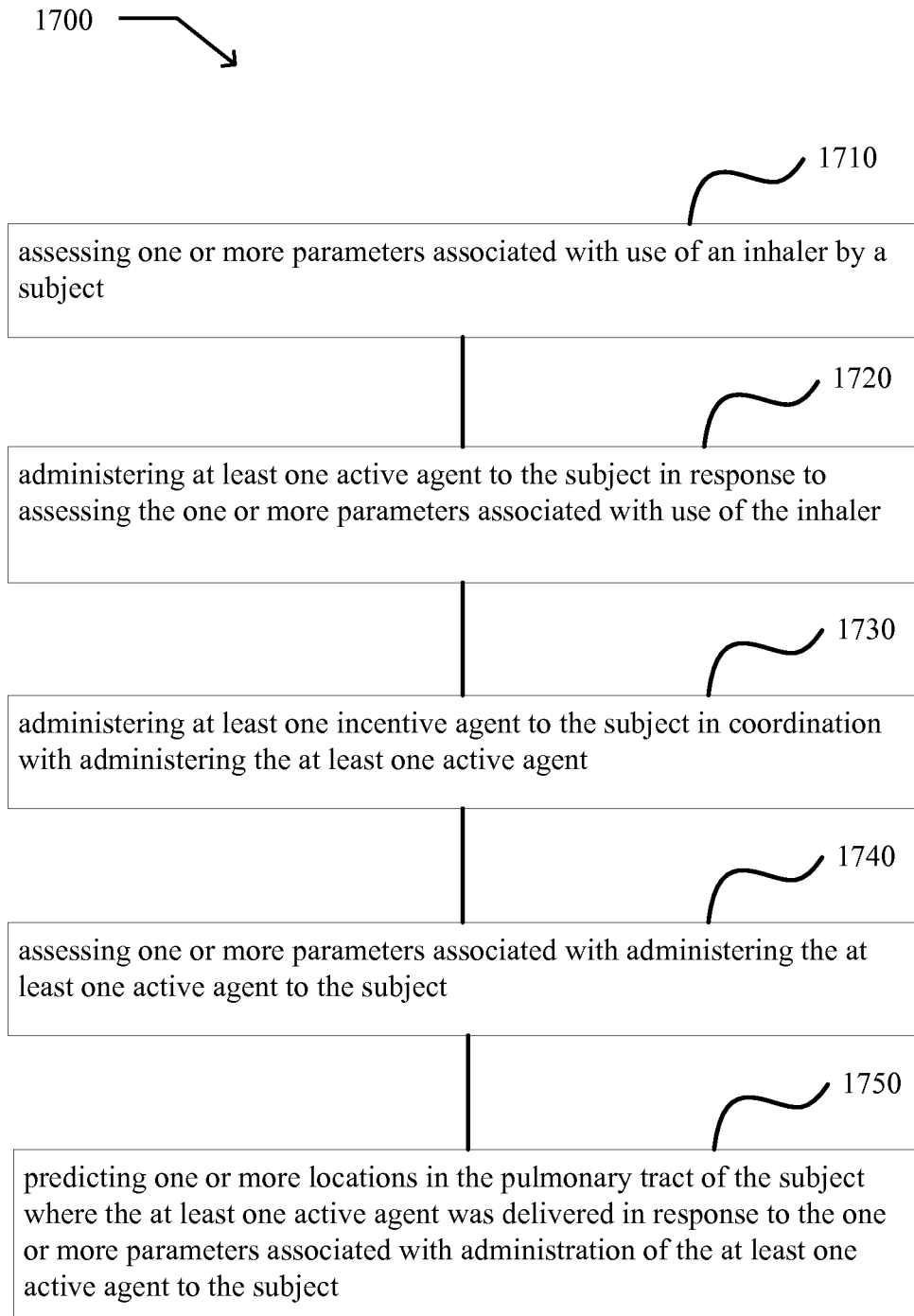
FIG. 17 illustrates an example operational flow 1700 in which embodiments may be implemented.

FIG. 17 illustrates operational flow 1700 that includes operation 1710 that includes assessing one or more parameters associated with use of an inhaler by a subject, operation 1720 that includes administering at least one active agent 214 to the subject in response to assessing the one or more parameters associated with use of the inhaler, operation 1730 that includes administering at least one incentive agent 218 to the subject in coordination with administering the at least one active agent 214, operation 1740 that includes assessing one or more parameters associated with administering the at least one active agent 214 to the subject, and operation 1750 that includes predicting one or more locations in the pulmonary tract of the subject where the at least one active agent 214 was delivered in response to the one or more parameters associated with administration of the at least one active agent 214 to the subject. Operations 1710, 1720, and 1730 correspond to operations 1010, 1020, and 1030 as previously described with reference to FIG. 10 and operation 1740 corresponds to operation 1540 as previously described with reference to FIG. 15.

In FIG. 17 and in the following description that includes various examples of operations used during performance of the method, discussion and explanation may be provided with respect to any one or combination of the above-described examples, and/or with respect to other examples and contexts. However, it should be understood that the operations may be executed in a number of other environments and contexts, and/or modified versions of the figures. Also, although the various operations are presented in the sequence(s) illustrated, it should be understood that the various operations may be performed in other orders than those which are illustrated, or may be performed concurrently.

Operation 1750 includes predicting one or more locations in the pulmonary tract of the subject where the at least one active agent 214 was delivered in response to the one or more parameters associated with administration of the at least one active agent 214 to the subject. In some embodiments, system 100 may be used to predict one or more locations in the pulmonary tract of a subject where at least one active agent 214 was delivered in response to one or more parameters associated with administration of the at least one active agent 214 to the subject. For example, in some embodiments, a flow sensor 124 may be used to measure a volume of flow through one or more flow channels 104 disposed within an inhaler during an inhalation cycle by a subject using the inhaler to administer one or more active agents 214. The flow sensor 124 may transmit one or more signals that include an assessed value for the volume of flow through the inhaler to a control unit 108. The control unit 108 may then compare the assessed volume of flow to the total lung capacity of the subject using the inhaler. The control unit 108 may then predict one or more locations in the pulmonary tract of the subject where the at least one active agent 214 was delivered based on the comparison of assessed volume of flow to total lung capacity of the subject. For example, if the assessed volume of flow is nearly equal to the total lung capacity of the subject, the control unit 108 may predict that the active agent 214 was administered to deep lung tissue. In contrast, if the assessed volume of flow is a small fraction of the total lung capacity of the subject, the control unit 108 may predict that the active agent 214 was administered to shallow lung tissue.

In some embodiments, operation 1750 includes predicting a quantity of the at least one active agent 214 delivered to one or more locations in the pulmonary tract of the subject and then repeating the administration of the at least one active agent 214 until a preselected quantity of the at least one active agent 214 is predicted to have been administered to the subject (not shown). In some embodiments, system 100 may be used to predict a quantity of at least one active agent 214 delivered to one or more locations in the pulmonary tract of a subject and then repeat administration of the at least one active agent 214 until a preselected quantity of the at least one active agent 214 is predicted to have been administered to the subject. For example, in some embodiments, sensors 114 may be used to assess a volume of flow and a quantity of one or more active agents 214 flowing through one or more flow channels 104 disposed within an inhaler during an inhalation cycle by a subject using the inhaler to administer the one or more active agents 214. The sensors 114 may transmit one or more signals 112 that include one or more assessed values corresponding to the volume of flow and the quantity of active agent 214 flowing through the inhaler to a control unit 108. The control unit 108 may then compare the assessed volume of flow to the total lung capacity of the subject using the inhaler. The control unit 108 may then predict one or more locations in the pulmonary tract of the subject where the one or more active agents 214 were delivered based on the comparison of assessed volume of flow to total lung capacity of the subject. The control unit 108 may also predict the quantity of the one or more active agents 214 that were delivered to the location in the pulmonary tract based on the assessed quantity of the one or more active agents 214. For example, if the assessed volume of flow is a small fraction of the total lung capacity of the subject, the control unit 108 may predict that the assessed quantity of the one or more active agents 214 were administered to shallow lung tissue. In contrast, if the assessed volume of flow is nearly equal to the total lung capacity of the subject, the control unit 108 may predict that the assessed quantity of the one or more active agents 214 were administered throughout the pulmonary tract. The control unit 108 may then compare the quantity of the one or more active agents 214 that were administered to the subject to a preselected quantity of the one or more active agents 214 that are to be administered to the subject to determine an additional quantity of one or more active agents 214 for administration to the subject. The control unit 108 may then direct one or more actuators 120 to facilitate at least partial release from one or more active agent reservoirs 212 to administer the one or more active agents 214 to the subject until a preselected quantity of the one or more active agents 214 have been administered to the subject. In some embodiments, a control unit 108 may direct one or more actuators 120 to facilitate at least partial release from one or more active agent reservoirs 122 at selected stages of an inhalation cycle through an inhaler by a subject. For example, in some embodiments, a control unit 108 may direct one or more actuators 120 to facilitate at least partial release from one or more active agent reservoirs 212 during an early stage of an inhalation cycle to administer one or more active agents 214 to deep lung tissue in the pulmonary tract. In some embodiments, a control unit 108 may direct one or more actuators 120 to facilitate at least partial release from one or more active agent reservoirs 212 during a late stage of an inhalation cycle to administer one or more active agents 214 to shallow lung tissue in the pulmonary tract. Accordingly, in some embodiments, the quantity of one or more active agents 214 and the location in the pulmonary tract to which the one or more active agents 214 are administered may be controlled.

Figure 18:
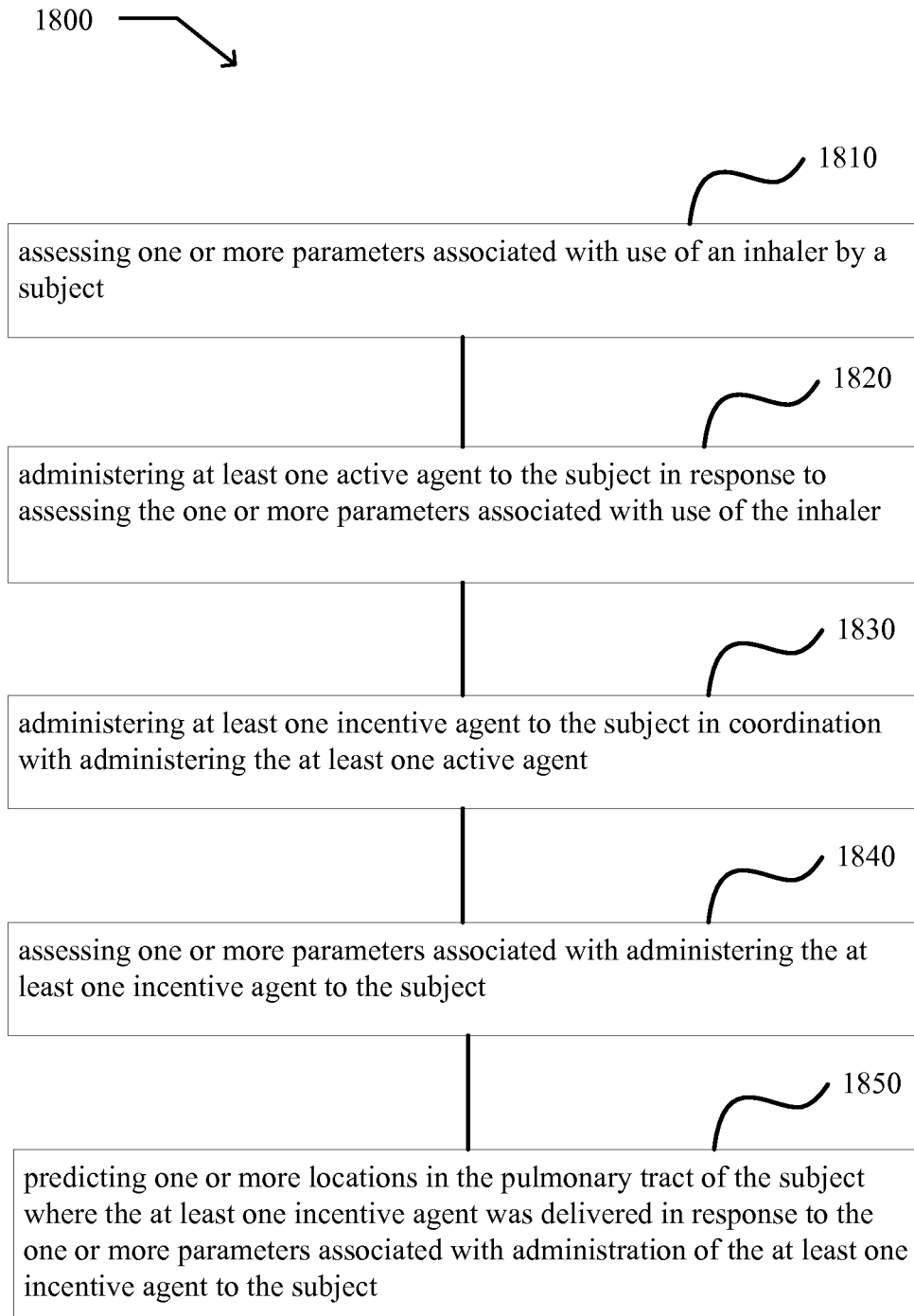
FIG. 18 illustrates an example operational flow 1800 in which embodiments may be implemented.

FIG. 18 illustrates operational flow 1800 that includes operation 1810 that includes assessing one or more parameters associated with use of an inhaler by a subject, operation 1820 that includes administering at least one active agent 214 to the subject in response to assessing the one or more parameters associated with use of the inhaler, operation 1830 that includes administering at least one incentive agent 218 to the subject in coordination with administering the at least one active agent 214, operation 1840 that includes assessing one or more parameters associated with administering the at least one active agent 214 to the subject, and operation 1850 that includes predicting one or more locations in the pulmonary tract of the subject where the at least one active agent 214 was delivered in response to the one or more parameters associated with administration of the at least one active agent 214 to the subject. Operations 1810, 1820, and 1830 correspond to operations 1010, 1020, and 1030 as previously described with reference to FIG. 10 and operation 1840 corresponds to operation 1640 as previously described with reference to FIG. 16.

In FIG. 18 and in the following description that includes various examples of operations used during performance of the method, discussion and explanation may be provided with respect to any one or combination of the above-described examples, and/or with respect to other examples and contexts. However, it should be understood that the operations may be executed in a number of other environments and contexts, and/or modified versions of the figures. Also, although the various operations are presented in the sequence(s) illustrated, it should be understood that the various operations may be performed in other orders than those which are illustrated, or may be performed concurrently.

Operation 1850 includes predicting one or more locations in the pulmonary tract of the subject where the at least one incentive agent 218 was delivered in response to the one or more parameters associated with administration of the at least one incentive agent 218 to the subject. In some embodiments, system 100 may be used to predict one or more locations in the pulmonary tract of a subject where at least one incentive agent 218 was delivered in response to one or more parameters associated with administration of the at least one incentive agent 218 to the subject. For example, in some embodiments, a flow sensor 124 may be used to measure a volume of flow through one or more flow channels 104 disposed within an inhaler during an inhalation cycle by a subject using the inhaler to administer one or more incentive agents 218. The flow sensor 124 may transmit one or more signals that include an assessed value for the volume of flow through the inhaler to a control unit 108. The control unit 108 may then compare the assessed volume of flow to the total lung capacity of the subject using the inhaler. The control unit 108 may then predict one or more locations in the pulmonary tract of the subject where the at least one incentive agent 218 was delivered based on the comparison of assessed volume of flow to total lung capacity of the subject. For example, if the assessed volume of flow is nearly equal to the total lung capacity of the subject, the control unit 108 may predict that the incentive agent 218 was administered to deep lung tissue. In contrast, if the assessed volume of flow is a small fraction of the total lung capacity of the subject, the control unit 108 may predict that the incentive agent 218 was administered to shallow lung tissue.

In some embodiments, operation 1850 includes predicting a quantity of the at least one incentive agent 218 delivered to one or more locations in the pulmonary tract of the subject and then repeating the administration of the at least one incentive agent 218 until a preselected quantity of the at least one incentive agent 218 is predicted to have been administered to the subject (not shown). In some embodiments, system 100 may be used to predict a quantity of at least one incentive agent 218 delivered to one or more locations in the pulmonary tract of a subject and then repeat administration of the at least one incentive agent 218 until a preselected quantity of the at least incentive agent 218 is predicted to have been administered to the subject. For example, in some embodiments, sensors 114 may be used to assess a volume of flow and a quantity of one or more incentive agents 218 flowing through one or more flow channels 104 disposed within an inhaler during an inhalation cycle by a subject using the inhaler to administer the one or more incentive agents 218. The sensors 114 may transmit one or more signals 112 that include one or more assessed values corresponding to the volume of flow and the quantity of incentive agent 218 flowing through the inhaler to a control unit 108. The control unit 108 may then compare the assessed volume of flow to the total lung capacity of the subject using the inhaler. The control unit 108 may then predict one or more locations in the pulmonary tract of the subject where the one or more incentive agents 218 were delivered based on the comparison of assessed volume of flow to total lung capacity of the subject. The control unit 108 may also predict the quantity of the one or more incentive agents 218 that were delivered to the location in the pulmonary tract based on the assessed quantity of the one or more incentive agents 218. For example, if the assessed volume of flow is a small fraction of the total lung capacity of the subject, the control unit 108 may predict that the assessed quantity of the one or more incentive agents 218 were administered to shallow lung tissue. In contrast, if the assessed volume of flow is nearly equal to the total lung capacity of the subject, the control unit 108 may predict that the assessed quantity of the one or more incentive agents 218 were administered throughout the pulmonary tract. The control unit 108 may then compare the quantity of the one or more incentive agents 218 that were administered to the subject to a preselected quantity of the one or more incentive agents 218 that are to be administered to the subject to determine an additional quantity of one or more incentive agents 218 for administration to the subject. The control unit 108 may then direct one or more actuators 120 to facilitate at least partial release from one or more incentive agent reservoirs 216 to administer the one or more incentive agents 218 to the subject until a preselected quantity of the one or more incentive agents 218 have been administered to the subject. In some embodiments, a control unit 108 may direct one or more actuators 120 to facilitate at least partial release from one or more incentive agent reservoirs 216 at selected stages of an inhalation cycle through an inhaler by a subject. For example, in some embodiments, a control unit 108 may direct one or more actuators 120 to facilitate at least partial release from one or more incentive agent reservoirs 216 during an early stage of an inhalation cycle to administer one or more incentive agents 218 to deep lung tissue in the pulmonary tract. In some embodiments, a control unit 108 may direct one or more actuators 120 to facilitate at least partial release from one or more incentive agent reservoirs 216 during a late stage of an inhalation cycle to administer one or more incentive agents 218 to shallow lung tissue in the pulmonary tract. Accordingly, in some embodiments, the quantity of one or more incentive agents 218 and the location in the pulmonary tract to which the one or more incentive agents 218 are administered may be controlled.

In some embodiments, a system that includes a computer program for executing a computer process on a computing device may be used to control an inhaler. In some embodiments, such a system is provided that includes a non-transitory signal-bearing medium bearing one or more instructions that, when executed by one or more processing components, direct performance of operations that include at least: assessing one or more parameters associated with use of an inhaler by a subject, administering at least one active agent to the subject in response to assessing the one or more parameters associated with use of the inhaler, and administering at least one incentive agent to the subject in coordination with administering the at least one active agent.

In some embodiments, the non-transitory signal-bearing medium may further include one or more instructions that direct performance of an operation that includes at least displaying a comparison of an assessed value associated with one or more respiration parameters with one or more levels associated with the one or more respiration parameters.

In some embodiments, the non-transitory signal-bearing medium may further include one or more instructions that direct performance of an operation that includes at least instructing the subject to achieve one or more values associated with one or more respiration parameters.

In some embodiments, the non-transitory signal-bearing medium may further include one or more instructions that direct performance of an operation that includes at least accepting information associated with one or more parameters associated with the subject.

In some embodiments, the non-transitory signal-bearing medium may further include one or more instructions that direct performance of an operation that includes at least assessing one or more parameters associated with administering the at least one active agent to the subject.

In some embodiments, the non-transitory signal-bearing medium may further include one or more instructions that direct performance of an operation that includes at least assessing one or more parameters associated with administering the at least one incentive agent to the subject.

In some embodiments, the non-transitory signal-bearing medium may further include one or more instructions that direct performance of an operation that includes at least predicting one or more locations in the pulmonary tract of the subject where the at least one active agent was delivered in response to the one or more parameters associated with administration of the at least one active agent to the subject.

In some embodiments, the non-transitory signal-bearing medium may further include one or more instructions that direct performance of an operation that includes at least predicting one or more locations in the pulmonary tract of the subject where the at least one incentive agent was delivered in response to the one or more parameters associated with administration of the at least one incentive agent to the subject.

The one or more instructions may be, for example, computer executable and/or logic-implemented instructions. In some embodiments, the a non-transitory signal-bearing medium may include a computer-readable medium. In some embodiments, the a non-transitory signal-bearing medium may include a recordable medium. In some embodiments, the a non-transitory signal-bearing medium may include a communications medium.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware in one or more machines, compositions of matter, and articles of manufacture, limited to patentable subject matter under 35 USC 101. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include computer programs or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operation described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled//implemented/translated/ converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof, limited to patentable subject matter under 35 U.S.C. 101. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, limited to patentable subject matter under 35 U.S.C. 101, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof, limited to patentable subject matter under 35 U.S.C. 101; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs (e.g., graphene based circuitry). Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into an image processing system. Those having skill in the art will recognize that a typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for administration of inhalable substances to subjects, comprising:
    means for assessing one or more parameters associated with use of an inhaler by a subject;
    means for administering at least one active agent to the subject in response to assessing the one or more parameters associated with use of the inhaler, including at least means for actuating at least one controllable agent valve to release the at least one active agent from at least one aerosol canister in a direction that is transverse to a flow direction in a flow channel during inhalation by the subject in response to the means for assessing one or more parameters associated with use of the inhaler by the subject; and
    means for administering at least one incentive agent to the subject in coordination with administering the at least one active agent, including at least means for actuating at least one controllable incentive valve to release the at least one incentive agent from at least one other aerosol canister in response to the means for assessing one or more parameters associated with use of the inhaler by the subject.

2. The system of claim 1, wherein the means for assessing one or more parameters associated with use of an inhaler by a subject comprises:
    means for assessing one or more parameters associated with respiration, the one or more parameters including at least a time period of breath holding after an inhalation by the subject.

3. The system of claim 1, wherein the means for assessing one or more parameters associated with use of an inhaler by a subject comprises:
    means for assessing one or more parameters associated with inhalation.

4. The system of claim 1, wherein the means for assessing one or more parameters associated with use of an inhaler by a subject comprises:
    means for assessing a time period associated with any of an inhalation cycle, a breath hold cycle, or an exhalation cycle through the inhaler.

5. The system of claim 1, wherein the at least one controllable agent valve is configured to release the at least one active agent from the at least one aerosol canister in a direction that is transverse to a flow direction in a flow channel during inhalation by the subject means for assessing one or more parameters associated with use of an inhaler by a subject comprises:
    means for assessing if at least one value associated with a respiration parameter meets or exceeds a threshold value.

6. The system of claim 1, wherein the means for assessing one or more parameters associated with use of an inhaler by a subject comprises:
    means for assessing if at least one value associated with an inhalation parameter meets or exceeds a threshold value.

7. The system of claim 1, wherein the means for assessing one or more parameters associated with use of an inhaler by a subject comprises:
    means for assessing one or more values associated with one or more inhalation parameters and estimating a quantity of the at least one active agent that will be effectively delivered in response to the one or more assessed values associated with the one or more inhalation parameters.

8. The system of claim 1, wherein the means for assessing one or more parameters associated with use of an inhaler by a subject comprises:
    means for assessing one or more values associated with one or more inhalation parameters and estimating a quantity of the at least one incentive agent that will be effectively delivered in response to the one or more assessed values associated with the one or more inhalation parameters.

9. The system of claim 1, wherein the means for administering at least one active agent to the subject in response to assessing the one or more parameters associated with use of the inhaler, including at least means for actuating at least one controllable agent valve to release the at least one active agent from at least one aerosol canister in response to the means for assessing one or more parameters associated with use of the inhaler by the subject, comprises:
    means for administering the at least one active agent to the subject when at least one value associated with a respiration parameter meets or exceeds a threshold value.

10. The system of claim 1, wherein the means for administering at least one active agent to the subject in response to assessing the one or more parameters associated with use of the inhaler, including at least means for actuating at least one controllable agent valve to release the at least one active agent from at least one aerosol canister in response to the means for assessing one or more parameters associated with use of the inhaler by the subject, comprises:
    means for administering the at least one active agent to the subject when at least one value associated with an inhalation parameter meets or exceeds a threshold value.

11. The system of claim 1, wherein the means for administering at least one incentive agent to the subject in coordination with administering the at least one active agent, including at least means for actuating at least one controllable incentive valve to release the at least one incentive agent from at least one other aerosol canister in response to the means for assessing one or more parameters associated with use of the inhaler by the subject, comprises:
    means for administering the at least one incentive agent after the at least one active agent is administered.

12. The system of claim 1, wherein the means for administering at least one incentive agent to the subject in coordination with administering the at least one active agent, including at least means for actuating at least one controllable incentive valve to release the at least one incentive agent from at least one other aerosol canister in response to the means for assessing one or more parameters associated with use of the inhaler by the subject, comprises:
    means for administering the at least one incentive agent in a quantity that is based on a quantity of the at least one active agent that was delivered to the subject.

13. The system of claim 1, wherein the means for administering at least one incentive agent to the subject in coordination with administering the at least one active agent, including at least means for actuating at least one controllable incentive valve to release the at least one incentive agent from at least one other aerosol canister in response to the means for assessing one or more parameters associated with use of the inhaler by the subject, comprises:
    means for administering the at least one incentive agent in response to assessing at least one value associated with a respiration parameter associated with use of the inhaler.

14. The system of claim 1, wherein the means for administering at least one incentive agent to the subject in coordination with administering the at least one active agent, including at least means for actuating at least one controllable incentive valve to release the at least one incentive agent from at least one other aerosol canister in response to the means for assessing one or more parameters associated with use of the inhaler by the subject, comprises:
    means for administering the at least one incentive agent to the subject when a quantity of the at least one incentive agent included in an exhalant of the subject meets or exceeds a threshold value.

15. The system of claim 1, wherein the means for administering at least one incentive agent to the subject in coordination with administering the at least one active agent, including at least means for actuating at least one controllable incentive valve to release the at least one incentive agent from at least one other aerosol canister in response to the means for assessing one or more parameters associated with use of the inhaler by the subject, comprises:
    means for administering the at least one incentive agent to the subject when a quantity of the at least one active agent included in an exhalant of the subject meets or exceeds a threshold value.

16. The system of claim 1, further comprising:
    means for displaying a comparison of an assessed value associated with one or more respiration parameters with one or more levels associated with the one or more respiration parameters.

17. The system of claim 16, wherein the means for displaying a comparison of an assessed value associated with one or more respiration parameters with one or more levels associated with the one or more respiration parameters comprises:

means for displaying a comparison of the assessed value associated with one or more respiration parameters to a range of levels associated with the one or more respiration parameters and instructing the subject to achieve a value of the one or more respiration parameters that is within a range of threshold levels associated with the one or more respiration parameters.

18. The system of claim 1, further comprising:
means for instructing the subject to achieve one or more values associated with one or more respiration parameters.

19. The system of claim 18, wherein the means for instructing the subject to achieve one or more values associated with one or more respiration parameters comprises:
means for instructing the subject to achieve one or more values associated with one or more exhalation parameters that meet or exceed one or more threshold levels associated with the one or more respiration parameters.

20. The system of claim 1, further comprising:
means for accepting information associated with one or more parameters associated with the subject.

21. The system of claim 20, wherein the means for accepting information associated with one or more parameters associated with the subject comprises:
means for accepting information associated with one or more physical parameters associated with the subject.

22. The system of claim 20, wherein the means for accepting information associated with one or more parameters associated with the subject comprises:
means for accepting information associated with one or more parameters associated with the subject and using the information in combination with one or more delivery parameters to estimate a quantity of the active agent that will be effectively delivered to the subject.

23. The system of claim 1, further comprising:
means for assessing one or more parameters associated with administering the at least one active agent to the subject.

24. The system of claim 23, wherein the means for assessing one or more parameters associated with administering the at least one active agent to the subject comprises:
means for assessing a quantity of the at least one active agent that was administered to the subject.

25. The system of claim 23, wherein the means for assessing one or more parameters associated with administering the at least one active agent to the subject comprises:
means for assessing at least one quantity of at least one of the at least one active agent or the at least one incentive agent that was administered to the subject and then repeating the administration of one or more of the at least one active agent or the at least one incentive agent until at least one preselected quantity of one or more of the at least one active agent or the at least one incentive agent is administered to the subject.

26. The system of claim 23, further comprising:
means for predicting one or more locations in the pulmonary tract of the subject where the at least one active agent was delivered in response to the one or more parameters associated with administration of the at least one active agent to the subject.

27. The system of claim 1, further comprising:
means for assessing during an exhalation by the subject one or more parameters associated with administering of at least one of the at least one active agent or the at least one incentive agent to the subject.

28. The system of claim 27, further comprising:
means for predicting one or more locations in the pulmonary tract of the subject where the at least one incentive agent was delivered in response to the one or more parameters assessed during exhalation by the subject that are associated with administration of the at least one of the at least one active agent or the at least one incentive agent to the subject.

29. The system of claim 1, wherein the means for administering at least one active agent to the subject in response to assessing the one or more parameters associated with use of the inhaler, including at least means for actuating at least one controllable agent valve to release the at least one active agent from at least one aerosol canister in response to the means for assessing one or more parameters associated with use of the inhaler by the subject, comprises:
means for administering at least one active agent to the subject in response to assessing the one or more parameters associated with use of the inhaler and determining which stage of an inhalation cycle to administer the at least one active agent.

30. The system of claim 29, wherein the means for administering at least one active agent to the subject in response to assessing the one or more parameters associated with use of the inhaler and determining which stage of an inhalation cycle to administer the at least one active agent comprises:
means for administering at least one active agent to the subject in response to assessing the one or more parameters associated with use of the inhaler and determining which stage of an inhalation cycle to administer the at least one active agent to control a location in a pulmonary tract of the subject to which the at least one active agent is administered.

31. A system for administration of inhalable substances to subjects, comprising:
means for assessing if at least one value associated with a respiration parameter meets or exceeds a threshold value associated with use of an inhaler by a subject;
means for administering at least one active agent to the subject if the at least one value meets or exceeds the threshold value, including at least means for actuating at least one controllable agent valve to release the at least one active agent from at least one aerosol canister in a direction that is transverse to a flow direction in a flow channel during inhalation by the subject in response to the means for assessing one or more parameters associated with use of the inhaler by the subject; and
means for administering at least one incentive agent to the subject in coordination with administering the at least one active agent, including at least means for actuating at least one controllable incentive valve to release the at least one incentive agent from at least one other aerosol canister in response to the means for assessing one or more parameters associated with use of the inhaler by the subject.

32. A system for administration of inhalable substances to subjects, comprising:
means for assessing one or more values associated with at least one respiration parameter associated with use of an inhaler by a subject;
means for displaying a comparison of the one or more values with one or more threshold levels associated with the at least one respiration parameter;
means for administering at least one active agent to the subject in response to assessing the one or more values, including at least means for actuating at least one controllable agent valve to release the at least one active agent from at least one aerosol canister in a direction that is transverse to a flow direction in a flow channel during inhalation by the subject in response to the means for assessing one or more parameters associated with use of the inhaler by the subject; and means for administering at least one incentive agent to the subject in coordination with administering the at least one active agent, including at least means for actuating at least one controllable incentive valve to release the at least one incentive agent from at least one other aerosol canister in response to the means for assessing one or more parameters associated with use of the inhaler by the subject.

* * *